(12) United States Patent
Chan et al.

(10) Patent No.: US 8,682,591 B2
(45) Date of Patent: Mar. 25, 2014

(54) BIOMARKERS FOR OVARIAN CANCER

(75) Inventors: Daniel W. Chan, Clarksville, MD (US); Zhen Zhang, Dayton, MD (US); Eric Fung, Los Altos, CA (US); Xiao-Ying Meng, Fremont, CA (US)

(73) Assignees: Vermillion, Inc., Austin, TX (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/372,137

(22) Filed: Feb. 13, 2012

(65) Prior Publication Data

US 2012/0220476 A1  Aug. 30, 2012

Related U.S. Application Data

(63) Continuation of application No. 10/594,874, filed as application No. PCT/US2005/010783 on Mar. 31, 2005, now abandoned.

(60) Provisional application No. 60/632,474, filed on Dec. 1, 2004, provisional application No. 60/558,422, filed on Mar. 31, 2004.

(51) Int. Cl.
  *G01N 33/48* (2006.01)
  *G01N 31/00* (2006.01)
  *C12Q 1/00* (2006.01)
  *G06F 19/00* (2011.01)

(52) U.S. Cl.
  CPC ................................... *G06F 19/34* (2013.01)
  USPC .................................. 702/19; 702/22; 435/4

(58) Field of Classification Search
  None
  See application file for complete search history.

(56) References Cited

U.S. PATENT DOCUMENTS 7,605,003 B2 * 10/2009 Chan et al. .................... 436/178

FOREIGN PATENT DOCUMENTS

| AU | 2003256858 B2 * | 8/2003 |
| WO | WO-02/082075 A2 | 10/2002 |
| WO | WO-03/021226 A2 | 3/2003 |
| WO | WO-03/048775 A2 | 6/2003 |
| WO | WO-2004/013609 A2 | 2/2004 |

OTHER PUBLICATIONS

Zhang et al. Three biomarkers identified from serum proteomic analysis for the detection of early stage ovarian cancer. Cancer Research, Aug. 15, 2004, vol. 64, pp. 5882-5890.*
Astion et al., "Application of neural networks to the interpretation of laboratory data in cancer diagnosis", Clinical Chemistry, 38:34-38 (1992).
Ramaker et al., "Transthyretin—An explanation of "anomalous" serum thyroid values in severe illness?", Journal of Clinical Chemistry and Clinical Biochemistry, 28:155-161 (1990).
Shapiro et al., "Comparison of immunonephelometry and electroimmunoassy for estimation of plasma apolipoprotein A-1", 103:7-13 (1980).
Witze ES. et al. "Mapping protein post-translational modifications with mass spectrometry" Nat Methods. Oct. 2007;4(10):798-806.
Wielding et al. "Application of backpropagation neural networks to diagnosis of brest and ovarian cancer", Cancer Letters, 77:145-153 (1994).
"Promising validation results for ovarian cancer biomarkers presented at meeting", Cancer Vaccine Week, p. 86 (2004).

* cited by examiner

*Primary Examiner* — Russell S Negin
(74) *Attorney, Agent, or Firm* — Melissa Hunter-Ensor; Saul Ewing LLP

(57) ABSTRACT

The present invention relates to a method of qualifying ovarian cancer status in a subject comprising: (a) measuring at least one biomarker in a sample from the subject and (b) correlating the measurement with ovarian cancer status. The invention further relates to kits for qualifying ovarian cancer status in a subject.

11 Claims, 21 Drawing Sheets

* Part of biomarker discovery set.

† In Panels A, C, E, and G, epithelial ovarian cancer included both invasive and borderline tumors.

* Part of biomarker discovery set.

† In Panels A, C, E, and G, epithelial ovarian cancer included both invasive and borderline tumors.

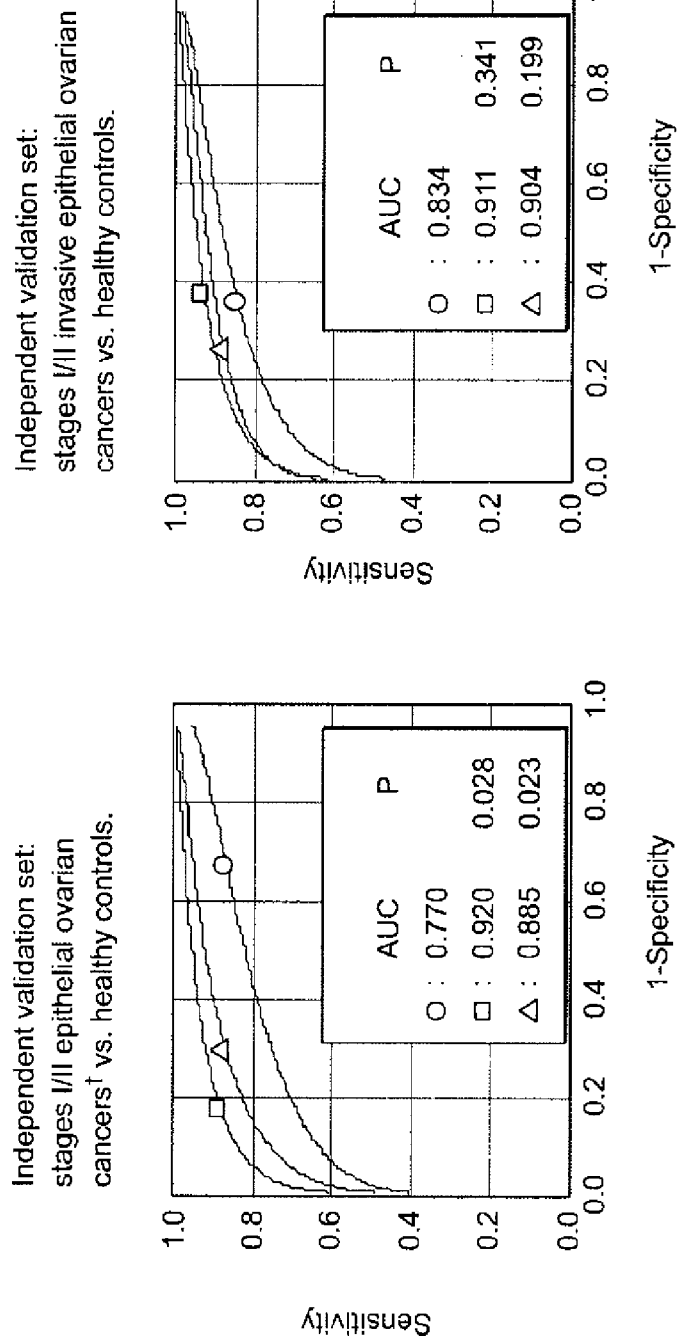

Scatter plots from patient samples

BIOMARKERS FOR OVARIAN CANCER

RELATED APPLICATIONS

This application is a continuation application of U.S. application Ser. No. 10/594,874, filed on Sep. 28, 2006, which is the U.S. national phase application, pursuant to 35 U.S.C. §371, of PCT international application Ser. No. PCT/US2005/010783, filed Mar. 31, 2005, designating the U.S. and published in English on Oct. 20, 2005 as publication WO/2005/098447, which claims the benefit of U.S. Provisional Application Ser. No. 60/632,474, filed on Dec. 1, 2004 and U.S. Provisional Application Ser. No. 60/558,422, filed on Mar. 31, 2004. The entire contents of the aforementioned patent applications are hereby incorporated herein by reference in their entirety.

FIELD OF THE INVENTION

The invention provides for biomarkers important in the detection of ovarian cancer. The markers were identified by distinguishing the serum protein profile in ovarian cancer patients from healthy individuals using SELDI analysis. The present invention relates the biomarkers to a system and method in which the biomarkers are used for the qualification of ovarian cancer status. The present invention also identifies the biomarkers as known proteins.

BACKGROUND OF THE INVENTION

Ovarian cancer is among the most lethal gynecologic malignancies in developed countries. Annually in the United States alone, approximately 23,000 women are diagnosed with the disease and almost 14,000 women die from it. (Jamal, A., et al., CA Cancer J. Clin, 2002; 52:23-47). Despite progress in cancer therapy, ovarian cancer mortality has remained virtually unchanged over the past two decades. (Id.) Given the steep survival gradient relative to the stage at which the disease is diagnosed, early detection remains the most important factor in improving long-term survival of ovarian cancer patients.

The poor prognosis of ovarian cancer diagnosed at late stages, the cost and risk associated with confirmatory diagnostic procedures, and its relatively low prevalence in the general population together pose extremely stringent requirements on the sensitivity and specificity of a test for it to be used for screening for ovarian cancer in the general population.

The identification of tumor markers suitable for the early detection and diagnosis of cancer holds great promise to improve the clinical outcome of patients. It is especially important for patients presenting with vague or no symptoms or with tumors that are relatively inaccessible to physical examination. Despite considerable effort directed at early detection, no cost effective screening tests have been developed (Paley P J., *Curr Opin Oncol*, 2001; 13(5):399-402) and women generally present with disseminated disease at diagnosis. (Ozols R F, et al., Epithelial ovarian cancer. In: Hoskins W J, Perez C A, Young R C, editors. Principles and Practice of Gynecologic Oncology. 3rd ed. Philadelphia: Lippincott, Williams and Wilkins; 2000. p. 981-1057).

The best-characterized tumor marker, CA125, is negative in approximately 30-40% of stage I ovarian carcinomas and its levels are elevated in a variety of benign diseases. (Meyer T, et al., *Br J Cancer*, 2000; 82(9):1535-8; Buamah P., *J Surg Oncol*, 2000; 75(4):264-5; Tuxen M K, et al., *Cancer Treat Rev*, 1995; 21(3):215-45). Its use as a population-based screening tool for early detection and diagnosis of ovarian cancer is hindered by its low sensitivity and specificity. (MacDonald N D, et al., *Eur J Obstet Gynecol Reprod Biol*, 1999; 82(2):155-7; Jacobs I, et al., *Hum Reprod*, 1989; 4(1):1-12; Shih I-M, et al., Tumor markers in ovarian cancer. In: Diamandis E P, Fritsche, H., Lilja, H., Chan, D. W., and Schwartz, M., editor. Tumor markers physiology, pathobiology, technology and clinical applications. Philadelphia: AACC Press; in press). Although pelvic and more recently vaginal sonography has been used to screen high-risk patients, neither technique has the sufficient sensitivity and specificity to be applied to the general population. (MacDonald N D, et al., supra). Recent efforts in using CA125 in combination with additional tumor markers (Woolas R P X F, et al., *J Natl Cancer Inst*, 1993; 85(21):1748-51; Woolas R P, et al., *Gynecol Oncol*, 1995; 59(1):111-6; Zhang Z, et al., *Gynecol Oncol*, 1999; 73(1):56-61; Zhang Z, et al., Use of Multiple Markers to Detect Stage I Epithelial Ovarian Cancers: Neural Network Analysis Improves Performance. American Society of Clinical Oncology 2001; Annual Meeting, Abstract) in a longitudinal risk of cancer model (Skates S J, et al., *Cancer*, 1995; 76(10 Suppl):2004-10), and in tandem with ultrasound as a second line test (Jacobs I D A, et al., *Br Med J*, 1993; 306(6884):1030-34; Menon U T A, et al., *British Journal of Obstetrics and Gynecology*, 2000; 107(2):165-69) have shown promising results in improving overall test specificity, which is critical for a disease such as ovarian cancer that has a relatively low prevalence.

Due to the dismal prognosis of late stage ovarian cancer, it is the general consensus that a physician will accept a test with a minimal positive predictive value of 10%. (Bast, R. C., et al., Cancer Treatment and Research, 2002; 107:61-97). Extending this to the general population, a general screening test would require a sensitivity greater than 70% and a specificity of 99.6%. Currently, none of the existing serologic markers, such as CA125, CA72-4, or M-CSF, individually delivers such a performance. (Bast, R. C., et al., Int J Biol Markers, 1998; 13:179-87).

Thus, there is a critical need for new serological markers that individually or in combination with other markers or diagnostic modalities deliver the required sensitivity and specificity for early detection of ovarian cancer. (Bast R C, et al., Early detection of ovarian cancer: promise and reality. Ovarian Cancer: ISIS Medical Media Ltd., Oxford, UK; 2001. in press). Without an acceptable screening test, early detection remains the most critical factor in improving long-term survival of patients with ovarian cancer.

Thus, it is desirable to have a reliable and accurate method of determining the ovarian cancer status in patients, the results of which can then be used to manage subject treatment.

SUMMARY OF THE INVENTION

The present invention provides sensitive and quick methods and kits that are useful for determining the ovarian cancer status by measuring these markers. The measurement of these markers in patient samples provides information that diagnosticians can correlate with a probable diagnosis of human cancer or a negative diagnosis (e.g., normal or disease-free). The markers are characterized by molecular weight and/or by their known protein identities. The markers can be resolved from other proteins in a sample by using a variety of fractionation techniques, e.g., chromatographic separation coupled with mass spectrometry, protein capture using immobilized antibodies or by traditional immunoassays. In preferred embodiments, the method of resolution involves Surface- Enhanced Laser Desorption/Ionization ("SELDI") mass spectrometry, in which the surface of the mass spectrometry probe comprises adsorbents that bind the markers.

More specifically, three biomarkers were discovered and subsequently identified, in accordance with the methods described herein as (1) apolipoprotein A1 (referred to herein as "Apo A1"), including modified forms of Apo A1, (2) transthyretin, including a truncated form of transthyretin, (referred to herein as "transthyretin ΔN10"), and modified forms of transthyretin, and (3) one of at least three cleavage fragments of inter-α-trypsin inhibitor heavy chain H4 (referred to herein as "IAIH4 fragment").

The present invention provides a method of qualifying ovarian cancer status in a subject comprising (a) measuring at least one biomarker in a sample from the subject, wherein the biomarker is selected from the group consisting of Apo A1, modified Apo A1, transthyretin ΔN10, native transthyretin, cysteinylated transthyretin, sulfonated transthyretin, CysGly modified transthyretin, glutathionylated transthyretin, IAIH4 fragment no. 1, IAIH4 fragment no. 2, and IAIH4 fragment no. 3, and combinations thereof, and (b) correlating the measurement with ovarian cancer status. In certain methods, the measuring step comprises detecting the presence or absence of markers in the sample. In other methods, the measuring step comprises quantifying the amount of marker(s) in the sample. In other methods, the measuring step comprises qualifying the type of biomarker in the sample.

The invention also relates to methods wherein the measuring step comprises: providing a subject sample of blood or a blood derivative; fractionating proteins in the sample on an anion exchange resin and collecting fractions that contain ApoA1, modified ApoA1, transthyretin, and IAIH4 fragment; and capturing ApoA1, transthyretin, and IAIH4 fragment from the fractions on a surface of a substrate comprising capture reagents that bind the protein biomarkers. The blood derivative is, e.g., serum or plasma. In preferred embodiments, the substrate is a SELDI probe comprising an IMAC copper surface and wherein the protein biomarkers are detected by SELDI. In other embodiments, the substrate is a SELDI probe comprising biospecific affinity reagents that bind ApoA1, transthyretin, and IAIH4 fragment and wherein the protein biomarkers are detected by SELDI. In other embodiments, the substrate is a microtiter plate comprising biospecific affinity reagents that bind ApoA1, transthyretin, and IAIH4 fragment and the protein biomarkers are detected by immunoassay.

In certain embodiments, the methods further comprise managing subject treatment based on the status determined by the method. For example, if the result of the methods of the present invention is inconclusive or there is reason that confirmation of status is necessary, the physician may order more tests. Alternatively, if the status indicates that surgery is appropriate, the physician may schedule the patient for surgery. Likewise, if the result of the test is positive, e.g., the status is late stage ovarian cancer or if the status is otherwise acute, no further action may be warranted. Furthermore, if the results show that treatment has been successful, no further management may be necessary.

The invention also provides for such methods where the at least one biomarker is measured again after subject management. In these instances, the step of managing subject treatment is then repeated and/or altered depending on the result obtained.

The term "ovarian cancer status" refers to the status of the disease in the patient. Examples of types of ovarian cancer statuses include, but are not limited to, the subject's risk of cancer, the presence or absence of disease, the stage of disease in a patient, and the effectiveness of treatment of disease. Other statuses and degrees of each status are known in the art.

The biomarkers that are useful in the methods of the present invention are selected from Apo A1, modified Apo A1, transthyretin ΔN10, native transthyretin, cysteinylated transthyretin, sulfonated transthyretin, CysGly modified transthyretin, glutathionylated transthretin, IAIH4 fragment no. 1, IAIH4 fragment no. 2, and IAIH4 fragment no. 3. In certain preferred embodiments, the method further comprises measuring at least one previously known marker (herein referred to as "Marker 4") in a sample from the subject and correlating measurement of the at least one Marker 4 and the measurement of Apo A1, transthyretin, and IAIH4 fragment with ovarian cancer status. In certain embodiments only one Marker 4 is measured, in addition to the markers selected from Apo A1, transthyretin, and IAIH4 fragment, while in other embodiments more than one Marker 4 is measured.

Examples of Marker 4 include known ovarian cancer biomarkers, e.g., but are not limited to, CA125, CA125 II, CA15-3, CA19-9, CA72-4, CA195, tumor associated trypsin inhibitor (TATI), CEA, placental alkaline phosphatase (PLAP), Sialyl TN, galactosyltransferase, macrophage colony stimulating factor (M-CSF, CSF-1), lysophosphatidic acid (LPA), 110 kD component of the extracellular domain of the epidermal growth factor receptor (p110EGFR), tissue kallikreins, e.g., kallikrein 6 and kallikrein 10 (NES-1), prostasin, HE4, creatine kinase B (CKB), LASA, HER-2/neu, urinary gonadotropin peptide, Dianon NB 70/K, Tissue peptide antigen (TPA), osteopontin and haptoglobin, bikunin, MUC1, and protein variants (e.g., cleavage forms, isoforms) of the markers.

In certain embodiments, the method provides for the measurement of all three biomarkers: Apo A1, transthyretin, and IAIH4 fragment (wherein the Apo A1 is selected from unmodified Apo A1 and modified, wherein the thransthyretin is selected from the group consisting of transthyretin ΔN10, native transthyretin, cysteinylated transthyretin, sulfonated transthyretin, CysGly modified transthyretin, and glutathionylated transthyretin, and wherein the IAIH4 fragment is selected from the group consisting of IAIH4 fragment nos. 1, 2, and 3). In another embodiment, the method provides for the measurement of two biomarkers, Apo A1 and transthyretin (wherein the Apo A1 is selected from unmodified Apo A1 and modified, wherein the thransthyretin is selected from the group consisting of transthyretin ΔN10, native transthyretin, cysteinylated transthyretin, sulfonated transthyretin, CysGly modified transthyretin, and glutathionylated transthyretin). In a preferred embodiment, the two biomarkers are modified ApoA1 and cysteinylated transthyretin. In another embodiment, the method provides for the measurement of Apo A1, modified ApoA1, transthyretin ΔN10, native transthyretin, cysteinylated transthyretin, sulfonated transthyretin, CysGly modified transthyretin, glutathionylated transthyretin, and all three IAIH4 fragments. In some embodiments, at least one known marker, Marker 4, in a sample from the subject is also measured, and the measurement of Marker 4 and the measurements of the three other biomarkers (Apo A1, transthyretin, and IAIH4 fragment) are correlated with ovarian cancer status. As aforesaid, in certain embodiments, the biomarkers that are measured comprise: all three biomarkers (Apo A1, transthyretin, and IAIH4 fragment, wherein the Apo A1 is selected from unmodified Apo A1 and modified Apo A1, wherein the thransthyretin is selected from the group consisting of transthyretin ΔN10, native transthyretin, cysteinylated transthyretin, sulfonated transthyretin, CysGly modified transthyretin, and glutathionylated transthyretin, and wherein the IAIH4 fragment is selected from the group consisting of IAIH4 fragment nos. 1, 2, and 3, or may comprise two or three IAIH4 fragments) and two or more markers from the group designated as Marker 4.

The present invention also relates to biomarkers designated as Markers I through XLVIII. Protein markers of the invention can be characterized in one or more of several respects. In particular, in one aspect, these markers are characterized by molecular weights under the conditions specified herein, particularly as determined by mass spectral analysis. In another aspect, the markers can be characterized by features of the markers' mass spectral signature such as size (including area) and/or shape of the markers' spectral peaks, features including proximity, size and shape of neighboring peaks, etc. In yet another aspect, the markers can be characterized by affinity binding characteristics, particularly ability to binding to an IMAC copper adsorbent under specified conditions, however, other metals, e.g., nickel, may also be used. In preferred embodiments, markers of the invention may be characterized by each of such aspects, i.e. molecular weight, mass spectral signature and IMAC-Cu absorbent binding.

For the mass values of the markers disclosed herein, the mass accuracy of the spectral instrument is considered to be about within +/−0.15 percent of the disclosed molecular weight value. Additionally, to such recognized accuracy variations of the instrument, the spectral mass determination can vary within resolution limits of from about 400 to 1000 m/dm, where m is mass and dm is the mass spectral peak width at 0.5 peak height. Those mass accuracy and resolution variances associated with the mass spectral instrument and operation thereof are reflected in the use of the term "about" in the disclosure of the mass of each of Markers I through XLVIII. It is also intended that such mass accuracy and resolution variances and thus meaning of the term "about" with respect to the mass of each of the markers disclosed herein is inclusive of variants of the markers as may exist due to sex, genotype and/or ethnicity of the subject and the particular cancer or origin or stage thereof.

The present invention further provides a method of qualifying ovarian cancer status in a subject comprising (a) measuring at least one biomarker in a sample from the subject, wherein the biomarker is selected from the group consisting of Markers I through XLVIII and combinations thereof, and (b) correlating the measurement with ovarian cancer status. In certain methods, the measuring step comprises detecting the presence or absence of markers in the sample. In other methods, the measuring step comprises quantifying the amount of marker(s) in the sample. In other methods, the measuring step comprises qualifying the type of biomarker in the sample.

The accuracy of a diagnostic test is characterized by a Receiver Operating Characteristic curve ("ROC curve"). An ROC is a plot of the true positive rate against the false positive rate for the different possible cutpoints of a diagnostic test. An ROC curve shows the relationship between sensitivity and specificity. That is, an increase in sensitivity will be accompanied by a decrease in specificity. The closer the curve follows the left axis and then the top edge of the ROC space, the more accurate the test. Conversely, the closer the curve comes to the 45-degree diagonal of the ROC graph, the less accurate the test. The area under the ROC is a measure of test accuracy. The accuracy of the test depends on how well the test separates the group being tested into those with and without the disease in question. An area under the curve (referred to as "AUC") of 1 represents a perfect test, while an area of 0.5 represents a less useful test. Thus, preferred biomarkers and diagnostic methods of the present invention have an AUC greater than 0.50, more preferred tests have an AUC greater than 0.60, more preferred tests have an AUC greater than 0.70.

Preferred methods of measuring the biomarkers include use of a biochip array. Biochip arrays useful in the invention include protein and nucleic acid arrays. One or more markers are captured on the biochip array and subjected to laser ionization to detect the molecular weight of the markers. Analysis of the markers is, for example, by molecular weight of the one or more markers against a threshold intensity that is normalized against total ion current. Preferably, logarithmic transformation is used for reducing peak intensity ranges to limit the number of markers detected.

In preferred methods of the present invention, the step of correlating the measurement of the biomarkers with ovarian cancer status is performed by a software classification algorithm. Preferably, data is generated on immobilized subject samples on a biochip array, by subjecting said biochip array to laser ionization and detecting intensity of signal for mass/charge ratio; and, transforming the data into computer readable form; and executing an algorithm that classifies the data according to user input parameters, for detecting signals that represent markers present in ovarian cancer patients and are lacking in non-cancer subject controls.

Preferably the biochip surfaces are, for example, ionic, anionic, comprised of immobilized nickel ions, comprised of a mixture of positive and negative ions, comprised of one or more antibodies, single or double stranded nucleic acids, proteins, peptides or fragments thereof, amino acid probes, or phage display libraries.

In other preferred methods one or more of the markers are measured using laser desorption/ionization mass spectrometry, comprising providing a probe adapted for use with a mass spectrometer comprising an adsorbent attached thereto, and contacting the subject sample with the adsorbent, and; desorbing and ionizing the marker or markers from the probe and detecting the deionized/ionized markers with the mass spectrometer.

Preferably, the laser desorption/ionization mass spectrometry comprises: providing a substrate comprising an adsorbent attached thereto; contacting the subject sample with the adsorbent; placing the substrate on a probe adapted for use with a mass spectrometer comprising an adsorbent attached thereto; and, desorbing and ionizing the marker or markers from the probe and detecting the desorbed/ionized marker or markers with the mass spectrometer.

The adsorbent can for example be hydrophobic, hydrophilic, ionic or metal chelate adsorbent, such as, nickel or an antibody, single- or double stranded oligonucleotide, amino acid, protein, peptide or fragments thereof.

The methods of the present invention can be performed on any type of patient sample that would be amenable to such methods, e.g., blood, serum and plasma.

In certain embodiments, a plurality of biomarkers in a sample from the subject are measured, wherein the biomarkers are selected from the group consisting of Apo A1, modified Apo A1, transthyretin ΔN10, native transthyretin, cysteinylated transthyretin, sulfonated transthyretin, CysGly modified transthyretin, glutathionylated transthyretin, IAIH4 fragment no. 1, IAIH4 fragment no. 2, and IAIH4 fragment no. 3, and at least one known marker, Marker 4. In a preferred embodiment, the plurality of biomarkers consists of Apo A1 and transthyretin, and in a more preferred embodiment, the Apo A1 is modified Apo A1, and the transthyretin is cysteinylated transthyretin. In other preferred methods, the plurality of biomarkers consists of Apo A1, modified Apo A1, transthyretin ΔN10, native transthyretin, cysteinylated transthyretin, sulfonated transthyretin, CysGly modified transthyretin, glutathionylated transthyretin, IAIH4 fragment no. 1, IAIH4 fragment no. 2, and IAIH4 fragment no. 3. The measurement of the plurality of biomarkers can also include measuring at least one Marker 4. Preferably, the protein biomarkers are measured by SELDI or immunoassay.

The present invention also provides a method comprising measuring at least one biomarker in a sample from the subject, wherein the biomarker is selected from the group consisting of Apo A1, modified Apo A1, transthyretin ΔN10, native transthyretin, cysteinylated transthyretin, sulfonated transthyretin, CysGly modified transthyretin, glutathionylated transthyretin, IAIH4 fragment no. 1, IAIH4 fragment no. 2, and IAIH4 fragment no. 3, and combinations thereof. In certain of these embodiments, the method further comprises measuring Apo A1 and/or at least one known ovarian cancer marker, i.e., Marker 4, e.g., CA125, CA125 II, CA15-3, CA19-9, CA72-4, CA195, TATI, CEA, PLAP, Sialyl TN, galactosyltransferase, M-CSF, CSF-1, LPA, p110EGFR, tissue kallikreins, prostasin, HE4, CKB, LASA, HER-2/neu, urinary gonadotropin peptide, Dianon NB 70/K, TPA, osteopontin and haptoglobin, bikunin, MUC1, and protein variants (e.g., cleavage forms, isoforms) of the markers.

The present invention also provides kits comprising (a) a capture reagent that binds a biomarker selected from Apo A1, modified Apo A1, transthyretin ANIO, native transthyretin, cysteinylated transthyretin, sulfonated transthyretin, CysGly modified transthyretin, glutathionylated transthyretin, IAIH4 fragment no. 1, IAIH4 fragment no. 2, IAIH4 fragment no. 3, and combinations thereof; and (b) a container comprising at least one of the biomarkers. In preferred embodiments, the capture reagent binds a plurality of the biomarkers. In one embodiment, the plurality comprises Apo A1 and transthyretin, and in a more preferred embodiment, the Apo A1 is modified Apo A1, and the transthyretin is cysteinylated transthyretin. In another embodiment, the plurality comprises Apo A1, modified Apo A1, transthyretin ΔN10, native transthyretin, cysteinylated transthyretin, sulfonated transthyretin, CysGly modified transthyretin, glutathionylated transthyretin, IAIH4 fragment no. 1, IAIH4 fragment no. 2, and IAIH4 fragment no. 3. While the capture reagent can be any type of reagent, preferably the reagent is a SELDI probe. The capture reagent may also bind other known biomarkers, e.g., Marker 4. In certain preferred embodiments, the kit of further comprises a second capture reagent that binds one of the biomarkers that the first capture reagent does not bind.

Further kits provided by the invention comprise (a) a first capture reagent that binds at least one biomarker selected from Apo A1, modified Apo A1, transthyretin ΔN10, native transthyretin, cysteinylated transthyretin, sulfonated transthyretin, CysGly modified transthyretin, glutathionylated transthyretin, IAIH4 fragment no. 1, IAIH4 fragment no. 2, and IAIH4 fragment no. 3, and (b) a second capture reagent that binds at least one of the biomarkers that is not bound by the first capture reagent. Preferably, at least one the capture reagent is an antibody. Certain kits further comprise an MS probe to which at least one capture reagent is attached or is attachable.

In certain kits of the present invention, the capture reagent comprises an immobilized metal chelate ("IMAC").

Certain kits of the present invention further comprise a wash solution that selectively allows retention of the bound biomarker to the capture reagent as compared with other biomarkers after washing.

The invention also provides kits comprising (a) a first capture reagent that binds at least one biomarker selected from Apo A1, modified Apo A1, transthyretin ΔN10, native transthyretin, cysteinylated transthyretin, sulfonated transthyretin, CysGly modified transthyretin, glutathionylated transthyretin, IAIH4 fragment no. 1, IAIH4 fragment no. 2, and IAIH4 fragment no. 3, and (b) instructions for using the capture reagent to measure the biomarker. In certain of these kits, the capture reagent comprises an antibody. Furthermore, some kits further comprise an MS probe to which the capture reagent is attached or is attachable. In some kits, the capture reagent comprises an IMAC. The kits may also contain a wash solution that selectively allows retention of the bound biomarker to the capture reagent as compared with other biomarkers after washing. Preferably, the kit comprises written instructions for use of the kit for determining ovarian cancer status and the instructions provide for contacting a test sample with the capture reagent and measuring one or more biomarkers retained by the capture reagent.

The kit also provides for a capture reagent, which is an antibody, single or double stranded oligonucleotide, amino acid, protein, peptide or fragments thereof.

Measurement of one or more protein biomarkers using the kit, is by mass spectrometry or immunoassays such as an ELISA.

Purified proteins for detection of ovarian cancer and/or generation of antibodies for further diagnostic assays are also provided for. Purified proteins include a purified peptide of SEQ ID NO:1 (IAIH4 fragment no. 1), SEQ ID NO:2 (IAIH4 fragment no. 2), and SEQ ID NO:3 (IAIH4 fragment no. 3). The invention also provides this purified peptide further comprising a detectable label.

The invention also provides an article manufacture comprising at least one capture reagent bound to at least two biomarkers selected from Apo A1, modified Apo A1, transthyretin ΔN10, native transthyretin, cysteinylated transthyretin, sulfonated transthyretin, CysGly modified transthyretin, glutathionylated transthyretin, IAIH4 fragment no. 1, IAIH4 fragment no. 2, and IAIH4 fragment no. 3. Other embodiments of the article of manufacture of the present invention further comprise a capture reagent that binds other known ovarian cancer markers, i.e., Marker 4, e.g., but not limited to, CA125, CA125 II, CA15-3, CA19-9, CA72-4, CA 195, TATI, CEA, PLAP, Sialyl TN, galactosyltransferase, M-CSF, CSF-1, LPA, p110EGFR, tissue kallikreins, prostasin, HE4, CKB, LASA, HER-2/neu, urinary gonadotropin peptide, Dianon NB 70/K, TPA, osteopontin and haptoglobin, bikunin, MUC1 and protein variants (e.g., cleavage forms, isoforms) of the markers.

The present invention also provides a system comprising a plurality of capture reagents each of which has bound to it a different biomarker selected from Apo A1, modified Apo A1, transthyretin ΔN10, native transthyretin, cysteinylated transthyretin, sulfonated transthyretin, CysGly modified transthyretin, glutathionylated transthyretin, IAIH4 fragment no. 1, IAIH4 fragment no. 2, IAIH4 fragment no. 3 and at least one Marker 4.

The present invention also provides a screening test comprising (a) contacting a kallikrein with a kallikrein substrate and with a test agent and (b) determining whether the test agent modulates the activity of the kallikrein. In one such test, the substrate is inter-alpha-trypsin inhibitor heavy chain H4 precursor. In this test, the kallikrein preferably cleaves the substrate into IAIH4 fragment selected from the group consisting of IAIH4 fragment no. 1, IAIH4 fragment no. 2, and IAIH4 fragment no. 3.

In another embodiment, non-invasive medical imaging techniques such as transvaginal ultrasound, positron emisson tomography (PET) or single photon emission computerized tomography (SPECT) imaging are particularly useful for the detection of cancer, coronary artery disease and brain disease. Ultrasound with Doppler flow, PET, and SPECT imaging show the chemical functioning of organs and tissues, while other imaging techniques—such as X-ray, CT and MRI—primarily show structure. The use of ultrasound with flow, PET and SPECT imaging has become increasingly useful for qualifying and monitoring the development of diseases such as ovarian cancer.

The peptide biomarkers disclosed herein, or fragments thereof, can be used in the context of PET and SPECT imaging applications. After modification with appropriate tracer residues for PET or SPECT applications, peptide biomarkers that interact with tumor proteins can be used to image the deposition of biomarkers in ovarian cancer patients.

Other aspects of the invention are described infra.

BRIEF DESCRIPTION OF THE FIGURES

FIGS. 2 (E), (F), (G), and (H) show a comparison of receiver operating characteristic (ROC) curves for CA125 and two multivariate predictive models.

FIGS. 3 (i), (j), (k) and (l) show scatter plots showing the output of the two multivariate predictive models among patients and healthy control in the test set (part of biomarker discovery set) and the independent validation set.

DEFINITIONS

Figure 1:
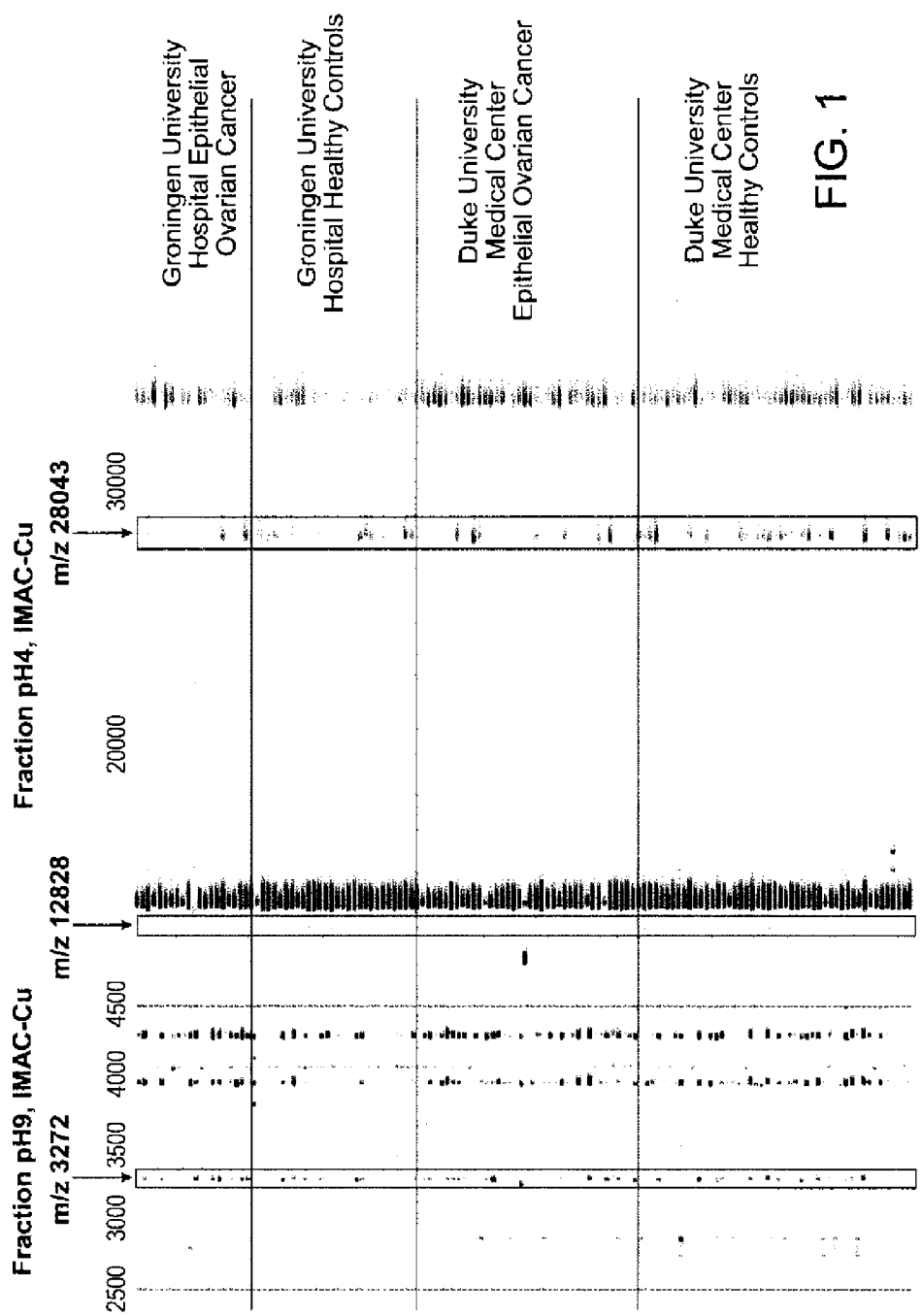
FIG. 1 shows a pseudo-gel view of mass spectra from samples in the biomarker discovery set showing peaks located at m/z of 12828 and 28043 (fraction pH 4, IMAC-Cu array), and at 3272 (fraction pH 9, IMAC-Cu array).
Figures 2A, 2B:
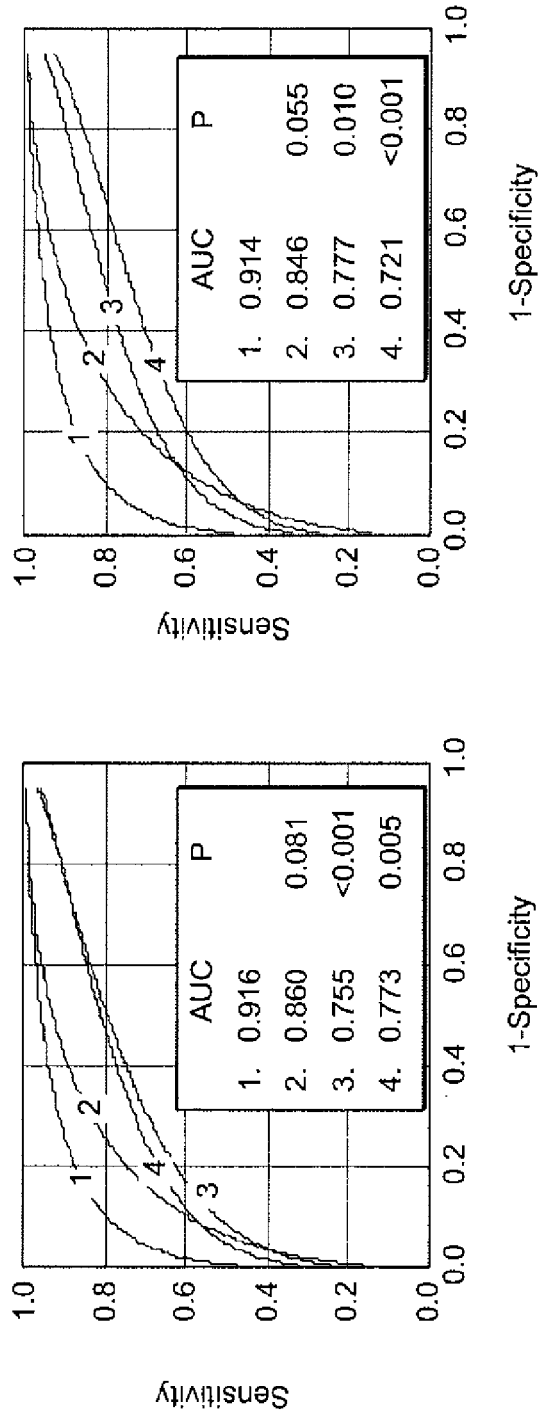
FIGS. 2 (A), (B), (C) and (D) show a comparison of receiver operating characteristic (ROC) curves between CA125 and three identified biomarkers.
Figure 2C:
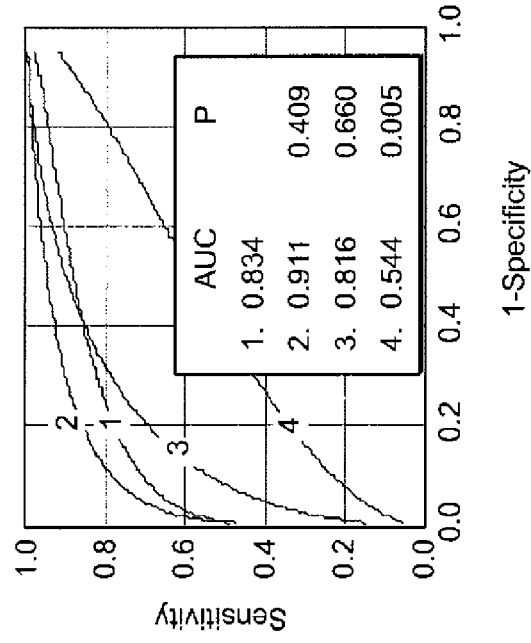
Figure 2D:
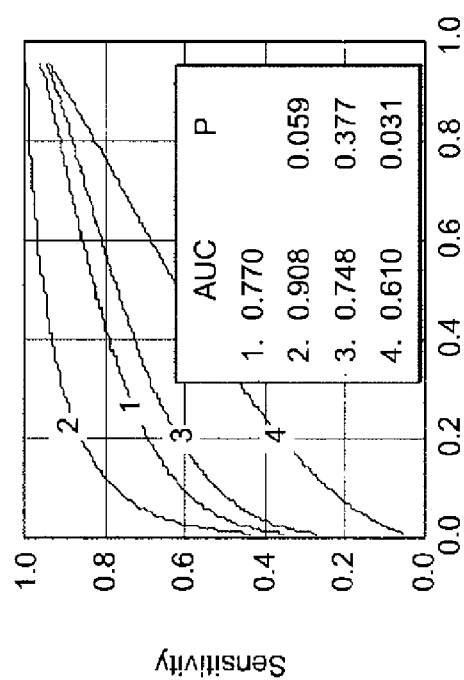
Figures 2E, 2F:
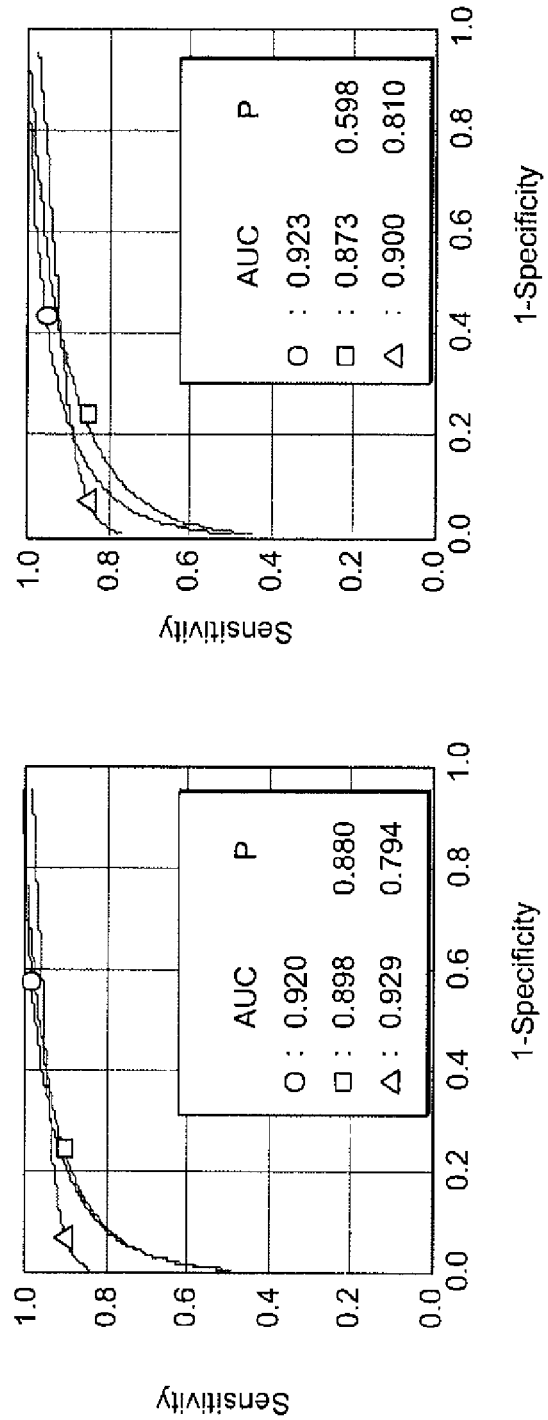
Figure 3A:
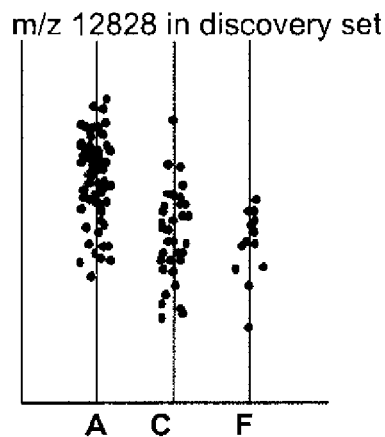
FIGS. 3 (a), (b), (c), (d), (e), (f), (g), and (h) show scatter plots showing distributions of the three identified biomarkers and CA125 among patients and healthy controls in the biomarker discovery set and the independent validation set (panels a-h).
Figure 3B:
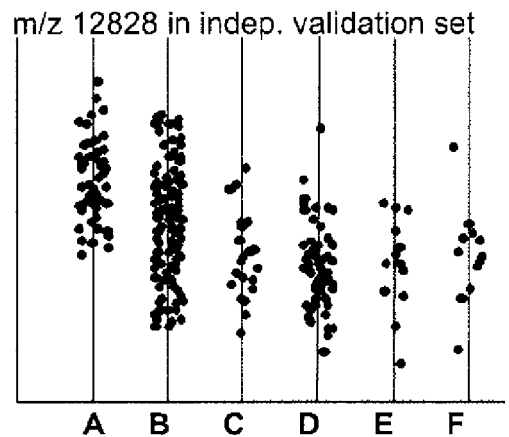
Figure 3C:
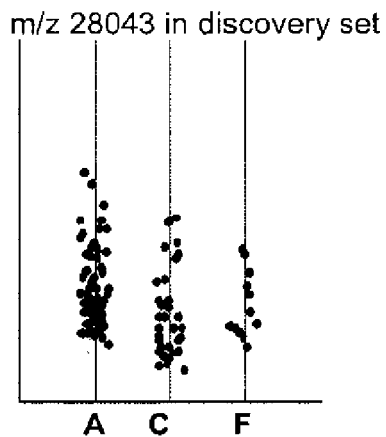
Figure 3D:
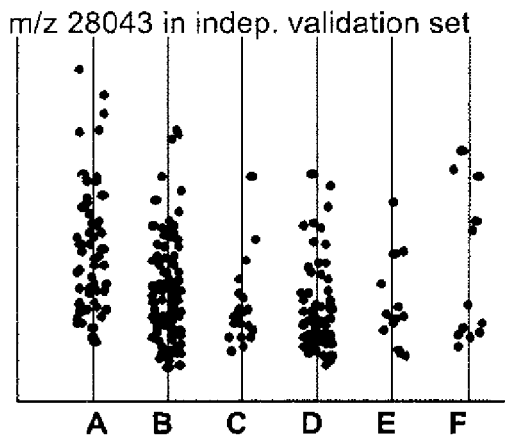
Figure 3E:
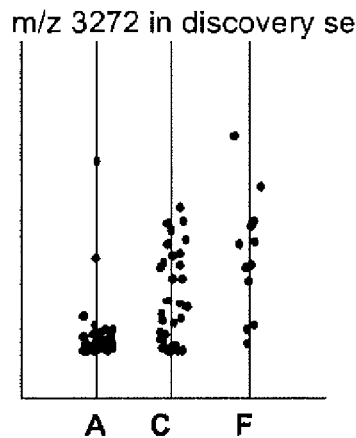
Figure 3F:
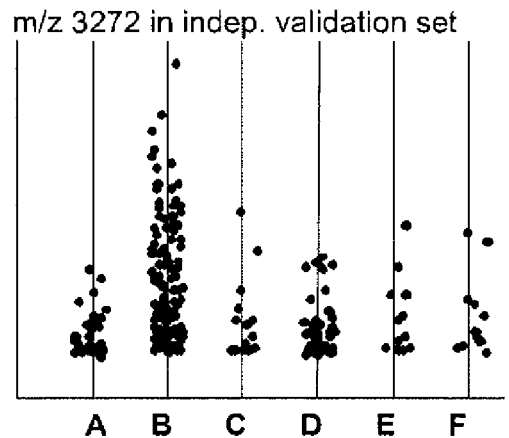
Figure 3G:
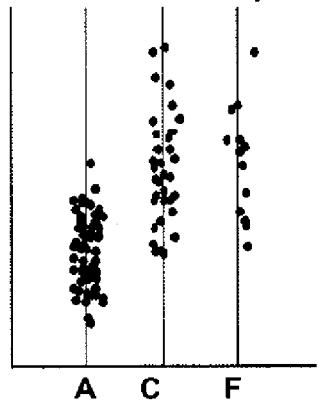
Figure 3H:
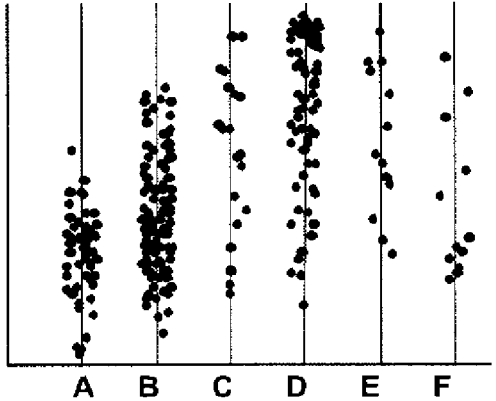
Figure 3I:
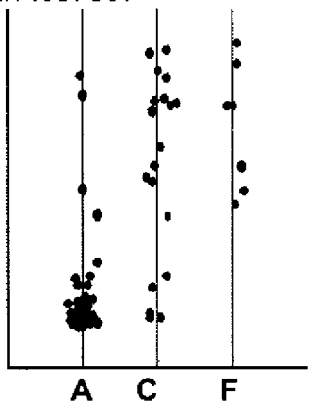
Figure 3J:
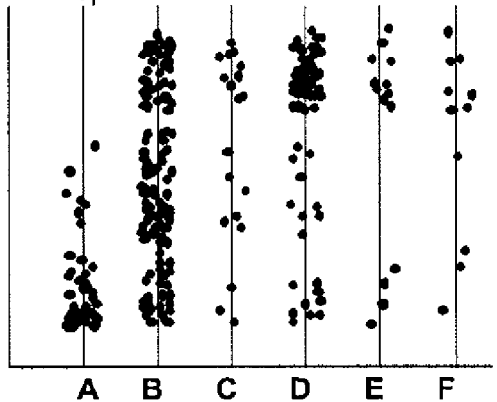
Figure 3K:
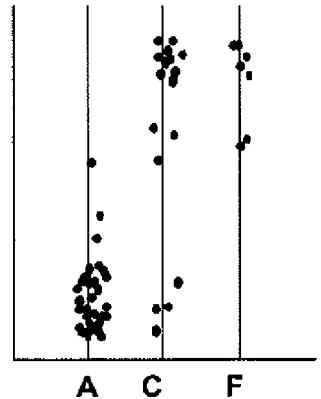
Figure 3L:
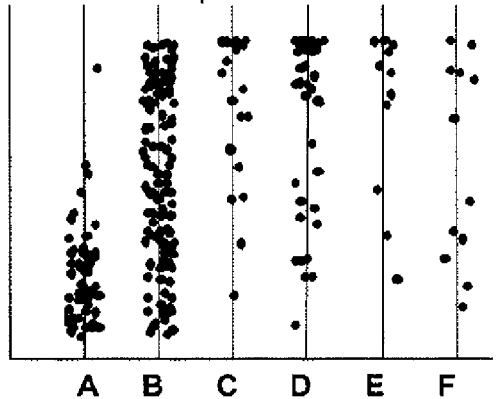

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

"Gas phase ion spectrometer" refers to an apparatus that detects gas phase ions. Gas phase ion spectrometers include an ion source that supplies gas phase ions. Gas phase ion spectrometers include, for example, mass spectrometers, ion mobility spectrometers, and total ion current measuring devices. "Gas phase ion spectrometry" refers to the use of a gas phase ion spectrometer to detect gas phase ions.

"Mass spectrometer" refers to a gas phase ion spectrometer that measures a parameter that can be translated into mass-to-charge ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids of these. "Mass spectrometry" refers to the use of a mass spectrometer to detect gas phase ions.

"Laser desorption mass spectrometer" refers to a mass spectrometer that uses laser energy as a means to desorb, volatilize, and ionize an analyte.

"Tandem mass spectrometer" refers to any mass spectrometer that is capable of performing two successive stages of m/z-based discrimination or measurement of ions, including ions in an ion mixture. The phrase includes mass spectrometers having two mass analyzers that are capable of performing two successive stages of m/z-based discrimination or measurement of ions tandem-in-space. The phrase further includes mass spectrometers having a single mass analyzer that is capable of performing two successive stages of m/z-based discrimination or measurement of ions tandem-in-time. The phrase thus explicitly includes Qq-TOF mass spectrometers, ion trap mass spectrometers, ion trap-TOF mass spectrometers, TOF-TOF mass spectrometers, Fourier transform ion cyclotron resonance mass spectrometers, electrostatic sector—magnetic sector mass spectrometers, and combinations thereof.

"Mass analyzer" refers to a sub-assembly of a mass spectrometer that comprises means for measuring a parameter that can be translated into mass-to-charge ratios of gas phase ions. In a time-of-flight mass spectrometer the mass analyzer comprises an ion optic assembly, a flight tube and an ion detector.

"Ion source" refers to a sub-assembly of a gas phase ion spectrometer that provides gas phase ions. In one embodiment, the ion source provides ions through a desorption/ionization process. Such embodiments generally comprise a probe interface that positionally engages a probe in an interrogatable relationship to a source of ionizing energy (e.g., a laser desorption/ionization source) and in concurrent communication at atmospheric or subatmospheric pressure with a detector of a gas phase ion spectrometer.

Forms of ionizing energy for desorbing/ionizing an analyte from a solid phase include, for example: (1) laser energy; (2) fast atoms (used in fast atom bombardment); (3) high energy particles generated via beta decay of radionucleides (used in plasma desorption); and (4) primary ions generating secondary ions (used in secondary ion mass spectrometry). The preferred form of ionizing energy for solid phase analytes is a laser (used in laser desorption/ionization), in particular, nitrogen lasers, Nd-Yag lasers and other pulsed laser sources. "Fluence" refers to the energy delivered per unit area of interrogated image. A high fluence source, such as a laser, will deliver about 1 mJ/mm2 to 50 mJ/mm2. Typically, a sample is placed on the surface of a probe, the probe is engaged with the probe interface and the probe surface is struck with the ionizing energy. The energy desorbs analyte molecules from the surface into the gas phase and ionizes them.

Other forms of ionizing energy for analytes include, for example: (1) electrons that ionize gas phase neutrals; (2) strong electric field to induce ionization from gas phase, solid phase, or liquid phase neutrals; and (3) a source that applies a combination of ionization particles or electric fields with neutral chemicals to induce chemical ionization of solid phase, gas phase, and liquid phase neutrals.

"Solid support" refers to a solid material which can be derivatized with, or otherwise attached to, a capture reagent. Exemplary solid supports include probes, microtiter plates and chromatographic resins.

"Probe" in the context of this invention refers to a device adapted to engage a probe interface of a gas phase ion spectrometer (e.g., a mass spectrometer) and to present an analyte to ionizing energy for ionization and introduction into a gas phase ion spectrometer, such as a mass spectrometer. A "probe" will generally comprise a solid substrate (either flexible or rigid) comprising a sample presenting surface on which an analyte is presented to the source of ionizing energy.

"Surface-enhanced laser desorption/ionization" or "SELDI" refers to a method of desorption/ionization gas phase ion spectrometry (e.g., mass spectrometry) in which the analyte is captured on the surface of a SELDI probe that engages the probe interface of the gas phase ion spectrometer. In "SELDI MS," the gas phase ion spectrometer is a mass spectrometer. SELDI technology is described in, e.g., U.S. Pat. No. 5,719,060 (Hutchens and Yip) and U.S. Pat. No. 6,225,047 (Hutchens and Yip).

"Surface-Enhanced Affinity Capture" or "SEAC" is a version of SELDI that involves the use of probes comprising an absorbent surface (a "SEAC probe"). "Adsorbent surface" refers to a surface to which is bound an adsorbent (also called a "capture reagent" or an "affinity reagent"). An adsorbent is any material capable of binding an analyte (e.g., a target polypeptide or nucleic acid). "Chromatographic adsorbent" refers to a material typically used in chromatography. Chromatographic adsorbents include, for example, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents). "Biospecific adsorbent" refers an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047 (Hutchens and Yip, "Use of retentate chromatography to generate difference maps," May 1, 2001).

In some embodiments, a SEAC probe is provided as a pre-activated surface which can be modified to provide an adsorbent of choice. For example, certain probes are provided with a reactive moiety that is capable of binding a biological molecule through a covalent bond. Epoxide and carbodiimidizole are useful reactive moieties to covalently bind biospecific adsorbents such as antibodies or cellular receptors.

"Adsorption" refers to detectable non-covalent binding of an analyte to an adsorbent or capture reagent.

"Surface-Enhanced Neat Desorption" or "SEND" is a version of SELDI that involves the use of probes comprising energy absorbing molecules chemically bound to the probe surface. ("SEND probe.") "Energy absorbing molecules" ("EAM") refer to molecules that are capable of absorbing energy from a laser desorption/ionization source and thereafter contributing to desorption and ionization of analyte molecules in contact therewith. The phrase includes molecules used in MALDI, frequently referred to as "matrix", and explicitly includes cinnamic acid derivatives, sinapinic acid ("SPA"), cyano-hydroxy-cinnamic acid ("CHCA") and dihydroxybenzoic acid, ferulic acid, hydroxyacetophenone derivatives, as well as others. It also includes EAMs used in SELDI. SEND is further described in U.S. Pat. No. 5,719,060 and U.S. patent application 60/408,255, filed Sep. 4, 2002 (Kitagawa, "Monomers And Polymers Having Energy Absorbing Moieties Of Use In Desorption/Ionization Of Analytes").

"Surface-Enhanced Photolabile Attachment and Release" or "SEPAR" is a version of SELDI that involves the use of probes having moieties attached to the surface that can covalently bind an analyte, and then release the analyte through breaking a photolabile bond in the moiety after exposure to light, e.g., laser light. SEPAR is further described in U.S. Pat. No. 5,719,060.

"Eluant" or "wash solution" refers to an agent, typically a solution, which is used to affect or modify adsorption of an analyte to an adsorbent surface and/or remove unbound materials from the surface. The elution characteristics of an eluant can depend, for example, on pH, ionic strength, hydrophobicity, degree of chaotropism, detergent strength and temperature.

"Analyte" refers to any component of a sample that is desired to be detected. The term can refer to a single component or a plurality of components in the sample.

The "complexity" of a sample adsorbed to an adsorption surface of an affinity capture probe means the number of different protein species that are adsorbed.

"Molecular binding partners" and "specific binding partners" refer to pairs of molecules, typically pairs of biomolecules that exhibit specific binding. Molecular binding partners include, without limitation, receptor and ligand, antibody and antigen, biotin and avidin, and biotin and streptavidin.

"Monitoring" refers to recording changes in a continuously varying parameter.

"Biochip" refers to a solid substrate having a generally planar surface to which an adsorbent is attached. Frequently, the surface of the biochip comprises a plurality of addressable locations, each of which location has the adsorbent bound there. Biochips can be adapted to engage a probe interface and, therefore, function as probes.

"Protein biochip" refers to a biochip adapted for the capture of polypeptides. Many protein biochips are described in the art. These include, for example, protein biochips produced by Ciphergen Biosystems (Fremont, Calif.), Packard BioScience Company (Meriden Conn.), Zyomyx (Hayward, Calif.) and Phylos (Lexington, Mass.). Examples of such protein biochips are described in the following patents or patent applications: U.S. Pat. No. 6,225,047 (Hutchens and Yip, "Use of retentate chromatography to generate difference maps," May 1, 2001); International publication WO 99/51773 (Kuimelis and Wagner, "Addressable protein arrays," Oct. 14, 1999); U.S. Pat. No. 6,329,209 (Wagner et al., "Arrays of protein-capture agents and methods of use thereof," Dec. 11, 2001) and International publication WO 00/56934 (Englert et al., "Continuous porous matrix arrays," Sep. 28, 2000).

Protein biochips produced by Ciphergen Biosystems comprise surfaces having chromatographic or biospecific adsorbents attached thereto at addressable locations. Ciphergen ProteinChip® arrays include NP20, H4, H50, SAX-2, WCX-2, CM-10, IMAC-3, IMAC-30, LSAX-30, LWCX-30, IMAC-40, PS-10, PS-20 and PG-20. These protein biochips comprise an aluminum substrate in the form of a strip. The surface of the strip is coated with silicon dioxide.

In the case of the NP-20 biochip, silicon oxide functions as a hydrophilic adsorbent to capture hydrophilic proteins.

H4, H50, SAX-2, Q-10, WCX-2, CM-10, IMAC-3, IMAC-30, PS-10 and PS-20 biochips further comprise a functionalized, cross-linked polymer in the form of a hydrogel physically attached to the surface of the biochip or covalently attached through a silane to the surface of the biochip. The H4 biochip has isopropyl functionalities for hydrophobic binding. The H50 biochip has nonylphenoxy-poly(ethylene glycol)methacrylate for hydrophobic binding. The SAX-2 biochip has quaternary ammonium functionalities for anion exchange. The WCX-2 and CM-10 biochips have carboxylate functionalities for cation exchange. The IMAC-3 and IMAC-30 biochips have nitriloacetic acid functionalities that adsorb transition metal ions, such as $Cu^{++}$ and $Ni^{++}$, by chelation. These immobilized metal ions allow adsorption of peptide and proteins by coordinate bonding. The PS-10 biochip has carboimidizole functional groups that can react with groups on proteins for covalent binding. The PS-20 biochip has epoxide functional groups for covalent binding with proteins. The PS-series biochips are useful for binding biospecific adsorbents, such as antibodies, receptors, lectins, heparin, Protein A, biotin/streptavidin and the like, to chip surfaces where they function to specifically capture analytes from a sample. The PG-20 biochip is a PS-20 chip to which Protein G is attached. The LSAX-30 (anion exchange), LWCX-30 (cation exchange) and IMAC-40 (metal chelate) biochips have functionalized latex beads on their surfaces. Such biochips are further described in: WO 00/66265 (Rich et al., "Probes for a Gas Phase Ion Spectrometer," Nov. 9, 2000); WO 00/67293 (Beecher et al., "Sample Holder with Hydrophobic Coating for Gas Phase Mass Spectrometer," Nov. 9, 2000); U.S. patent application US20030032043A1 (Pohl and Papanu, "Latex Based Adsorbent Chip," Jul. 16, 2002) and U.S. patent application 60/350,110 (Um et al., "Hydrophobic Surface Chip," Nov. 8, 2001).

Upon capture on a biochip, analytes can be detected by a variety of detection methods selected from, for example, a gas phase ion spectrometry method, an optical method, an electrochemical method, atomic force microscopy and a radio frequency method. Gas phase ion spectrometry methods are described herein. Of particular interest is the use of mass spectrometry and, in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

The term "measuring" means methods which include detecting the presence or absence of marker(s) in the sample, quantifying the amount of marker(s) in the sample, and/or qualifying the type of biomarker. Measuring can be accomplished by methods known in the art and those further described herein, including but not limited to SELDI and immunoassay. Any suitable methods can be used to detect and measure one or more of the markers described herein. These methods include, without limitation, mass spectrometry (e.g., laser desorption/ionization mass spectrometry), fluorescence (e.g. sandwich immunoassay), surface plasmon resonance, ellipsometry and atomic force microscopy.

The phrase "differentially present" refers to differences in the quantity and/or the frequency of a marker present in a sample taken from patients having human cancer as compared to a control subject. For example, the IAIH4 fragments are present at an elevated level in samples of ovarian cancer patients compared to samples from control subjects. In contrast, Apo A1 and transthyretin described herein are present at a decreased level in samples of ovarian cancer patients compared to samples from control subjects. Furthermore, a marker can be a polypeptide, which is detected at a higher frequency or at a lower frequency in samples of human cancer patients compared to samples of control subjects. A marker can be differentially present in terms of quantity, frequency or both.

A polypeptide is differentially present between two samples if the amount of the polypeptide in one sample is statistically significantly different from the amount of the polypeptide in the other sample. For example, a polypeptide is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polypeptide is differentially present between two sets of samples if the frequency of detecting the polypeptide in the ovarian cancer patients' samples is statistically significantly higher or lower than in the control samples. For example, a polypeptide is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

"Diagnostic" means identifying the presence or nature of a pathologic condition, i.e., ovarian cancer. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "test amount" of a marker refers to an amount of a marker present in a sample being tested. A test amount can be either in absolute amount (e.g., µg/ml) or a relative amount (e.g., relative intensity of signals).

A "diagnostic amount" of a marker refers to an amount of a marker in a subject's sample that is consistent with a diagnosis of ovarian cancer. A diagnostic amount can be either in absolute amount (e.g., µg/ml) or a relative amount (e.g., relative intensity of signals).

A "control amount" of a marker can be any amount or a range of amount, which is to be compared against a test amount of a marker. For example, a control amount of a marker can be the amount of a marker in a person without ovarian cancer. A control amount can be either in absolute amount (e.g., µg/ml) or a relative amount (e.g., relative intensity of signals).

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well-characterized fragments produced by digestion with various peptidases. This includes, e.g., Fab' and F(ab')$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

"Managing subject treatment" refers to the behavior of the clinician or physician subsequent to the determination of ovarian cancer status. For example, if the result of the methods of the present invention is inconclusive or there is reason that confirmation of status is necessary, the physician may order more tests. Alternatively, if the status indicates that surgery is appropriate, the physician may schedule the patient for surgery. Likewise, if the status is negative, e.g., late stage ovarian cancer or if the status is acute, no further action may be warranted. Furthermore, if the results show that treatment has been successful, no further management may be necessary.

DETAILED DESCRIPTION OF THE INVENTION

The present invention provides biomarkers generated from comparison of protein profiles from patients diagnosed with ovarian cancer and from patients without known neoplastic diseases, using the ProteinChip® Biomarker System (Ciphergen Biosystems, Inc., Fremont, Calif.). These biomarkers, together with other known ovarian cancer markers, were evaluated individually and in multivariate predictive models. In particular, it is shown that these biomarkers, used individually, or preferably in combination with other biomarkers from this group or with other diagnostic tests, provide a novel method of determining ovarian cancer status in a subject.

High-throughput protein profiling combined with effective use of bioinformatics tools provides a useful approach to screening for cancer markers. Briefly, the system used in the present invention utilizes chromatographic ProteinChip® Arrays to assay samples using SELDI (Surface Enhanced Laser Desorption/Ionization). Proteins bound to the arrays are read in a ProteinChip® Reader, a time-of-flight mass spectrometer.

A biomarker (also referred to herein as a "marker") is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. Therefore, they are useful as markers for disease (diagnostics), therapeutic effectiveness of a drug (theranostics) and drug toxicity.

The present invention is based upon the discovery of protein markers that are differentially present in samples of ovarian cancer patients and control subjects, and the application of this discovery in methods and kits for determining ovarian cancer status. These protein markers are found in samples from ovarian cancer patients at levels that are different than the levels in samples from women in whom human cancer is undetectable. Accordingly, the amount of one or more markers found in a test sample compared to a control, or the presence or absence of one or more markers in the test sample provides useful information regarding the ovarian cancer status of the patient.

I. Description of the Biomarkers

A. Apolipoprotein A1

One example of a marker that is useful in the methods of the present invention includes apolipoprotein A1, also referred to herein as "Apo A1". Apo A1 is detectable by mass spectrometry as a peak having m/z of 28043 (Marker XXIV). The masses for the markers described herein are considered accurate to within 0.15 percent of the specified value as determined by the disclosed SELDI-mass spectroscopy protocol. Accordingly, Apo A1 may also be detectable as a peak having m/z of 28055.

Apo A1 was detected by fractionating blood according to protocol, followed by application to an IMAC chip and detection by SELDI. The purified protein was digested with trypsin and identified as apolipoprotein A1. The protocol for isolating and identifying Apo A1 is set forth below in the Examples. Apo A1 is down regulated in patients that have ovarian cancer at some stage. Thus, the absence of Apo A1, or a statistically significant decrease in the amount of Apo A1, as compared with a normal control, would be correlated with an ovarian cancer status. A statistically significant decrease is that which is known in the art, e.g., p value less than 0.05.

Preferred methods of the present invention include the use of modified forms of Apo A1. Modification of Apo A1 may include the post-translational addition of various chemical groups, for example, glycosylation, lipidation, cysteinylation, and glutathionylation.

Figure 15:
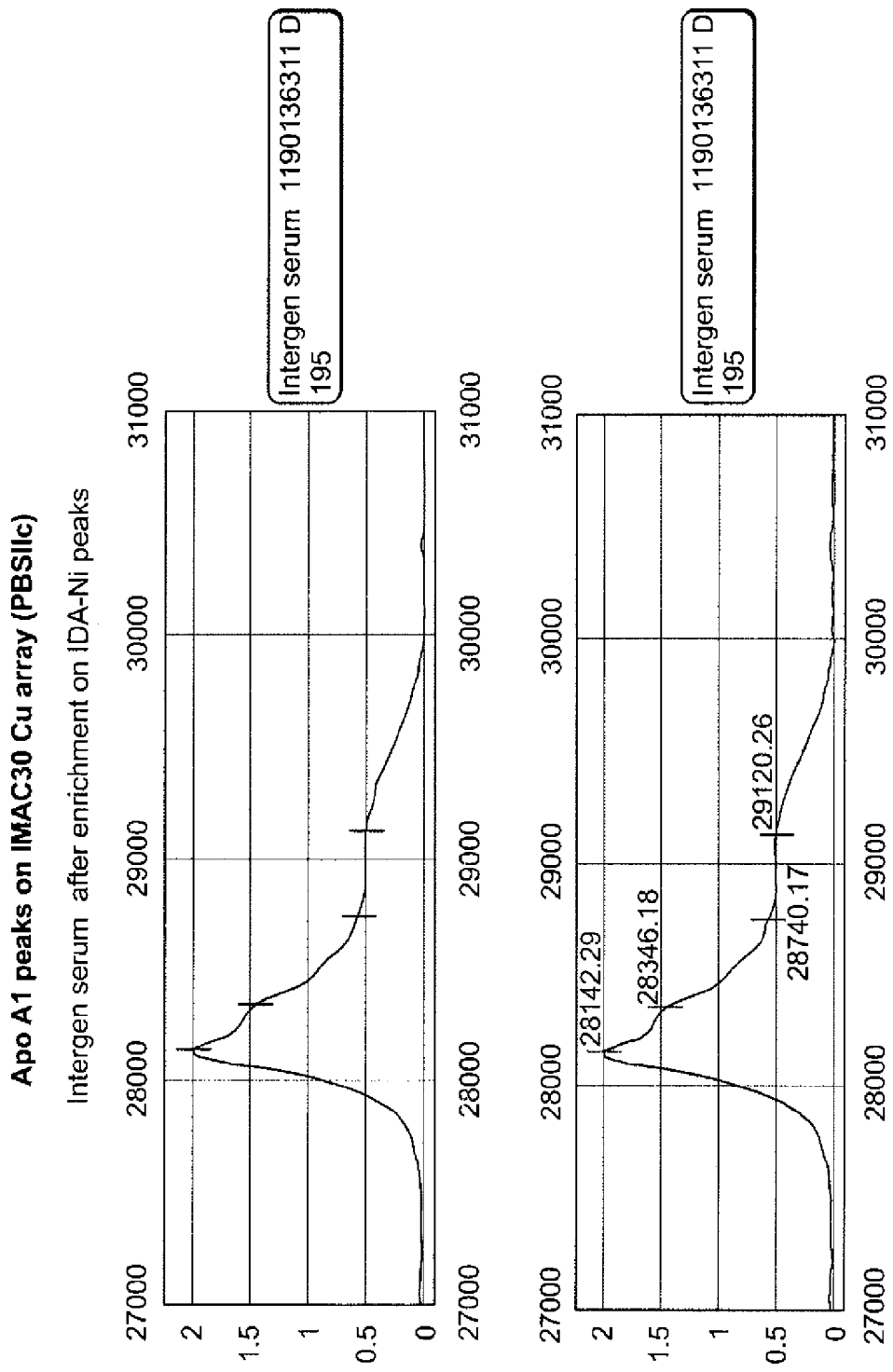
FIG. 15 shows mass spectra for Apo A1 peaks on an IMAC30 Cu array (PBSIIc).
Figure 16:
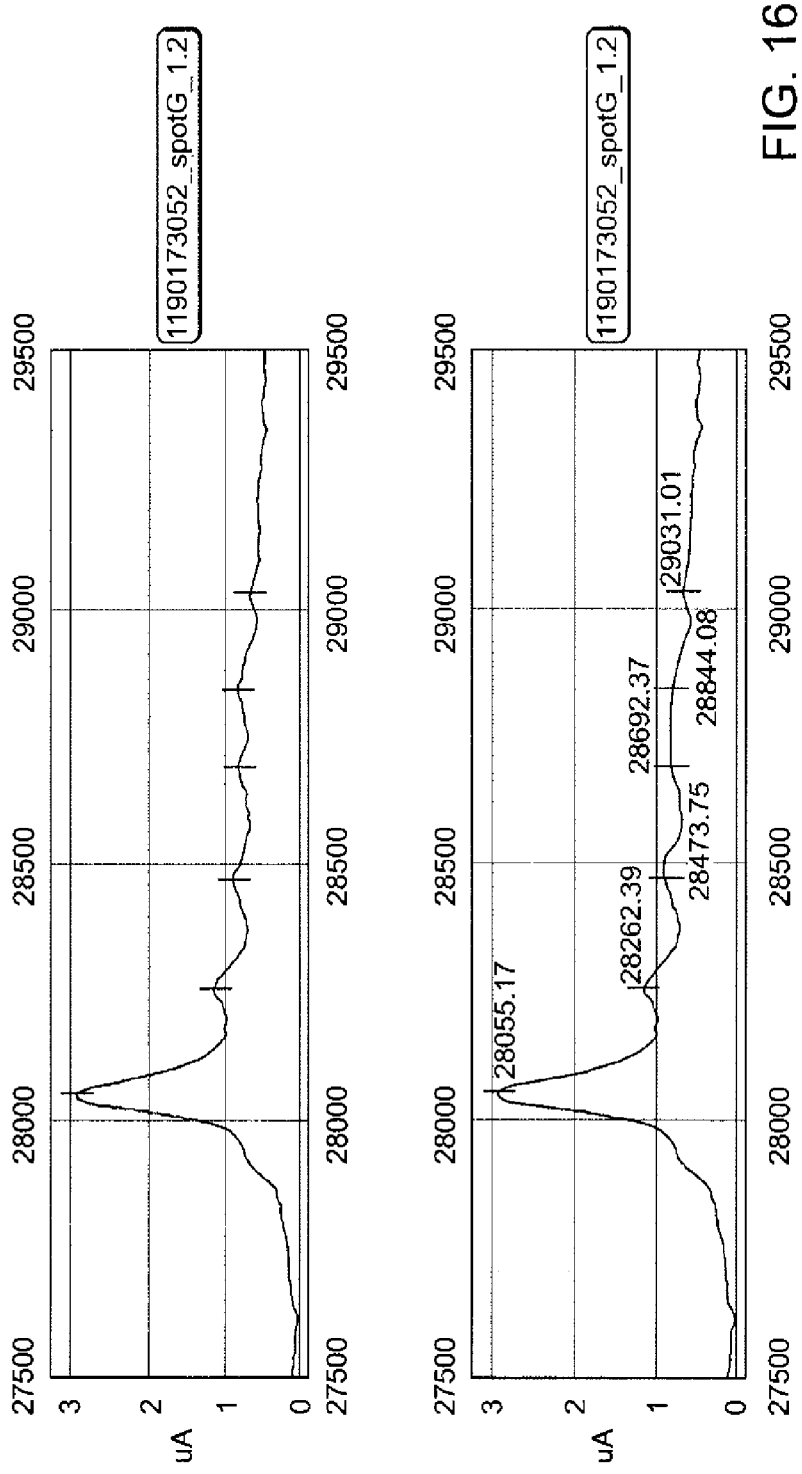
FIG. 16 shows mass spectra for Apo A1 peaks on an IMAC30 Cu array (PBS4000).

A particularly preferred example of modified Apo A1 is the peak having m/z of 29977.4 (Marker XXV). This modified Apo A1 peak appears as a shoulder on the ApoA1 mass spectrometry peak described above. Other preferred modified Apo A1 forms are the peaks having m/z of 28262, 28473, 28692, 28844, and 29031. FIGS. 15 and 16 show mass spectra indicating the peak positions of the modified Apo A1 biomarkers.

B. Transthyretin

Another example of a marker that is useful in the methods of the present invention includes a form of pre-albumin, also referred to herein as "transthyretin ΔN10". Transthyretin ΔN10 is detectable by mass spectrometry as a peak having m/z of 12870.9. Transthyretin ΔN10 was detected by fractionating blood according to protocol, followed by application to an IMAC chip and detection by SELDI. By immunoprecipitation and tandem mass spectrometry, the purified protein was found to be a truncated form of pre-albumin, lacking the N-terminal ten amino acids (referred to herein as "transthyretin ΔN10"). The protocol for isolating and identifying transthyretin ΔN10 is set forth below in the Examples. Transthyretin ΔN10 is also down regulated in patients that have ovarian cancer at some stage. Thus, the absence of transthyretin ΔN10, or a statistically significant decrease in the amount of transthyretin ΔN10, as compared with a normal control, would be correlated with an ovarian cancer status.

The invention is described herein as using transthyretin ΔN10. However, the native transthyretin (theoretical mass of 13,761 or 13767 daltons) is also useful in the methods of the invention. Additionally, preferred methods of the present invention include the use of modified forms of transthyretin. Modification of transthyretin may include the post-translational addition of various chemical groups, for example, glycosylation, lipidation, cysteinylation, sulfonation, CysGly modification, and glutathionylation.

Figure 8:
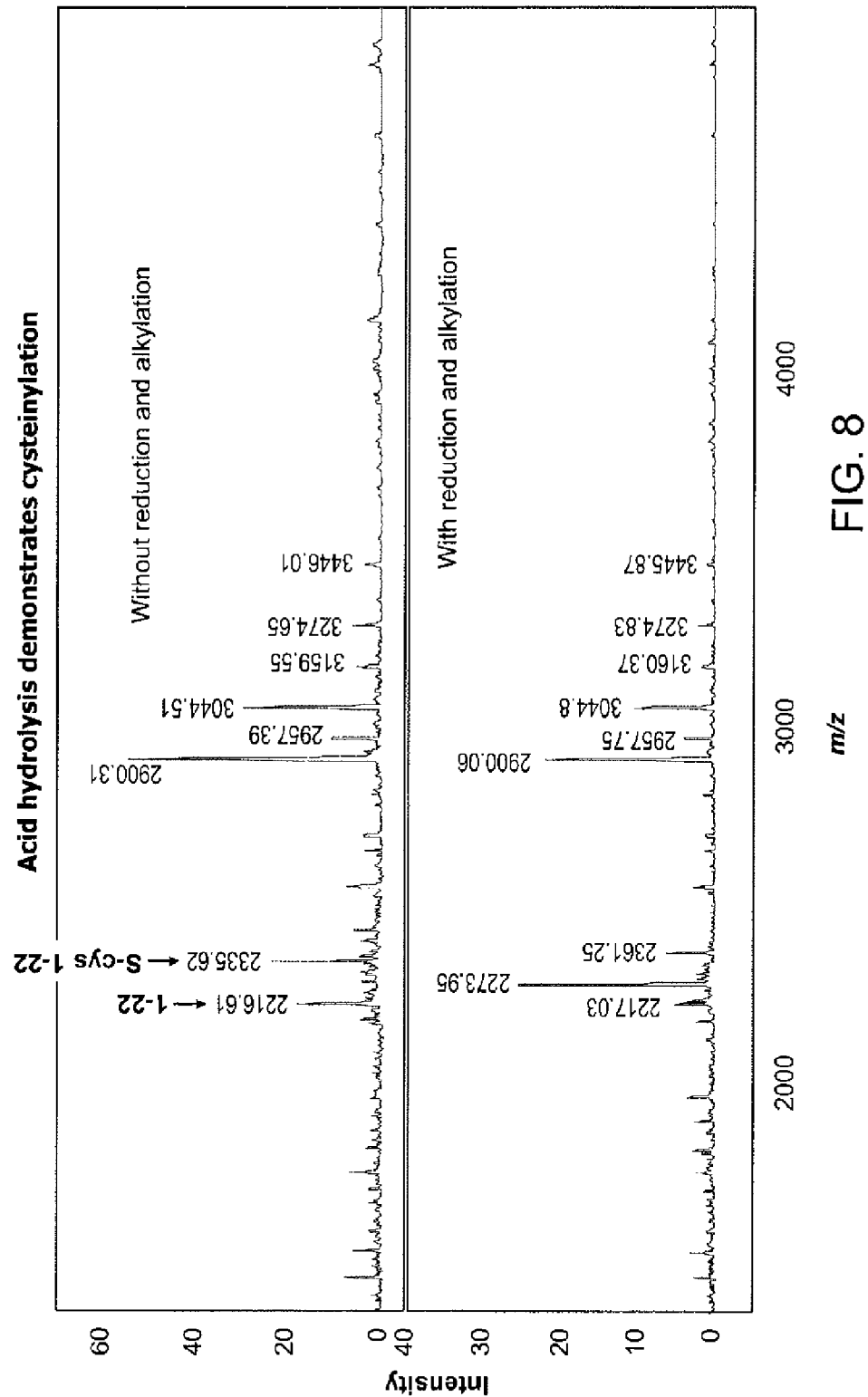
FIG. 8 shows the change in mass spectra peak pattern after reduction and alkylation, demonstrating the cysteinylation of transthyretin.

A particularly preferred example of modified transthyretin is cysteinylated transthyrtein (the peak having m/z of 13,890.8 or 13888 daltons). FIG. 8 shows the change in peak pattern after reduction and alkylation, demonstrating the cysteinylation of transthyretin. Another preferred example of modified transthyretin is glutathionylated transthyretin (the peak having m/z of 14,086.9 or 14093 daltons). Another preferred example of modified transthyretin is sulfonated transthyretin (the peak having m/z of 13850 daltons). Still another preferred example of modified transthyretin is Cys-Gly modified transthyretin (the peak having m/z of 13944 daltons).

Figure 6:
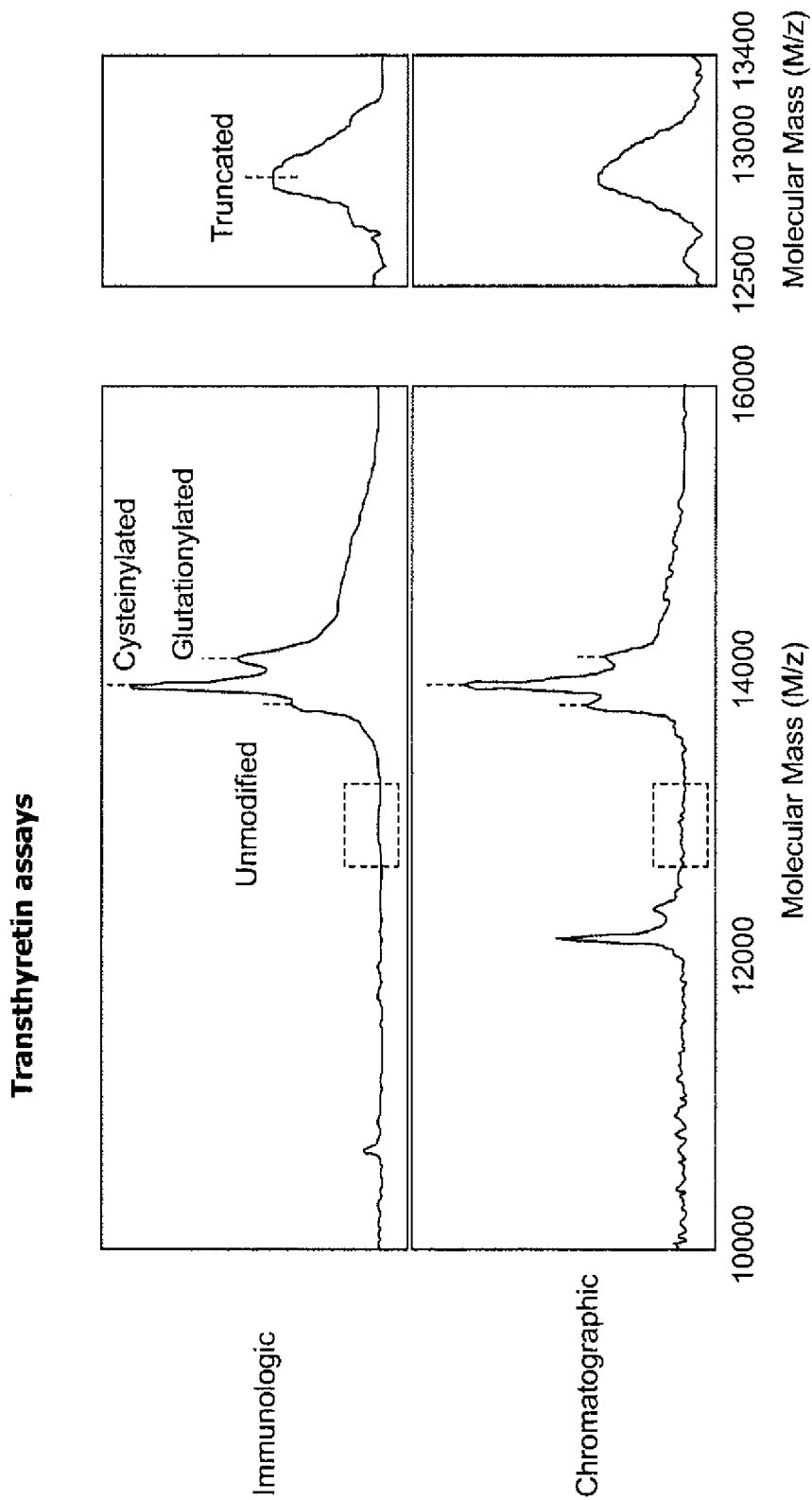
FIG. 6 shows mass spectra for immunologic and chromotographic detection of unmodified, cysteinlyated, glutathionylated, and truncated forms of transthyretin.
Figure 7A:
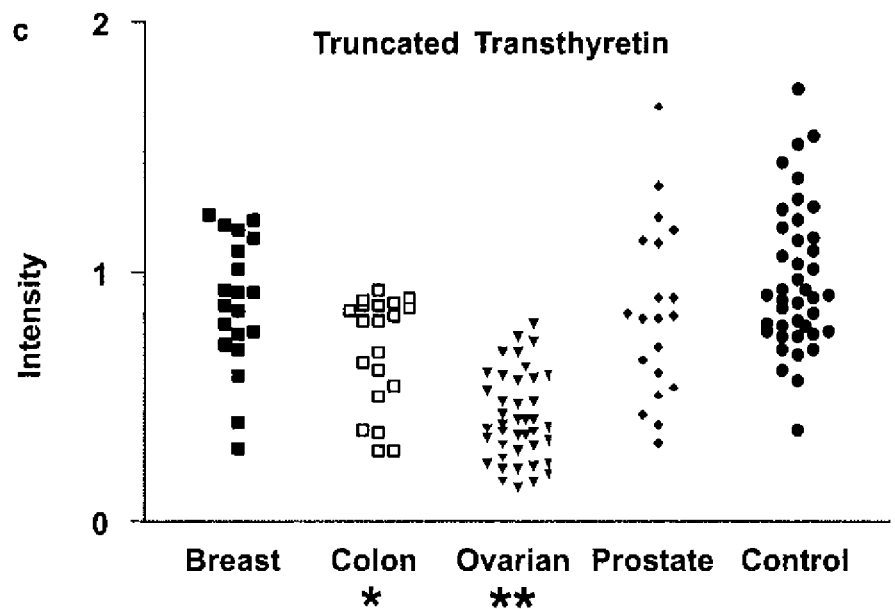
FIG. 7 shows the results of detection of various forms of transthretin in patients with ovarian cancer, as compared to other cancers and to control patients.
Figure 7B:
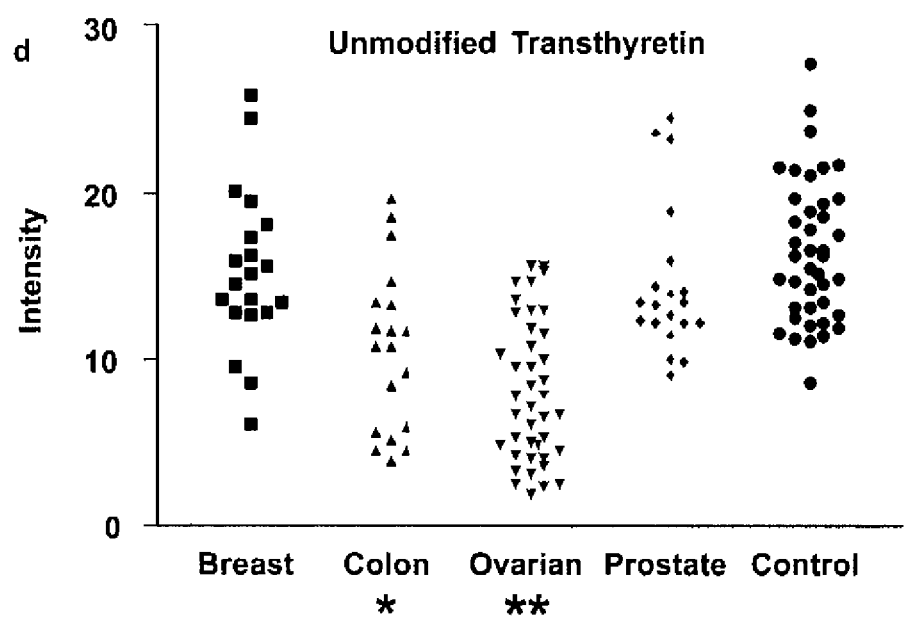
Figure 7C:
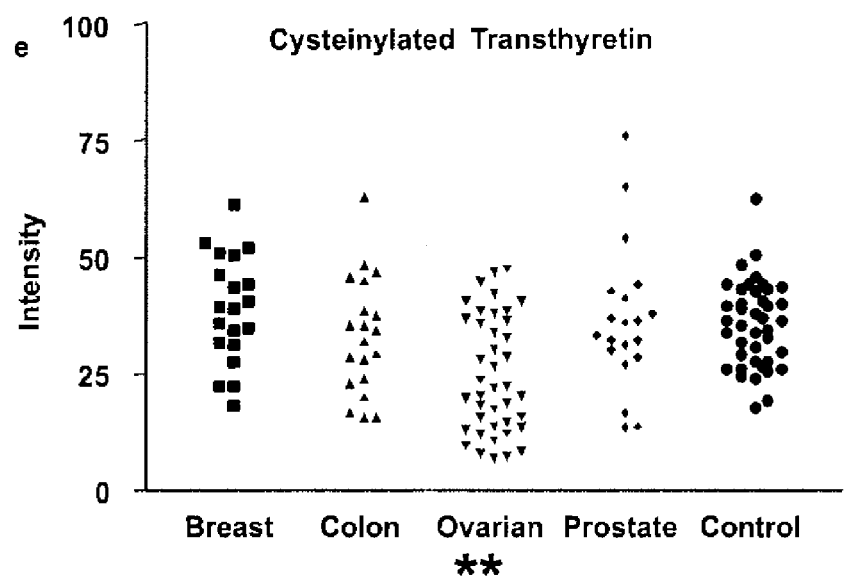
Figure 7D:
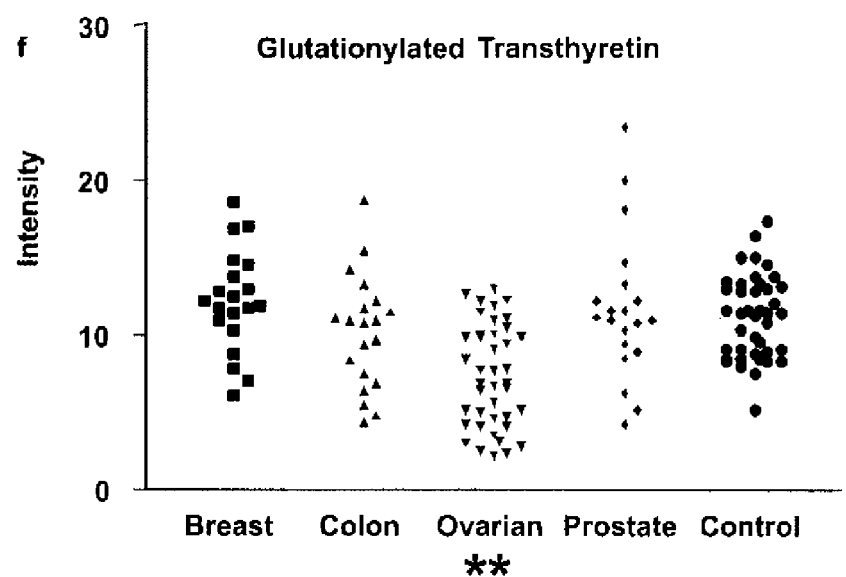

FIG. 6 shows the relative sizes of truncated (transthyretin ΔN10), unmodified, cysteinylated, and glutathionylated transthyretin. As shown in FIG. 7, truncated transthyretin (transthyretin ΔN10), unmodified (native) transthyretin, cysteinylated transthyretin, and glutathionylated transthyretin are all lower (p<0.001) in patients with ovarian cancer, as compared to other cancers and non-cancer controls.

C. IAIH4 Fragment

Another example of a marker that is useful in the methods of the present invention is a cleavage fragment of inter-α-trypsin inhibitor heavy chain H4, also referred to alternatively herein as "IAIH4 fragment", "ITIH4 fragment", and/or PK-120 fragment. In a preferred embodiment, an IAIH4 fragment is selected from the group consisting of IAIH4 fragment no. 1, IAIH4 fragment no. 2, and IAIH4 fragment no. 3. In a further preferred embodiment, the generic term "IAIH4 fragment" includes any one of IAIH4 fragment no. 1, IAIH4 fragment no. 2, and IAIH4 fragment no. 3.

IAIH4 fragment no. 1 is detectable by mass spectrometry as a peak having m/z of 3272. IAIH4 fragment no. 1 was detected by fractionating blood according to protocol, followed by application to an IMAC chip and detection by SELDI. The peak was purified from the pooled serum of ovarian cancer patients using a series of chromatography separation techniques. Its sequence was determined to be MNFRPGVLSSRQLGLPGPPDVPDHAAYHPF (SEQ ID NO:1), a fragment spanning amino acids 660-689 of human Inter-alpha trypsin inhibitor, heavy chain H4 (also referred to as IAIH4, ITIH4, or PK-120). This result was confirmed by the analysis of pepsin digestion products of the marker. IAIH4 fragment no. 1 is up regulated in patients that have ovarian cancer at some stage. Thus, the presence of IAIH4 fragment no. 1, or an increase in the amount of IAIH4 fragment no. 1, as compared with a normal control, would be correlated with an ovarian cancer status.

Figure 5:
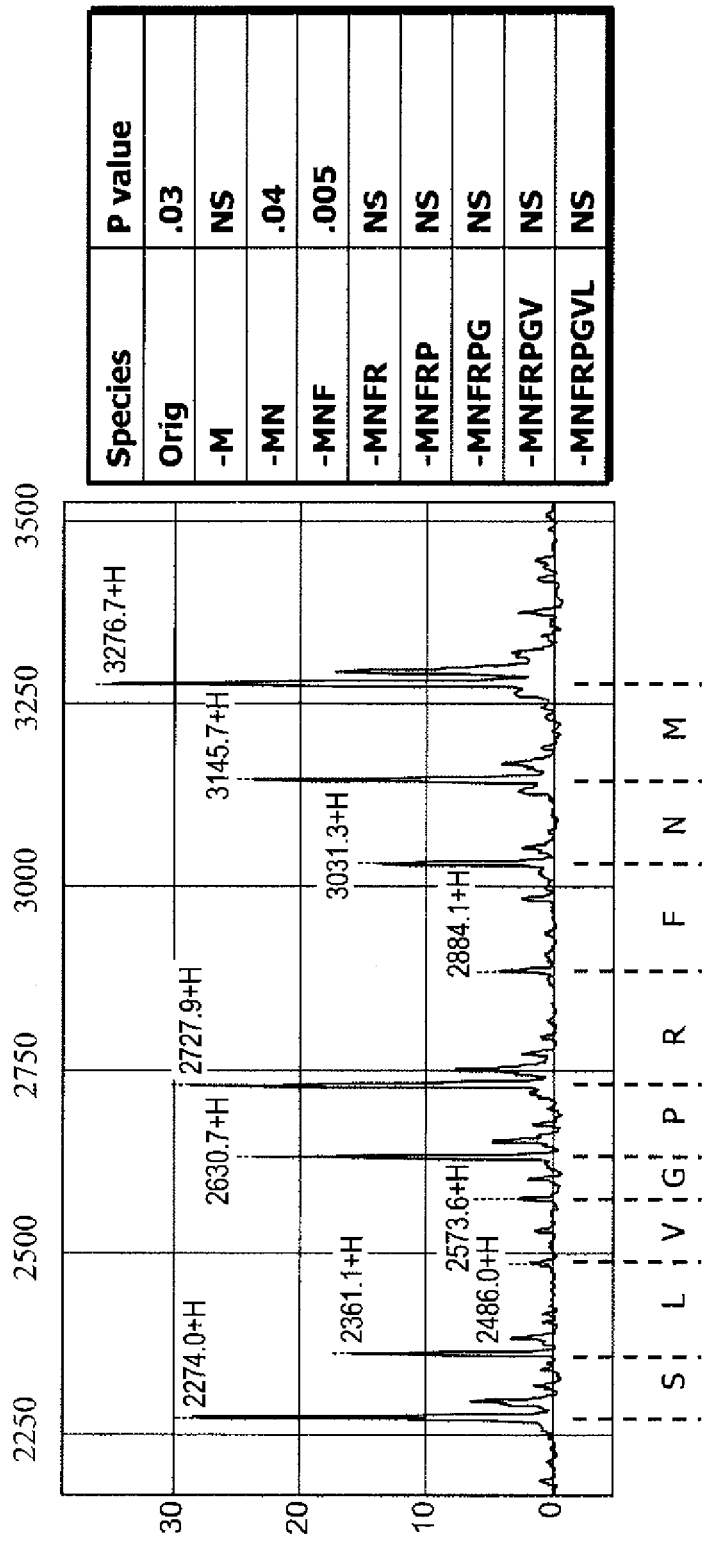
FIG. 5 shows spectrum of different fragments of IAIH4 found in ovarian cancer samples. Peak 3276.7 represents IAIH4 fragment no. 1 (SEQ ID NO:1). Peak 3031.3 represents IAIH4 fragment no. 2 (SEQ ID NO:2). Peak 2884 represents IAIH4 fragment no. 3 (IAIH4 fragment no. 3). The table shows the p value for the presence of eight truncations of the original IAIH4 fragment (IAIH4 fragment no. 1; "Orig") in ovarian cancer versus non-cancerous samples. NS=not significant. "-MN" represents a truncation of the N-terminal M and N from the IAIH4 fragment no. 1 sequence, and is also set forth as SEQ ID NO:2 (IAIH4 fragment no. 2). "-MNF" represents a truncation of the N-terminal M, N, and F from the IAIH4 fragment no. 1 sequence, and is also set forth as SEQ ID NO:3 (IAIH4 fragment no. 3). The remaining fragments in the table have the indicated amino acid residues removed from the original IAIH4 fragment no. 1 sequence.

A SELDI immunoassay using an antibody to IAIH4 was used to identify further IAIH4 fragments that are upregulated in ovarian cancer at some stage. Several such fragments were identified, two of which showed statistically significant differences between ovarian cancer and non-ovarian cancer (See FIG. 5). The sequence of IAIH4 fragment no. 2 was determined to be FRPGVLSSRQLGLPGPPDVPDHAAYHPF (SEQ ID NO:2), which comprises all but the first two amino acid residues of IAIH4 fragment no. 1. IAIH4 fragment no. 2 is detectable by mass spectrometry as a peak having m/z of 3031. The sequence of IAIH4 fragment no. 3 was determined to be RPGVLSSRQLGLPGPPDVPDHAAYHPF (SEQ ID NO:3), which comprises all but the first three amino acid residues of IAIH4 fragment no. 1. IAIH4 fragment no. 3 is detectable by mass spectrometry as a peak having m/z of 2884. As with IAIH4 fragment no. 1, IAIH4 fragment nos. 1 and 2 are up regulated in patients that have ovarian cancer at some stage. Thus, the presence of IAIH4 fragment nos. 1 or 2, or an increase in the amount of IAIH4 fragment nos. 1 or 2, as compared with a normal control, would be correlated with an ovarian cancer status.

Additionally, preferred methods of the present invention include the use of modified forms of IAIH4 fragment. Modification of IAIH4 fragment may include the post-translational addition of various chemical groups, for example, glycosylation, lipidation, cysteinylation, and glutathionylation.

E. Other Discovered Ovarian Cancer Markers

Additional biomarkers were also identified in the fractions eluted at pH 4 and pH 9 that are associated with ovarian cancer disease status. At pH 4, the corresponding proteins or fragments of proteins for these biomarkers are represented as intensity peaks in SELDI (surface enhanced laser desorption/ionization) protein chip/mass spectra with molecular masses centered around the following values:

| Data Set 1 | |
| --- | --- |
| MARKER NO. | MASS (Daltons) |
| I | M4484.92 |
| II | M10065.9 |
| III | M9311.27 |
| IV | M27773.4 |
| V | M10668.3 |
| VI | M6953.19 |
| VII | M12870.9 |
| VIII | M13891.9 |
| IX | M7566.22 |
| X | M3339.22 |
| XI | M13596.8 |
| XII | M7769.93 |
| XIII | M14069.7 |
| XIV | M14338.7 |
| XV | M4499.12 |
| XVI | M6678.07 |
| XVII | M8144.60 |

| Data Set 2 | |
| --- | --- |
| MARKER NO. | MASS (Daltons) |
| XVIII | M11699.9 |
| XIX | M2729.15 |
| XX | M8949.37 |
| XXI | M30113.3 |
| XXII | M10668.3 |
| XXIII | M3379.43 |
| XXIV | M27288.8 |
| XXV | M29977.4 |
| XXVI | M1048.88 |
| XXVII | M39847.3 |
| XXVIII | M5607.28 |
| XXIX | M3822.84 |
| XXX | M29822.5 |
| XXXI | M41561.8 |
| XXXII | M4128.4 |
| XXXIII | M2340.70 |

At pH 9, the corresponding proteins or fragments of proteins for these biomarkers are represented as intensity peaks in SELDI (surface enhanced laser desorption/ionization) protein chip/mass spectra with molecular masses centered around the following values:

| Data Set 3 | |
| --- | --- |
| MARKER NO. | MASS (Daltons) |
| XXXIV | M2748.46 |
| XXXV | M2866.33 |
| XXXVI | M2916.45 |
| XXXVII | M3033.86 |
| XXXVIII | M3193.54 |
| XXXIX | M3277.75 |
| XL | M3291.72 |
| XLI | M3307.35 |
| XLII | M4071.20 |
| XLIII | M4342.23 |
| XLIV | M5986.74 |
| XLV | M6023.61 |
| XLVI | M6308.55 |
| XLVII | M8132.55 |
| XLVIII | M8527.75 |

These masses for Markers I through XLVIII are considered accurate to within 0.15 percent of the specified value as determined by the disclosed SELDI-mass spectroscopy protocol.

As discussed above, Markers I through XLVIII also may be characterized based on affinity for an adsorbent, particularly binding to an immobilized chelate (IMAC)-Cu substrate surface under the conditions specified under ProteinChip Analysis of the General Comments of the Examples, which follow.

E. Known Ovarian Cancer Markers

Certain embodiments of the present invention also use known ovarian cancer biomarkers in combination with one of more of the markers selected from Apo A1, transthyretin ΔN10, IAIH4 fragment no. 1, IAIH4 fragment no. 2, and IAIH4 fragment no. 3. The term "Marker 4" is used herein to refer to known ovarian cancer markers. Examples of markers that are useful as Marker 4 include, but are not limited to, CA125, CA125 II, CA15-3, CA19-9, CA72-4, CA195, TATI, CEA, PLAP, Sialyl TN, galactosyltransferase, M-CSF, CSF-1, LPA, p110EGFR, tissue kallikreins, prostasin, HE4, CKB, LASA, HER-2/neu, urinary gonadotropin peptide, Dianon NB 70/K, TPA, osteopontin and haptoglobin, bikunin, MUC1, and protein variants (e.g., cleavage forms, isoforms) of the markers.

These markers are useful in diagnosing ovarian cancer based upon their levels in the blood, compared to normal subjects. For example, CA125 is known to be elevated in the blood of women with ovarian cancer. Similarly, CA19-9, CA 72.4, CA195, TATI, inhibin and PLAP, and others, are known to be elevated in the blood of women with ovarian cancer. In certain preferred embodiments of this invention, at least one known marker (Marker 4) is included in the method with at least one of the markers selected from Apo A1, transthyretin ΔN10 IAIH4 fragment, no. 1, IAIH4 fragment no. 2, and IAIH4 fragment no. 3.

F. Use of Modified Forms of a Biomarker

It has been found that proteins frequently exist in a sample in a plurality of different forms characterized by a detectably different mass. These forms can result from either, or both, of pre- and post-translational modification. Pre-translational modified forms include allelic variants, slice variants and RNA editing forms. Post-translationally modified forms include forms resulting from truncation, proteolytic cleavage (e.g., fragments of a parent protein), glycosylation, lipidation, cysteinylation, glutationylation, phosphorylation, prenylation, acylation, acetylation, methylation, sulfation, sulfonation, hydroxylation, myristoylation, farnesylation, oxidation and ubiqutination. The collection of proteins including a specific protein and all modified forms of it is referred to herein as a "protein cluster." The collection of all modified forms of a specific protein, excluding the specific protein, itself, is referred to herein as a "modified protein cluster." Modified forms of any biomarker of this invention also may be used, themselves, as biomarkers. In certain cases the modified forms may exhibit better discriminatory power in diagnosis than the specific forms set forth herein.

Modified forms of a biomarker can be initially detected by any methodology that can detect and distinguish the modified from the biomarker. A preferred method for initial detection involves first capturing the biomarker and modified forms of it, e.g., with biospecific capture reagents, and then detecting the captured proteins by mass spectrometry. More specifically, the proteins are captured using biospecific capture reagents, such as antibodies, aptamers or Affibodies that recognize the biomarker and modified forms of it. This method also will also result in the capture of protein interactors that are bound to the proteins or that are otherwise recognized by antibodies and that, themselves, can be biomarkers. Preferably, the biospecific capture reagents are bound to a solid phase. Then, the captured proteins can be detected by SELDI mass spectrometry or by eluting the proteins from the capture reagent and detecting the eluted proteins by traditional MALDI or by SELDI. The use of mass spectrometry is especially attractive because it can distinguish and quantify modified forms of a protein based on mass and without the need for labeling.

Preferably, the biospecific capture reagent is bound to a solid phase, such as a bead, a plate, a membrane or a chip. Methods of coupling biomolecules, such as antibodies, to a solid phase are well known in the art. They can employ, for example, bifunctional linking agents, or the solid phase can be derivatized with a reactive group, such as an epoxide or an imidizole, that will bind the molecule on contact. Biospecific capture reagents against different target proteins can be mixed in the same place, or they can be attached to solid phases in different physical or addressable locations. For example, one can load multiple columns with derivatized beads, each column able to capture a single protein cluster. Alternatively, one can pack a single column with different beads derivatized with capture reagents against a variety of protein clusters, thereby capturing all the analytes in a single place. Accordingly, antibody-derivatized bead-based technologies, such as xMAP technology of Luminex (Austin, Tex.) can be used to detect the protein clusters. However, the biospecific capture reagents must be specifically directed toward the members of a cluster in order to differentiate them.

In yet another embodiment, the surfaces of biochips can be derivatized with the capture reagents directed against protein clusters either in the same location or in physically different addressable locations. One advantage of capturing different clusters in different addressable locations is that the analysis becomes simpler.

After identification of modified forms of a protein and correlation with the clinical parameter of interest, the modified form can be used as a biomarker in any of the methods of this invention. At this point, detection of the modified from can be accomplished by any specific detection methodology including affinity capture followed by mass spectrometry, or traditional immunoassay directed specifically the modified form. Immunoassay requires biospecific capture reagents, such as antibodies, to capture the analytes. Furthermore, if the assay must be designed to specifically distinguish protein and modified forms of protein. This can be done, for example, by employing a sandwich assay in which one antibody captures more than one form and second, distinctly labeled antibodies, specifically bind, and provide distinct detection of, the various forms. Antibodies can be produced by immunizing animals with the biomolecules. This invention contemplates traditional immunoassays including, for example, sandwich immunoassays including ELISA or fluorescence-based immunoassays, as well as other enzyme immunoassays.

II. Test Samples

A) Subject Types

Samples are collected from subjects, e.g., women, who want to establish ovarian cancer status. The subjects may be women who have been determined to have a high risk of ovarian cancer based on their family history. Other patients include women who have ovarian cancer and the test is being used to determine the effectiveness of therapy or treatment they are receiving. Also, patients could include healthy women who are having a test as part of a routine examination, or to establish baseline levels of the biomarkers. Samples may be collected from women who had been diagnosed with ovarian cancer and received treatment to eliminate the cancer, or perhaps are in remission.

B) Types of Sample and Preparation of the Sample

The markers can be measured in different types of biological samples. The sample is preferably a biological fluid sample. Examples of a biological fluid sample useful in this invention include blood, blood serum, plasma, vaginal secretions, urine, tears, saliva, etc. Because all of the markers are found in blood serum, blood serum is a preferred sample source for embodiments of the invention.

If desired, the sample can be prepared to enhance detectability of the markers. For example, to increase the detectability of markers, a blood serum sample from the subject can be preferably fractionated by, e.g., Cibacron blue agarose chromatography and single stranded DNA affinity chromatography, anion exchange chromatography, affinity chromatography (e.g., with antibodies) and the like. The method of fractionation depends on the type of detection method used. Any method that enriches for the protein of interest can be used. Sample preparations, such as pre-fractionation protocols, are optional and may not be necessary to enhance detectability of markers depending on the methods of detection used. For example, sample preparation may be unnecessary if antibodies that specifically bind markers are used to detect the presence of markers in a sample.

Typically, sample preparation involves fractionation of the sample and collection of fractions determined to contain the biomarkers. Methods of pre-fractionation include, for example, size exclusion chromatography, ion exchange chromatography, heparin chromatography, affinity chromatography, sequential extraction, gel electrophoresis and liquid chromatography. The analytes also may be modified prior to detection. These methods are useful to simplify the sample for further analysis. For example, it can be useful to remove high abundance proteins, such as albumin, from blood before analysis. Examples of methods of fractionation are described in PCT/US03/00531 (incorporated herein in its entirety).

Preferably, the sample is pre-fractionated by anion exchange chromatography. Anion exchange chromatography allows pre-fractionation of the proteins in a sample roughly according to their charge characteristics. For example, a Q anion-exchange resin can be used (e.g., Q HyperD F, Biosepra), and a sample can be sequentially eluted with eluants having different pH's. Anion exchange chromatography allows separation of biomolecules in a sample that are more negatively charged from other types of biomolecules. Proteins that are eluted with an eluant having a high pH is likely to be weakly negatively charged, and a fraction that is eluted with an eluant having a low pH is likely to be strongly negatively charged. Thus, in addition to reducing complexity of a sample, anion exchange chromatography separates proteins according to their binding characteristics.

In preferred embodiments, the serum samples are fractionated via anion exchange chromatography. Signal suppression of lower abundance proteins by high abundance proteins presents a significant challenge to SELDI mass spectrometry. Fractionation of a sample reduces the complexity of the constituents of each fraction. This method can also be used to attempt to isolate high abundance proteins into a fraction, and thereby reduce its signal suppression effect on lower abundance proteins. Anion exchange fractionation separates proteins by their isoelectric point (pI). Proteins are comprised of amino acids, which are ambivalent-their charge changes based on the pH of the environment to which they are exposed. A protein's pI is the pH at which the protein has no net charge. A protein assumes a neutral charge when the pH of the environment is equivalent to pI of the protein. When the pH rises above the pI of the protein, the protein assumes a net negative charge. Similarly, when the pH of the environment falls below the pI of the protein, the protein has a net positive charge. The serum samples were fractionated according to the protocol set forth in the Examples below to obtain the markers described herein.

After capture on anion exchange, proteins were eluted in a series of step washes at pH 9, pH 7, pH 5, pH 4 and pH 3. A panel of three potential biomarkers was discovered by UMSA analysis of profiling data of three fractions (pH 9/flow through, pH 4, and organic solvent). Two of the peaks were from fraction pH 4 at m/z of 12828 and 28043, both down-regulated in the cancer group, and the third was from fraction pH 9/flow through at m/z of 3272, up-regulated in the cancer group. All bound to the immobilized metal affinity chromatography array charged with copper ions (IMAC3-Cu) (spectra in FIG. 1).

Biomolecules in a sample can also be separated by high-resolution electrophoresis, e.g., one or two-dimensional gel electrophoresis. A fraction containing a marker can be isolated and further analyzed by gas phase ion spectrometry. Preferably, two-dimensional gel electrophoresis is used to generate two-dimensional array of spots of biomolecules, including one or more markers. See, e.g., Jungblut and Thiede, *Mass Spectr. Rev.* 16:145-162 (1997).

The two-dimensional gel electrophoresis can be performed using methods known in the art. See, e.g., Deutscher ed., *Methods In Enzymology vol.* 182. Typically, biomolecules in a sample are separated by, e.g., isoelectric focusing, during which biomolecules in a sample are separated in a pH gradient until they reach a spot where their net charge is zero (i.e., isoelectric point). This first separation step results in one-dimensional array of biomolecules. The biomolecules in one-dimensional array is further separated using a technique generally distinct from that used in the first separation step. For example, in the second dimension, biomolecules separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass of biomolecules. Typically, two-dimensional gel electrophoresis can separate chemically different biomolecules in the molecular mass range from 1000-200,000 Da within complex mixtures. The pI range of these gels is about 3-10 (wide range gels).

Biomolecules in the two-dimensional array can be detected using any suitable methods known in the art. For example, biomolecules in a gel can be labeled or stained (e.g., Coomassie Blue or silver staining). If gel electrophoresis generates spots that correspond to the molecular weight of one or more markers of the invention, the spot can be further analyzed by gas phase ion spectrometry. For example, spots can be excised from the gel and analyzed by gas phase ion spectrometry. Alternatively, the gel containing biomolecules can be transferred to an inert membrane by applying an electric field. Then a spot on the membrane that approximately corresponds to the molecular weight of a marker can be analyzed by gas phase ion spectrometry. In gas phase ion spectrometry, the spots can be analyzed using any suitable techniques, such as MALDI or SELDI (e.g., using ProteinChip® array) as described herein.

Prior to gas phase ion spectrometry analysis, it may be desirable to cleave biomolecules in the spot into smaller fragments using cleaving reagents, such as proteases (e.g., trypsin). The digestion of biomolecules into small fragments provides a mass fingerprint of the biomolecules in the spot, which can be used to determine the identity of markers if desired.

High performance liquid chromatography (HPLC) can also be used to separate a mixture of biomolecules in a sample based on their different physical properties, such as polarity, charge and size. HPLC instruments typically consist of a reservoir of mobile phase, a pump, an injector, a separation column, and a detector. Biomolecules in a sample are separated by injecting an aliquot of the sample onto the column. Different biomolecules in the mixture pass through the column at different rates due to differences in their partitioning behavior between the mobile liquid phase and the stationary phase. A fraction that corresponds to the molecular weight and/or physical properties of one or more markers can be collected. The fraction can then be analyzed by gas phase ion spectrometry to detect markers. For example, the spots can be analyzed using either MALDI or SELDI (e.g., using ProteinChip® array) as described herein.

Optionally, a marker can be modified before analysis to improve its resolution or to determine its identity. For example, the markers may be subject to proteolytic digestion before analysis. Any protease can be used. Proteases, such as trypsin, that are likely to cleave the markers into a discrete number of fragments are particularly useful. The fragments that result from digestion function as a fingerprint for the markers, thereby enabling their detection indirectly. This is particularly useful where there are markers with similar molecular masses that might be confused for the marker in question. Also, proteolytic fragmentation is useful for high molecular weight markers because smaller markers are more easily resolved by mass spectrometry. In another example, biomolecules can be modified to improve detection resolution. For instance, neuraminidase can be used to remove terminal sialic acid residues from glycoproteins to improve binding to an anionic adsorbent (e.g., cationic exchange ProteinChip® arrays) and to improve detection resolution. In another example, the markers can be modified by the attachment of a tag of particular molecular weight that specifically bind to molecular markers, further distinguishing them. Optionally, after detecting such modified markers, the identity of the markers can be further determined by matching the physical and chemical characteristics of the modified markers in a protein database (e.g., SwissProt).

III. Capture of Markers

Biomarkers are preferably captured with capture reagents immobilized to a solid support, such as any biochip described herein, a multiwell microtiter plate or a resin. In particular, the biomarkers of this invention are preferably captured on SELDI protein biochips. Capture can be on a chromatographic surface or a biospecific surface. Any of the SELDI protein biochips comprising reactive surfaces can be used to capture and detect the biomarkers of this invention. However, the biomarkers of this invention bind well to immobilized metal chelates. The IMAC-3 and IMAC 30 biochips, which nitriloacetic acid functionalities that adsorb transition metal ions, such as $Cu^{++}$ and $Ni^{++}$, by chelation, are the preferred SELDI biochips for capturing the biomarkers of this invention. Any of the SELDI protein biochips comprising reactive surfaces can be used to capture and detect the biomarkers of this invention. These biochips can be derivatized with the antibodies that specifically capture the biomarkers, or they can be derivatized with capture reagents, such as protein A or protein G that bind immunoglobulins. Then the biomarkers can be captured in solution using specific antibodies and the captured markers isolated on chip through the capture reagent.

In general, a sample containing the biomarkers, such as serum, is placed on the active surface of a biochip for a sufficient time to allow binding. Then, unbound molecules are washed from the surface using a suitable eluant, such as phosphate buffered saline. In general, the more stringent the eluant, the more tightly the proteins must be bound to be retained after the wash. The retained protein biomarkers now can be detected by appropriate means.

IV. Detection and Measurement of Markers

Once captured on a substrate, e.g., biochip or antibody, any suitable method can be used to measure a marker or markers in a sample. For example, markers can be detected and/or measured by a variety of detection methods including for example, gas phase ion spectrometry methods, optical methods, electrochemical methods, atomic force microscopy and radio frequency methods. Using these methods, one or more markers can be detected.

A) SELDI

One preferred method of detection and/or measurement of the biomarkers uses mass spectrometry and, in particular, "Surface-enhanced laser desorption/ionization" or "SELDI". SELDI refers to a method of desorption/ionization gas phase ion spectrometry (e.g., mass spectrometry) in which the analyte is captured on the surface of a SELDI probe that engages the probe interface. In "SELDI MS," the gas phase ion spectrometer is a mass spectrometer. SELDI technology is described in more detail above. ApoA1, the six forms of modified Apo A1, transthyretin ΔN10, native transthyretin, cysteinylated transthyretin, sulfonated transthyretin, CysGly modified transthyretin, glutathionylated transthyretin, IAIH4 fragment no. 1, IAIH4 fragment no. 2, and IAIH4 fragment no. 3 are detected as peaks at m/z of about 28043 (or 28055); m/z of about 29977.4, 28262, 28473, 28692, 28844, and 29031; m/z of about 12870.9, m/z of about 13,761 or 13767; m/z of about 13,890.8 or 13888; m/z of about 13850; m/z of about 13944; m/z of about 14,086.9 or 14093; m/z of about 3272; m/z of about 3031; and m/z of about 2884, respectively.

B) Immunoassay

In another embodiment, an immunoassay can be used to detect and analyze markers in a sample. This method comprises: (a) providing an antibody that specifically binds to a marker; (b) contacting a sample with the antibody; and (c) detecting the presence of a complex of the antibody bound to the marker in the sample.

An immunoassay is an assay that uses an antibody to specifically bind an antigen (e.g., a marker). The immunoassay is characterized by the use of specific binding properties of a particular antibody to isolate, target, and/or quantify the antigen. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a marker from specific species such as rat, mouse, or human can be selected to obtain only those polyclonal antibodies that are specifically immunoreactive with that marker and not with other proteins, except for polymorphic variants and alleles of the marker. This selection may be achieved by subtracting out antibodies that cross-react with the marker molecules from other species.

Using the purified markers or their nucleic acid sequences, antibodies that specifically bind to a marker can be prepared using any suitable methods known in the art. See, e.g., Coligan, *Current Protocols in Immunology* (1991); Harlow & Lane, *Antibodies: A Laboratory Manual* (1988); Goding, *Monoclonal Antibodies: Principles and Practice* (2d ed. 1986); and Kohler & Milstein, *Nature* 256:495-497 (1975). Such techniques include, but are not limited to, antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)). Typically a specific or selective reaction will be at least twice background signal or noise and more typically more than 10 to 100 times background.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or ProteinChip® array described above. The sample is preferably a biological fluid sample taken from a subject. Examples of biological fluid samples include blood, serum, plasma, nipple aspirate, urine, tears, saliva etc. In a preferred embodiment, the biological fluid comprises blood serum. The sample can be diluted with a suitable eluant before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxidase, alkaline phosphatase and others commonly used in an ELISA), and colorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker is incubated simultaneously with the mixture.

Methods for measuring the amount of, or presence of, antibody-marker complex include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Electrochemical methods include voltametry and amperometry methods. Radio frequency methods include multipolar resonance spectroscopy. Methods for performing these assays are readily known in the art. Useful assays include, for example, an enzyme immune assay (EIA) such as enzyme-linked immunosorbent assay (ELISA), a radioimmune assay (RIA), a Western blot assay, or a slot blot assay. These methods are also described in, e.g., *Methods in Cell Biology: Antibodies in Cell Biology*, volume 37 (Asai, ed. 1993); *Basic and Clinical Immunology* (Stites & Terr, eds., 7th ed. 1991); and Harlow & Lane, supra.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

Immunoassays can be used to determine presence or absence of a marker in a sample as well as the quantity of a marker in a sample. The amount of an antibody-marker complex can be determined by comparing to a standard. A standard can be, e.g., a known compound or another protein known to be present in a sample. As noted above, the test amount of marker need not be measured in absolute units, as long as the unit of measurement can be compared to a control.

The methods for detecting these markers in a sample have many applications. For example, one or more markers can be measured to aid human cancer diagnosis or prognosis. In another example, the methods for detection of the markers can be used to monitor responses in a subject to cancer treatment. In another example, the methods for detecting markers can be used to assay for and to identify compounds that modulate expression of these markers in vivo or in vitro. In a preferred example, the biomarkers are used to differentiate between the different stages of tumor progression, thus aiding in determining appropriate treatment and extent of metastasis of the tumor.

V. Data Analysis

When the sample is measured and data is generated, e.g., by mass spectrometry, the data is then analyzed by a computer software program. Generally, the software can comprise code that converts signal from the mass spectrometer into computer readable form. The software also can include code that applies an algorithm to the analysis of the signal to determine whether the signal represents a "peak" in the signal corresponding to a marker of this invention, or other useful markers. The software also can include code that executes an algorithm that compares signal from a test sample to a typical signal characteristic of "normal" and human cancer and determines the closeness of fit between the two signals. The software also can include code indicating which the test sample is closest to, thereby providing a probable diagnosis.

In preferred methods of the present invention, multiple biomarkers are measured. The use of multiple biomarkers increases the predictive value of the test and provides greater utility in diagnosis, toxicology, patient stratification and patient monitoring. The process called "Pattern recognition" detects the patterns formed by multiple biomarkers greatly improves the sensitivity and specificity of clinical proteomics for predictive medicine. Subtle variations in data from clinical samples, e.g., obtained using SELDI, indicate that certain patterns of protein expression can predict phenotypes such as the presence or absence of a certain disease, a particular stage of cancer progression, or a positive or adverse response to drug treatments.

Data generation in mass spectrometry begins with the detection of ions by an ion detector as described above. Ions that strike the detector generate an electric potential that is digitized by a high speed time-array recording device that digitally captures the analog signal. Ciphergen's ProteinChip® system employs an analog-to-digital converter (ADC) to accomplish this. The ADC integrates detector output at regularly spaced time intervals into time-dependent bins. The time intervals typically are one to four nanoseconds long. Furthermore, the time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation, baseline subtraction, high frequency noise filtering.

TOF-to-M/Z transformation involves the application of an algorithm that transforms times-of-flight into mass-to-charge ratio (M/Z). In this step, the signals are converted from the time domain to the mass domain. That is, each time-of-flight is converted into mass-to-charge ratio, or M/Z. Calibration can be done internally or externally. In internal calibration, the sample analyzed contains one or more analytes of known M/Z. Signal peaks at times-of-flight representing these massed analytes are assigned the known M/Z. Based on these assigned M/Z ratios, parameters are calculated for a mathematical function that converts times-of-flight to M/Z. In external calibration, a function that converts times-of-flight to M/Z, such as one created by prior internal calibration, is applied to a time-of-flight spectrum without the use of internal calibrants.

Baseline subtraction improves data quantification by eliminating artificial, reproducible instrument offsets that perturb the spectrum. It involves calculating a spectrum baseline using an algorithm that incorporates parameters such as peak width, and then subtracting the baseline from the mass spectrum.

High frequency noise signals are eliminated by the application of a smoothing function. A typical smoothing function applies a moving average function to each time-dependent bin. In an improved version, the moving average filter is a variable width digital filter in which the bandwidth of the filter varies as a function of, e.g., peak bandwidth, generally becoming broader with increased time-of-flight. See, e.g., WO 00/70648, Nov. 23, 2000 (Gavin et al., "Variable Width Digital Filter for Time-of-flight Mass Spectrometry").

Analysis generally involves the identification of peaks in the spectrum that represent signal from an analyte. Peak selection can, of course, be done by eye. However, software is available as part of Ciphergen's ProteinChip® software that can automate the detection of peaks. In general, this software functions by identifying signals having a signal-to-noise ratio above a selected threshold and labeling the mass of the peak at the centroid of the peak signal. In one useful application many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Peak data from one or more spectra can be subject to further analysis by, for example, creating a spreadsheet in which each row represents a particular mass spectrum, each column represents a peak in the spectra defined by mass, and each cell includes the intensity of the peak in that particular spectrum. Various statistical or pattern recognition approaches can applied to the data.

In one example, Ciphergen's Biomarker Patterns™ Software is used to detect a pattern in the spectra that are generated. The data is classified using a pattern recognition process that uses a classification model. In general, the spectra will represent samples from at least two different groups for which a classification algorithm is sought. For example, the groups can be pathological v. non-pathological (e.g., cancer v. non-cancer), drug responder v. drug non-responder, toxic response v. non-toxic response, progressor to disease state v. non-progressor to disease state, phenotypic condition present v. phenotypic condition absent.

The spectra that are generated in embodiments of the invention can be classified using a pattern recognition process that uses a classification model. In some embodiments, data derived from the spectra (e.g., mass spectra or time-of-flight spectra) that are generated using samples such as "known samples" can then be used to "train" a classification model. A "known sample" is a sample that is pre-classified (e.g., cancer or not cancer). Data derived from the spectra (e.g., mass spectra or time-of-flight spectra) that are generated using samples such as "known samples" can then be used to "train" a classification model. A "known sample" is a sample that is pre-classified. The data that are derived from the spectra and are used to form the classification model can be referred to as a "training data set". Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased vs. non diseased).

The training data set that is used to form the classification model may comprise raw data or pre-processed data. In some embodiments, raw data can be obtained directly from time-of-flight spectra or mass spectra, and then may be optionally "pre-processed" in any suitable manner. For example, signals above a predetermined signal-to-noise ratio can be selected so that a subset of peaks in a spectrum is selected, rather than selecting all peaks in a spectrum. In another example, a pre-determined number of peak "clusters" at a common value (e.g., a particular time-of-flight value or mass-to-charge ratio value) can be used to select peaks. Illustratively, if a peak at a given mass-to-charge ratio is in less than 50% of the mass spectra in a group of mass spectra, then the peak at that mass-to-charge ratio can be omitted from the training data set. Pre-processing steps such as these can be used to reduce the amount of data that is used to train the classification model.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, which is herein incorporated by reference in its entirety.

In supervised classification, training data containing examples of known categories are presented to a learning mechanism, which learns one more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as backpropagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. 2002 0138208 A1 (Paulse et al., "Method for analyzing mass spectra," Sep. 26, 2002.

In other embodiments, the classification models that are created can be formed using unsupervised learning methods. Unsupervised classification attempts to learn classifications based on similarities in the training data set, without pre classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described in, for example, WO 01/31580 (Barnhill et al., "Methods and devices for identifying patterns in biological systems and methods of use thereof," May 3, 2001); U.S. 2002/0193950 A1 (Gavin et al., "Method or analyzing mass spectra," Dec. 19, 2002); U.S. 2003/0004402 A1 (Hitt et al., "Process for discriminating between biological states based on hidden patterns from biological data," Jan. 2, 2003); and U.S. 2003/0055615 A1 (Zhang and Zhang, "Systems and methods for processing biological expression data" Mar. 20, 2003).

More specifically, to obtain the biomarkers ApoA1, transthyretin, and IAIH4 fragment, the peak intensity data of samples from cancer patients and healthy controls were used as a "discovery set." This data were combined and randomly divided into a training set and a test set to construct and test multivariate predictive models using a non-linear version of Unified Maximum Separability Analysis ("USMA") classifiers. Details of USMA classifiers are described in U.S. 2003/0055615 A1.

Generally, the data generated from Section IV above is inputted into a diagnostic algorithm (i.e., classification algorithm as described above). The classification algorithm is then generated based on the learning algorithm. The process involves developing an algorithm that can generate the classification algorithm. The methods of the present invention generate a more accurate classification algorithm by accessing a number of ovarian cancer and normal samples of a sufficient number based on statistical sample calculations. The samples are used as a training set of data on learning algorithm.

The generation of the classification, i.e., diagnostic, algorithm is dependent upon the assay protocol used to analyze samples and generate the data obtained in Section IV above. It is imperative that the protocol for the detection and/or measurement of the markers (e.g., in step IV) must be the same as that used to obtain the data used for developing the classification algorithm. The assay conditions, which must be maintained throughout the training and classification systems include chip type and mass spectrometer parameters, as well as general protocols for sample preparation and testing. If the protocol for the detection and/or measurement of the markers (step IV) is changed, the learning algorithm and classification algorithm must also change. Similarly, if the learning algorithm and classification algorithm change, then the protocol for the detection and/or measurement of markers (step IV) must also change to be consistent with that used to generate classification algorithm. Development of a new classification model would require accessing a sufficient number of ovarian cancer and normal samples, developing a new training set of data based on a new detection protocol, generating a new classification algorithm using the data and finally, verifying the classification algorithm with a multi-site study.

The classification models can be formed on and used on any suitable digital computer. Suitable digital computers include micro, mini, or large computers using any standard or specialized operating system such as a Unix, Windows™ or Linux™ based operating system. The digital computer that is used may be physically separate from the mass spectrometer that is used to create the spectra of interest, or it may be coupled to the mass spectrometer. If it is separate from the mass spectrometer, the data must be inputted into the computer by some other means, whether manually or automated.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

VI. Examples of Preferred Embodiments.

In a preferred embodiment, a serum sample is collected from a patient and then fractionated using an anion exchange resin as described above. The biomarkers in the sample are captured using an IMAC copper ProteinChip array. The markers are then detected using SELDI. In such a test one can detect ApoA1, modified Apo A1, transthyretin $\Delta$N10, native transthyretin, cysteinylated transthyretin, sulfonated transthyretin, CysGly modified transthyretin, glutathionlyated transthyretin, IAIH4 fragment no. 1, IAIH4 fragment no. 2, and/or IAIH4 fragment no. 3. The results are then entered into a computer system, which contains an algorithm that is designed using the same parameters that were used in the learning algorithm and classification algorithm to originally determine the biomarkers. The algorithm produces a diagnosis based upon the data received relating to each biomarker.

In especially preferred embodiments, the amount of biomarker CA125II is also detected, either by using a known method, e.g., immunoassay, or by using a SELDI Protein chip array. In these embodiments, the results for marker CA125II are also entered into the computer algorithm and used to prepare a diagnosis. A diagnostic test that is based on the detection of the four biomarkers, ApoA1, transthyretin $\Delta$N10, IAIH4 fragment no. 1, and CA125II has a specificity of at least about 80%.

The diagnosis is determined by examining the data produced from the SELDI tests with the classification algorithm that is developed using the biomarkers. The classification algorithm depends on the particulars of the test protocol used to detect the biomarkers. These particulars include, for example, sample preparation, chip type and mass spectrometer parameters. If the test parameters change, the algorithm must change. Similarly, if the algorithm changes, the test protocol must change.

In another embodiment, the sample is collected from the patient. The biomarkers are captured using an antibody ProteinChip array as described above. The markers are detected using a biospecific SELDI test system. In such a test one can detect ApoA1, modified Apo A1, transthyretin $\Delta$N10, native transthyretin, cysteinylated transthyretin, sulfonated transthyretin, CysGly modified transthyretin, glutathionlyated transthyretin, IAIH4 fragment no. 1, IAIH4 fragment no. 2, and/or IAIH4 fragment no. 3. The results are then entered into a computer system, which contains an algorithm that is designed using the same parameters that were used in the learning algorithm and classification algorithm to originally determine the biomarkers. The algorithm produces a diagnosis based upon the data received relating to each biomarker.

In yet other preferred embodiments, the markers are captured and tested using non-SELDI formats. In one example, the sample is collected from the patient. The biomarkers are captured on a substrate using other known means, e.g., antibodies to the markers. The markers are detected using methods known in the art, e.g., optical methods and refractive index. Examples of optical methods include detection of fluorescence, e.g., ELISA. Examples of refractive index include surface plasmon resonance. The results for the markers are then subjected to an algorithm, which may or may not require artificial intelligence. The algorithm produces a diagnosis based upon the data received relating to each biomarker.

In any of the above methods, the data from the sample may be fed directly from the detection means into a computer containing the diagnostic algorithm. Alternatively, the data obtained can be fed manually, or via an automated means, into a separate computer that contains the diagnostic algorithm.

VII. Diagnosis of Subject and Determination of Ovarian Cancer Status

Any biomarker, individually, is useful in aiding in the determination of ovarian cancer status. First, the selected biomarker is measured in a subject sample using the methods described herein, e.g., capture on a SELDI biochip followed by detection by mass spectrometry. Then, the measurement is compared with a diagnostic amount or control that distinguishes an ovarian cancer status from a non-cancer status. The diagnostic amount will reflect the information herein that a particular biomarker is up-regulated or down-regulated in a cancer status compared with a non-cancer status. As is well understood in the art, the particular diagnostic amount used can be adjusted to increase sensitivity or specificity of the diagnostic assay depending on the preference of the diagnostician. The test amount as compared with the diagnostic amount thus indicates ovarian cancer status.

While individual biomarkers are useful diagnostic markers, it has been found that a combination of biomarkers provides greater predictive value than single markers alone. Specifically, the detection of a plurality of markers in a sample increases the percentage of true positive and true negative diagnoses and would decrease the percentage of false positive or false negative diagnoses. Thus, preferred methods of the present invention comprise the measurement of more than one biomarker. For example, the methods of the present invention have an AUC from ROC analysis greater than 0.50, more preferred methods have an AUC greater than 0.60, more preferred methods have an AUC greater than 0.70. Especially preferred methods have an AUC greater than 0.70 and most preferred methods have an AUC greater than 0.80.

Furthermore, using a method that measures the combination of the three preferred biomarkers of the present invention with Marker 4, e.g., CA125, significantly improves upon the diagnostic performance of CA125, providing a test that has an AUC greater than 0.50, more preferred tests have an AUC greater than 0.60, more preferred tests have an AUC greater than 0.70.

In order to use the biomarkers in combination, a logistical regression algorithm is useful. The UMSA algorithm is particularly useful to generate a diagnostic algorithm from test data. This algorithm is disclosed in Z. Zhang et al., Applying classification separability analysis to microaary data. In: Lin S M, Johnson K F, eds. Methods of Microarray data analysis: papers from CAMDA '00. Boston: Kluwer Academic Publishers, 2001:125-136; and Z. Zhang et al., Fishing Expedition—a Supervised Approach to Extract Patterns from a Compendium of Expression Profiles. In Lin S M, Johnson, K F, eds. Microarray Data Analysis II: Papers from CAMDA '01. Boston: Kluwer Academic Publishers, 2002.

The learning algorithm will generate a multivariate classification (diagnostic) algorithm tuned to the particular specificity and sensitivity desired by the operator. The classification algorithm can then be used to determine ovarian cancer status. The method also involves measuring the selected biomarkers in a subject sample (e.g., Apo A1, modified Apo A1, transthyretin $\Delta$N10, native transthyretin, cysteinylated transthyretin, sulfonated transthyretin, CysGly modified transthyretin, glutathionlyated transthyretin, IAIH4 fragment no. 1, IAIH4 fragment no. 2, and/or IAIH4 fragment no. 3). These measurements are submitted to the classification algorithm. The classification algorithm generates an indicator score that indicates ovarian cancer status.

In some embodiments, the mere presence or absence of a marker, without quantifying the amount of marker, is useful and can be correlated with a probable diagnosis of ovarian cancer. For example, IAIH4 fragments can be more frequently detected in human ovarian cancer patients than in normal subjects. Equally, for example, biomarkers Apo A1 and transthyretin, can be less frequently detected in human ovarian cancer patients than in normal subjects. Thus, a detected presence or absence, respectively, of these markers in a subject being tested indicates that the subject has a higher probability of having ovarian cancer.

In other embodiments, the measurement of markers can involve quantifying the markers to correlate the detection of markers with a probable diagnosis of ovarian cancer. Thus, if the amount of the markers detected in a subject being tested is different compared to a control amount (i.e., higher or lower than the control, depending on the marker), then the subject being tested has a higher probability of having ovarian cancer.

The correlation may take into account the amount of the marker or markers in the sample compared to a control amount of the marker or markers (up or down regulation of the marker or markers) (e.g., in normal subjects in whom human cancer is undetectable). A control can be, e.g., the average or median amount of marker present in comparable samples of normal subjects in whom human cancer is undetectable. The control amount is measured under the same or substantially similar experimental conditions as in measuring the test amount. The correlation may take into account the presence or absence of the markers in a test sample and the frequency of detection of the same markers in a control. The correlation may take into account both of such factors to facilitate determination of ovarian cancer status.

In certain embodiments of the methods of qualifying ovarian cancer status, the methods further comprise managing subject treatment based on the status. As aforesaid, such management describes the actions of the physician or clinician subsequent to determining ovarian cancer status. For example, if the result of the methods of the present invention is inconclusive or there is reason that confirmation of status is necessary, the physician may order more tests. Alternatively, if the status indicates that surgery is appropriate, the physician may schedule the patient for surgery. In other instances, the patient may receive chemotherapy or radiation treatments, either in lieu of, or in addition to, surgery. Likewise, if the result is negative, e.g., the status indicates late stage ovarian cancer or if the status is otherwise acute, no further action may be warranted. Furthermore, if the results show that treatment has been successful, no further management may be necessary.

The invention also provides for such methods where the biomarkers (or specific combination of biomarkers) are measured again after subject management. In these cases, the methods are used to monitor the status of the cancer, e.g., response to cancer treatment, remission of the disease or progression of the disease. Because of the ease of use of the methods and the lack of invasiveness of the methods, the methods can be repeated after each treatment the patient receives. This allows the physician to follow the effectiveness of the course of treatment. If the results show that the treatment is not effective, the course of treatment can be altered accordingly. This enables the physician to be flexible in the treatment options.

In another example, the methods for detecting markers can be used to assay for and to identify compounds that modulate expression of these markers in vivo or in vitro.

The methods of the present invention have other applications as well. For example, the markers can be used to screen for compounds that modulate the expression of the markers in vitro or in vivo, which compounds in turn may be useful in treating or preventing ovarian cancer in patients. In another example, the markers can be used to monitor the response to treatments for ovarian cancer. In yet another example, the markers can be used in heredity studies to determine if the subject is at risk for developing ovarian cancer. For instance, certain markers may be genetically linked. This can be determined by, e.g., analyzing samples from a population of ovarian cancer patients whose families have a history of ovarian cancer. The results can then be compared with data obtained from, e.g., ovarian cancer patients whose families do not have a history of ovarian cancer. The markers that are genetically linked may be used as a tool to determine if a subject whose family has a history of ovarian cancer is pre-disposed to having ovarian cancer.

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the presence or absence in a test subject of any the biomarkers of this invention is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

VIII. Kits

In yet another aspect, the present invention provides kits for qualifying ovarian cancer status, wherein the kits can be used to measure the markers of the present invention. For example, the kits can be used to measure any one or more of the markers described herein, which markers are differentially present in samples of ovarian cancer patient and normal subjects. The kits of the invention have many applications. For example, the kits can be used to differentiate if a subject has ovarian cancer or has a negative diagnosis, thus enabling the physician or clinician to diagnose the presence or absence of the cancer. The kits can also be used to monitor the patient's response to a course of treatment, enabling the physician to modify the treatment based upon the results of the test. In another example, the kits can be used to identify compounds that modulate expression of one or more of the markers in in vitro or in vivo animal models for ovarian cancer.

The present invention therefore provides kits comprising (a) a capture reagent that binds a biomarker selected from Apo A1, modified Apo A1, transthyretin $\Delta$N10, native transthyretin, cysteinylated transthyretin, sulfonated transthyretin, CysGly modified transthyretin, glutathionlyated transthyretin, IAIH4 fragment no. 1, IAIH4 fragment no. 2, and IAIH4 fragment no. 3, and combinations thereof; and (b) a container comprising at least one of the biomarkers. In preferred kit, the capture reagent binds a plurality of the biomarkers. The capture reagent may also bind at least one known biomarker, Marker 4, e.g., CA125. In certain preferred embodiments, the kit of further comprises a second capture reagent that binds one of the biomarkers that the first capture reagent does not bind.

Further kits provided by the invention comprise (a) a first capture reagent that binds at least one biomarker selected from Apo A1, modified Apo A1, transthyretin $\Delta$N10, native transthyretin, cysteinylated transthyretin, sulfonated transthyretin, CysGly modified transthyretin, glutathionlyated transthyretin, IAIH4 fragment no. 1, IAIH4 fragment no. 2, and IAIH4 fragment no. 3, and (b) a second capture reagent that binds at least one of the biomarkers that is not bound by the first capture reagent. Preferably, at least one of the capture reagents is an antibody. Certain kits further comprise an MS probe to which at least one capture reagent is attached or is attachable.

While the capture reagent can be any type of reagent, preferably the reagent is a SELDI probe. In certain kits of the present invention, the capture reagent comprises an IMAC.

The invention also provides kits comprising (a) a first capture reagent that binds at least one biomarker selected from Apo A1, modified Apo A1, transthyretin $\Delta$N10, native transthyretin, cysteinylated transthyretin, sulfonated transthyretin, CysGly modified transthyretin, glutathionlyated transthyretin, IAIH4 fragment no. 1, IAIH4 fragment no. 2, and IAIH4 fragment no. 3 and (b) instructions for using the capture reagent to measure the biomarker. In certain of these kits, the capture reagent comprises an antibody. Furthermore, some of the aforesaid kits further comprise an MS probe to which the capture reagent is attached or is attachable. In some kits, the capture reagent comprises an IMAC. Each of the three markers identified here binds to the IMAC ProteinChip® array. Therefore, one preferred embodiment of the present invention includes a high-throughput test for early detection of ovarian cancer, which analyzes a patient's sample on the IMAC ProteinChip® array for these three analytes, as well as the traditional CA-125 ELISA (or the CA-125 ELISA may be transferred to the ProteinChip® array platform).

In other embodiments, the kits as described herein comprise at least one capture reagent that binds at least one biomarker selected from Markers I through XLVIII.

Certain kits of the present invention further comprise a wash solution, or eluant, that selectively allows retention of the bound biomarker to the capture reagent as compared with other biomarkers after washing. Alternatively, the kit may contain instructions for making a wash solution, wherein the combination of the adsorbent and the wash solution allows detection of the markers using gas phase ion spectrometry.

Preferably, the kit comprises written instructions for use of the kit for detection of cancer and the instructions provide for contacting a test sample with the capture reagent and detecting one or more biomarkers retained by the capture reagent. For example, the kit may have standard instructions informing a consumer how to wash the capture reagent (e.g., probe) after a sample of blood serum contacts the capture reagent. In another example, the kit may have instructions for pre-fractionating a sample to reduce complexity of proteins in the sample. In another example, the kit may have instructions for automating the fractionation or other processes.

Such kits can be prepared from the materials described above, and the previous discussion of these materials (e.g., probe substrates, capture reagents, adsorbents, washing solutions, etc.) is fully applicable to this section and will not be repeated.

In another embodiment, the kit may comprise a first substrate comprising an adsorbent thereon (e.g., a particle functionalized with an adsorbent) and a second substrate onto which the first substrate can be positioned to form a probe, which is removably insertable into a gas phase ion spectrometer. In other embodiments, the kit may comprise a single substrate, which is in the form of a removably insertable probe with adsorbents on the substrate. In yet another embodiment, the kit may further comprise a pre-fractionation spin column (e.g., Cibacron blue agarose column, anti-HSA agarose column, K-30 size exclusion column, Q-anion exchange spin column, single stranded DNA column, lectin column, etc.).

In another embodiment, a kit comprises (a) an antibody that specifically binds to a marker; and (b) a detection reagent. Such kits can be prepared from the materials described above, and the previous discussion regarding the materials (e.g., antibodies, detection reagents, immobilized supports, etc.) is fully applicable to this section and will not be repeated. Optionally, the kit may further comprise pre-fractionation spin columns. In some embodiments, the kit may further comprise instructions for suitable operation parameters in the form of a label or a separate insert.

Optionally, the kit may further comprise a standard or control information so that the test sample can be compared with the control information standard to determine if the test amount of a marker detected in a sample is a diagnostic amount consistent with a diagnosis of ovarian cancer.

The invention also provides an article manufacture comprising at least one capture reagent bound to at least two biomarkers selected from Apo A1, modified Apo A1, transthyretin ΔN10, native transthyretin, cysteinylated transthyretin, sulfonated transthyretin, CysGly modified transthyretin, glutathionlyated transthyretin, IAIH4 fragment no. 1, IAIH4 fragment no. 2, and IAIH4 fragment no. 3. Examples of articles of manufacture of the present invention include, but are not limited to, ProteinChip® Arrays, probes, microtitre plates, beads, test tubes, microtubes, and any other solid phase onto which a capture reagent can be incorporated. Other embodiments of the article of manufacture of the present invention further comprise a capture reagent that binds other known ovarian cancer markers, i.e., Marker 4. In an example of such an article, a ProteinChip® Array for example, will have an adsorbent that will capture Apo A1, modified Apo A1, transthyretin ΔN10, native transthyretin, cysteinylated transthyretin, sulfonated transthyretin, CysGly modified transthyretin, glutathionlyated transthyretin, IAIH4 fragment no. 1, IAIH4 fragment no. 2, and IAIH4 fragment no. 3 and Marker 4. In an especially preferred embodiment, Marker 4 is CA125. In another example, a microtitre plate will have antibodies that are capable of binding Apo A1, modified Apo A1, transthyretin ΔN10, native transthyretin, cysteinylated transthyretin, sulfonated transthyretin, CysGly modified transthyretin, glutathionlyated transthyretin, IAIH4 fragment no. 1, IAIH4 fragment no. 2, and/or IAIH4 fragment no. 3 and Marker 4. These are a few examples of such articles of manufacture. One of ordinary skill in the art would readily be able to manufacture other such articles in accordance with the teachings described herein.

The present invention also provides a system comprising a plurality of capture reagents each of which has bound to it a different biomarker selected from Apo A1, modified Apo A1, transthyretin ΔN10, native transthyretin, cysteinylated transthyretin, sulfonated transthyretin, CysGly modified transthyretin, glutathionlyated transthyretin, IAIH4 fragment no. 1, IAIH4 fragment no. 2, and/or IAIH4 fragment no. 3t, and at least one marker that fits in the category of Marker 4. An example of such a system includes, but is not limited to, a set of ProteinChip® Arrays, which comprise adsorbents that bind one or more of the biomarkers selected from Apo A1, modified Apo A1, transthyretin ΔN10, native transthyretin, cysteinylated transthyretin, sulfonated transthyretin, CysGly modified transthyretin, glutathionlyated transthyretin, IAIH4 fragment no. 1, IAIH4 fragment no. 2, and/or IAIH4 fragment no. 3. In this type of system, there may be one ProteinChip® Array for each of the biomarkers. Or, alternatively, there may be one ProteinChip® Array for a plurality of markers from the group of Apo A1, modified Apo A1, transthyretin ΔN10, native transthyretin, cysteinylated transthyretin, sulfonated transthyretin, CysGly modified transthyretin, glutathionlyated transthyretin, IAIH4 fragment no. 1, IAIH4 fragment no. 2, and/or IAIH4 fragment no. 3 and a second ProteinChip® Array for CA125. Examples of other systems include those in which the capture reagents are test tubes containing an antibody for each of the biomarkers, either separately, or in groups. One of ordinary skill in the art would readily be able to manufacture other such articles in accordance with the teachings described herein.

The present invention also provides a screening test comprising (a) contacting a kallikrein with a kallikrein substrate and with a test agent and (b) determining whether the test agent modulates the activity of the kallikrein. In one such test, the substrate is inter-alpha-trypsin inhibitor heavy chain H4 precursor. As discussed below, it is believed that several kallikreins have been found to be dys-regulated in ovarian cancer (reviewed in Diamandis 2002). Thus, the determination of kallikrein activity is indicative of ovarian cancer. In such a method, step of determining whether the test agent modulates the activity of the kallikrein comprises measuring the presence or amount of IAIH4 fragment no. 1, IAIH4 fragment no. 2, and/or IAIH4 fragment no. 3. The methods of measuring IAIH4 fragments described above can be used in the screening methods.

VIII. Use of Biomarkers for Ovarian Cancer in Screening Assays

The methods of the present invention have other applications as well. For example, the biomarkers can be used to screen for compounds that modulate the expression of the biomarkers in vitro or in vivo, which compounds in turn may be useful in treating or preventing ovarian cancer in patients. In another example, the biomarkers can be used to monitor the response to treatments for ovarian cancer. In yet another example, the biomarkers can be used in heredity studies to determine if the subject is at risk for developing ovarian cancer.

Thus, for example, the kits of this invention could include a solid substrate having a hydrophobic function, such as a protein biochip (e.g., a Ciphergen ProteinChip array) and a buffer for washing the substrate, as well as instructions providing a protocol to measure the biomarkers of this invention on the chip and to use these measurements to diagnose ovarian cancer.

Compounds suitable for therapeutic testing may be screened initially by identifying compounds which interact with one or more biomarkers listed in identified herein. By way of example, screening might include recombinantly expressing a biomarker of this invention, purifying the biomarker, and affixing the biomarker to a substrate. Test compounds would then be contacted with the substrate, typically in aqueous conditions, and interactions between the test compound and the biomarker are measured, for example, by measuring elution rates as a function of salt concentration. Certain proteins may recognize and cleave one or more biomarkers of this invention, in which case the proteins may be detected by monitoring the digestion of one or more biomarkers in a standard assay, e.g., by gel electrophoresis of the proteins.

In a related embodiment, the ability of a test compound to inhibit the activity of one or more of the biomarkers of this invention may be measured. One of skill in the art will recognize that the techniques used to measure the activity of a particular biomarker will vary depending on the function and properties of the biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibit or enhance the activity of a given biomarker may be determined by measuring the rates of catalysis in the presence or absence of the test compounds. The ability of a test compound to interfere with a non-enzymatic (e.g., structural) function or activity of one of the biomarkers of this invention may also be measured. For example, the self-assembly of a multi-protein complex which includes one of the biomarkers of this invention may be monitored by spectroscopy in the presence or absence of a test compound. Alternatively, if the biomarker is a non-enzymatic enhancer of transcription, test compounds which interfere with the ability of the biomarker to enhance transcription may be identified by measuring the levels of biomarker-dependent transcription in vivo or in vitro in the presence and absence of the test compound.

Test compounds capable of modulating the activity of any of the biomarkers of this invention may be administered to patients who are suffering from or are at risk of developing Ovarian cancer or other cancer. For example, the administration of a test compound which increases the activity of a particular biomarker may decrease the risk of ovarian cancer in a patient if the activity of the particular biomarker in vivo prevents the accumulation of proteins for Ovarian cancer. Conversely, the administration of a test compound which decreases the activity of a particular biomarker may decrease the risk of Ovarian cancer in a patient if the increased activity of the biomarker is responsible, at least in part, for the onset of Ovarian cancer.

In an additional aspect, the invention provides a method for identifying compounds useful for the treatment of disorders such as ovarian cancer which are associated with increased levels of modified forms of IAIH4. For example, in one embodiment, cell extracts or expression libraries may be screened for compounds which catalyze the cleavage of full-length IAIH4 to form truncated forms of IAIH4. In one embodiment of such a screening assay, cleavage of IAIH4 may be detected by attaching a fluorophore to IAIH4 which remains quenched when IAIH4 is uncleaved but which fluoresces when the protein is cleaved. Alternatively, a version of full-length IAIH4 modified so as to render the amide bond between amino acids x and y uncleavable may be used to selectively bind or "trap" the cellular protesase which cleaves full-length IAIH4 at that site in vivo. Methods for screening and identifying proteases and their targets are well-documented in the scientific literature, e.g., in Lopez-Ottin et al. (Nature Reviews, 3:509-519 (2002)).

In yet another embodiment, the invention provides a method for treating or reducing the progression or likelihood of a disease, e.g., ovarian cancer, which is associated with the increased levels of truncated IAIH4. For example, after one or more proteins have been identified which cleave full-length IAIH4, combinatorial libraries may be screened for compounds which inhibit the cleavage activity of the identified proteins. Methods of screening chemical libraries for such compounds are well-known in art. See, e.g., Lopez-Otin et al. (2002). Alternatively, inhibitory compounds may be intelligently designed based on the structure of IAIH4.

Full-length IAIH4 is believed to bind to and inhibit the activity of plasma kallikrein. (Pu X P, et al., *Biochim Biophys Acta* 1994; 1208:338-43; Nishimura H, et al., *FEBS Lett* 1995; 357:207-11). N-terminal truncations of IAIH4 are thought to diminish IAIH4's protease inhibitory activity. See, e.g., Abrahamson et al. (Biochem. J. 273:621-626 (1991)). Compounds which impart truncated IAIH4 with the functionality of full-length IAIH4 are likely therefore to be useful in treating conditions, such as ovarian cancer, which are associated with the truncated form of IAIH4. Therefore, in a further embodiment, the invention provides methods for identifying compounds which increase the affinity of truncated IAIH4 for its target proteases. For example, compounds may be screened for their ability to impart truncated IAIH4 with the protease inhibitory activity of full-length IAIH4. Test compounds capable of modulating the inhibitory activity of IAIH4 or the activity of molecules which interact with IAIH4 may then be tested in vivo for their ability to slow or stop the progression of ovarian cancer in a subject.

At the clinical level, screening a test compound includes obtaining samples from test subjects before and after the subjects have been exposed to a test compound. The levels in the samples of one or more of the biomarkers of this invention may be measured and analyzed to determine whether the levels of the biomarkers change after exposure to a test compound. The samples may be analyzed by mass spectrometry, as described herein, or the samples may be analyzed by any appropriate means known to one of skill in the art. For example, the levels of one or more of the biomarkers of this invention may be measured directly by Western blot using radio- or fluorescently-labeled antibodies which specifically bind to the biomarkers. Alternatively, changes in the levels of mRNA encoding the one or more biomarkers may be measured and correlated with the administration of a given test compound to a subject. In a further embodiment, the changes in the level of expression of one or more of the biomarkers may be measured using in vitro methods and materials. For example, human tissue cultured cells which express, or are capable of expressing, one or more of the biomarkers of this invention may be contacted with test compounds. Subjects who have been treated with test compounds will be routinely examined for any physiological effects which may result from the treatment. In particular, the test compounds will be evaluated for their ability to decrease disease likelihood in a subject. Alternatively, if the test compounds are administered to subjects who have previously been diagnosed with ovarian cancer, test compounds will be screened for their ability to slow or stop the progression of the disease.

IX. Method to Derive a Classification Algorithm and Diagnosis

A dataset can be analyzed by multiple classification algorithms. Some classification algorithms provide discrete rules for classification; others provide probability estimates of a certain outcome (class). In the latter case, the decision (diagnosis) is made based on the class with the highest probability. For example, consider the three-class problem: healthy, benign, and cancer. Suppose that a classification algorithm (e.g. Nearest neighbor) is constructed and applied to sample A, and the probability of the sample being healthy is 0, benign is 33%, and cancer is 67%. Sample A would be diagnosed as being cancer. This approach, however, does not take into account any "fuzziness" in the diagnosis i.e. that there was a certain probability that the sample was benign. Therefore, the diagnosis would be the same as for sample B, which has a probability of 0 of being healthy or benign and a probability of 1 of being cancer.

We propose to construct an index derived from the probabilities of each class assignment. This index can be constructed in any computationally logical manner; in this case we create a simple linear combination of the three probabilities i.e.

$$I = 0*p(\text{control}) + 1*p(\text{benign}) + 2*p(\text{cancer})$$

A sample with a probability of 1 of being control would have a value of 0, a sample with a probability of 1 of being benign would have a value of 1, and a sample with a probability of 1 of being cancer would have a value of 2. Clinical decision making could therefore be made on this index. A person with an index score of 0 would have no risk of having cancer, while a person with an index score of 2 would have a very high risk of having cancer. A person with an intermediate score would have varying risks of cancer, with the risk increasing with the index score.

We applied this approach to a series of 180 samples from the Mayo Clinic. We derived a nearest neighbor classification algorithm based on the five transthyretin forms and one apolipoprotein A1 form, with and without including age. The following figure plots the index score as a function of class when age is not included in the model.

Individuals with a score of 0 will have virtually no risk for ovarian cancer, based on these markers, while individuals with a score of 2 have the highest risk of having ovarian cancer.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

EXAMPLES

Materials and Methods
Samples

Proteomic profiling data were retrospectively obtained from a total of 503 serum specimens collected at Groningen University Hospital (Groningen, the Netherlands), Duke University Medical Center (Durham, N.C.), Royal Hospital for Women (Sydney, Australia), and MD Anderson Cancer Center (Houston, Tex.). The ovarian cancer group consisted of 65 patients with stages I/II invasive epithelial ovarian cancer and 88 patients with stages III/IV invasive epithelial ovarian cancer, 28 patients with borderline tumors, and 14 patients with recurrent disease. The cancer cases were optimally staged by pathologists based on FIGO criteria. Among the 65 patients with stages I/II invasive epithelial ovarian cancer, 20 were serous, 17 were mucinous, 15 were endometrioid, 8 were clear cell, 1 was carcinosarcoma, and 4 were mixed epithelial carcinoma. The samples also included 166 patients diagnosed with benign pelvic masses and 142 healthy controls. The characteristics and basic descriptive statistics of the study population, including age and CA125 levels, are listed in Table 1.

All samples from patients were collected before surgery or treatment and specimens from healthy volunteers were collected with institutional approval. The blood was permitted to clot and serum was promptly separated. All samples were stored at −70° C. and thawed immediately prior to assay. CA125 levels of all patients were available from a previous study using a CA125II radioimmunoassay kit (Centocor).

In addition to the 503 specimens for proteomic profiling, 142 archived serum specimens collected for routine clinical laboratory testing at Johns Hopkins Medical Institutions were tested for levels of the identified biomarkers for which an immunoassay test was available. Of these samples, 41 were from patients with late stage ovarian cancer and 41 were from healthy women. The remaining 60 samples consisted of 20 each from patients with breast cancer, colon cancer, and prostate cancer and were used to test the tumor site specificity of the identified biomarkers (Table 3). All samples were processed within two to four hours after collection and stored at 2-8° C. for a maximum of 48 hours prior to freezing at −70° C. CA125II assay was also performed using a two-site immunoenzymometric assay on the Tosoh AIA-600 II analyzer (Tosoh Medics).

Example 1

Protein Expression Profiling

Serum Fractionation: Serum samples were thawed on ice and then centrifuged at 20000 g for 10 minutes to remove precipitate. 20 µl of serum were mixed with 30 µl of a denaturing buffer (U9: 9 M urea, 2% CHAPS, 50 mM Tris pH 9.0) and vortexed for twenty minutes at 4 degrees. For each sample, 180 µl of Hyper Q DF anion exchange resin was equilibrated in 200 µl of U1 buffer (U9 that was diluted 1:9 in 50 mM Tris pH 9.0) three times. The denatured serum was applied to the resin and allowed to bind for thirty minutes. The unbound material was collected and then 100 µl of 50 mM Tris 9.0 containing 0.1% OGP was added to the resin. This wash was collected and combined with the unbound material (flow through; fraction 1). Fractions were then collected in a step-wise pH gradient using two times 100 ul each aliquots of wash buffers at pH 7, 5, 4, 3, and organic solvent). This led to the collection of a total of six fractions. Fractionation was performed on a Biomek 2000 automated liquid handler (Beckman) and a Micromix shaker (DPC). A sample of control pooled human serum (Intergen) was processed identically to monitor assay performance.

A. Materials for Protein Expression Profiling
Beckman Biomek 2000 Automated workstation
Q Hyper DF Ceramic Anion Exchange Resin (Biosepra, France) 96 well v-bottom microplate
96 well loprodyne membrane filter plate (Silent Screen, Nalge Nunc)
Equilibration Buffer—50 mM Tris-HCl pH 9.0
U9-9M Urea, 2.0% CHAPS, 50 mM Tris-HCl pH 9.0 U1-1M Urea, 0.22% CHAPS, 50 mM Tris-HC 1 pH 9.0 pH 9.0
Buffer—100 mM Tris-HCl, 0.1% OGP pH 9.0 pH 7.0
Buffer—100 mM HEPES, 0.1% OGP pH 7.0 pH 5.0
Buffer—100 mM Na Acetate, 0.1% OGP pH 5.0 pH 4.0
Buffer—100 mM Na Acetate, 0.1% OGP pH 4.0 pH 3.0
Buffer—50 mM Na Citrate, 0.1% OGP pH 3.0
Org Buffer—33.3% Isopropanol/16.67% Acetonitrile/0.5% Trifluoroacetic acid (TFA)

B. Procedure
Serum Denaturation

Pipette 20 ul of serum to a 96 well v-bottom plate. Add 30 ul of U9 to each well that contains serum. Cover the 96 well plate with plate sealing film. Vortex at 4° C. for at least 20 minutes while the resin is equilibrated.

Resin Equilibration

Wash the resin 5 times with three bed volumes of 50 mM Tris-HCl pH 9.0. This can be done in a 50 mL centrifuge tube. Create a 50/50 slurry of resin by adding an equivalent volume of 50 mM Tris-HCl pH 9.0 to the resin. Add 180 ul of the 50/50 slurry to each well of a 96 well filter plate. Vortex the tube containing the slurry regularly (every two or three aliquots) to ensure a consistent ratio of resin to buffer. Then filter the buffer and add 200 ul of U1 and filter once more. This is then done two more times in the same manner.

Sample Application and Incubation

The next step is to bind the serum to the resin. The first step in this process is to pipette 50 ul of each sample to a corresponding well in a filter plate. Next add, 50 ul of U1 to each well of the sample plate and mix 5 times. Then pipette 50 ul from each well of the sample plate to the corresponding well in the filter plate. Vortex for 30 minutes at 4° C.

The next step is to collect the fractions. Place a V bottom 96 well plate under the filter plate. Collect the flow-through from the filter plate. 100 ul of wash buffer 1 is then added to each well of the filter plate. Next vortex for 10 minutes at room temperature. Fraction 1 contains the flow-through and pH 9 eluent. Next add 100 ul of wash buffer 2 to each well of the filter plate. Vortex for 10 minutes at room temperature. Place a clean V bottom plate under the filter plate and collect fraction 2 in the plate. Add 100 ul of wash buffer 2 to each well in the filter plate. Vortex for 10 minutes at room temperature. Collect the remainder of fraction 2 in the V bottom 96 well plate. Fraction 2 contains pH7 eluent. Add 100 ul of Wash buffer 3 to each well of the filter plate. Vortex for 10 minutes at room temperature. Place a clean V bottom plate under the filter plate and collect fraction 3. Add 100 ul of Wash buffer 3 to each well of the filter plate and vortex for 10 minutes at room temperature. Collect the remainder of fraction 3 in the V bottom plate. Fraction 3 contains pH 5 eluent. Add 100 ul of Wash buffer 4 to the filter plate and vortex for 10 minutes at room temperature. Place a clean V bottom plate under the filter plate and collect fraction 4. Next 100 ul of Wash buffer 4 to the filter plate and vortex for 10 minutes at room temperature. Collect the remaining fraction 4 in the V bottom plate. Fraction 4 contains the pH 4 eluent. Then add 100 ul of Wash buffer 5 to each well of the filter plate and vortex for 10 minutes at room temperature. Place a clean V bottom plate under the filter plate and collect fraction 5. Next add 100 ul of Wash buffer 5 to the filter plate and vortex for 10 minutes at room temperature. Collect the remaining fraction 5 in the V bottom plate. Fraction 5 contains pH 3 eluent. Add 100 ul of Wash Buffer 6 to the filter plate and vortex for 10 minutes at room temperature. Next place a clean V bottom plate under the filter plate and collect fraction 6. Add 100 ul of Wash buffer 6 to the filter plate and once again vortex for 10 minutes at room temperature. Collect the remaining fraction. Fraction 6 contains the organic solvent eluent.

Freeze the fractions until ready for Chip Binding Protocol. Array Binding: 10 µl of each fraction was mixed with 90 µl of binding buffer and bound in triplicate to IMAC, SAX, H50 and WCX ProteinChip arrays (Ciphergen Biosystems). For IMAC, the binding buffer was 100 mM sodium phosphate pH 7.0 containing 500 mM NaCl; for SAX, the binding buffer was 100 mM Sodium Phosphate, pH 7; for H50, the binding buffer was 50% Acetonitrile in $H_2O$; and for WCX, the buffer was 100 mM Na Acetate pH 4.0. Binding was allowed to occur for thirty minutes at room temperature. Chips were then washed three times with binding buffer and then twice with water. The matrix used was sinapinic acid.

Data Acquisition and Analysis: For both SELDI analysis, all arrays were read using a Ciphergen PBS II ProteinChip® Array reader, a time-lag focusing, linear, laser desorption/ionization-time of flight mass spectrometer. All spectra were acquired in the positive-ion mode. Time-lag focusing delay times were set at 400 ns for peptides and 1900 ns for proteins. Ions were extracted using a 3 kV ion extraction pulse, and accelerated to final velocity using 20 kV of acceleration potential. The system employed a pulsed nitrogen laser at repetition rates varying from 2 to 5 pulses per second. Typical laser fluence varied from 30-150 $\mu J/mm^2$. An automated analytical protocol was used to control the data acquisition process in most of the sample analysis. Each spectrum was an average of at least 100 laser shots and externally calibrated against a mixture of known peptides or proteins. Instruments were monitored weekly for performance using insulin and immunoglobulin standards. Each chip was read at two laser energies, low and high. Spectra were externally calibrated, baseline subtracted with a setting of 8 times the fitting width, and then normalized to total ion current (excluding the matrix region).

Example 2

Statistical Analysis

Biomarker Discovery: Qualified mass peaks (S/N>5, cluster mass window at 0.3%) within the mass range of M/Z 2 kD-50 kD were selected from the SELDI spectra. In order to obtain a more consistent level of data variance across the range of spectrum of interest, logarithmic transformation was applied to the peak intensity prior to further analysis. The peak intensity data of early stage epithelial ovarian cancer patients and healthy controls from Duke University Medical Center (Ca n=36, HC n=47) and Groningen University Hospital (Ca n=20, HC n=30) were analyzed using the Unified Maximum Separability Analysis (UMSA) algorithm that was first used for microarray data analysis and subsequently for protein expression data (ProPeak, 3Z Informatics). ((Li J, et al., *Clin Chem* 2002; 48:1296-304; Rai A J, et al., Zhang Z, et al. *Arch Pathol Lab Med* 2002; 126:1518-26; Zhang Z, et al., Applying classification separability analysis to microarray data. In: Lin S M, Johnson K F, eds. Methods of Microarray data analysis: papers from CAMDA '00. Boston: Kluwer Academic Publishers, 2001:125-136; Zhang Z, et al., Fishing Expedition—a Supervised Approach to Extract Patterns from a Compendium Of Expression Profiles. In: Lin S M, Johnson K F, eds. Microarray Data Analysis II: Papers from CAMDA '01. Boston: Kluwer Academic Publishers, 2002).

To reduce the possibility of choosing peaks as a result of biases or artifacts in the data, the data from the two sites were analyzed independently. A bootstrap re-sampling procedure was used to select peaks that contributed significantly and consistently towards the separation of early stage ovarian cancer and healthy controls. In each bootstrap run, a fixed percentage of the cancer and control samples were randomly selected with replacement for analysis. Individual peaks were ranked according to their contributions in a linear version of UMSA classifier. The mean and standard deviation of each peak's ranks were estimated over multiple (20-40) runs. Peaks with high mean ranks and small standard deviations were selected to form a short list of candidate peaks. The results from the two sites were then cross-compared to determine a final set of peaks with consistent expression patterns as a panel of potential biomarkers.

Multivariate Predictive Models: To construct multivariate predictive models, the data from the two sites were combined and then randomly divided into a training set and a test set. The performance of the panel of potential biomarkers and the derived predictive models were first evaluated on the test set and finally validated on the independent data from the remaining two sites that were not involved in the biomarker discovery and model construction process. Statistical methods for evaluation included sensitivity and specificity estimation and receiver-operating characteristic (ROC) curve analysis.

Example 3

Purification of Biomarkers

For all markers, serum was initially fractionated using the anion exchange protocol used for the protein expression profiling. For each purification step, fractions were monitored either on NP20 or IMAC-copper ProteinChip arrays.

Purification of the 28 kD Marker: 1 ml of the pH 4 fraction from the anion exchange separation was added to 500 ul of RPC PolyBio 10-15 (Biosepra) and incubated at 4° C. for 1 hour. Fractions containing increasing amounts of acetonitrile with 0.1% trifluoroacetic acid were collected. The 75% acetonitrile/0.1% trifluoracetic acid fraction was dried down by speed-vac and rehydrated in 100 ul SDS-tricine sample loading buffer without DTT. 40 ul sample was loaded onto 16% tricine gel and run at 100 mV for 4 hrs. The gel was destained with colloid blue kit (Pierce) and the 28 kDa was excised.

Purification of the 12.8 kDa Marker: 10 ml of the pH 4 fraction from the anion exchange separation was adjusted to pH 7.5 with 1 M Tris HCl, pH 11 and loaded onto 10 ml of MEP beads (Biospra) which had been pre-washed with 20 ml of PBS, pH7.2 three times. The flow through fraction containing the peak was obtained after shaking at 4° C. for 30 minutes. Because this fraction contains a large amount of albumin, immunodepletion of albumin was performed. Protein-A beads were pre-washed with 1.5 ml of PBS containing 0.1% triton-100 three times followed by 1.5 ml of PBS three times. 4 ml of anti-HSA antibody (ICN) was added to 1.5 ml of the Protein-A beads and allowed to couple overnight. The coupled beads were washed with 1 ml PBS with 0.1% triton-100 three times and then three times with 1 ml PBS. The flow through from the MEP column was added to the beads and incubated for one hour at 4° C. The flow through was obtained by spinning at 3000 rcf for 1 minute. The flow through fraction from protein-A-antiHSA antibody column was added to a spin column containing 1.5 ml of RPC PolyBio10-15 resin (Biosepra) which had been pre-washed four times with 1.5 ml of 0.1% TFA. The flow through was removed by spinning at 3000 rcf after incubation at 4° C. for 40 minutes with gently shaking and the bead was washed with 0.8 ml of 0.1% TFA. Fractions containing increasing amounts of acetonitrile with 0.1% trifluoroacetic acid were collected. The 75% acetonitrile/0.1% trifluoracetic acid fraction was dried down by speed-vac and rehydrated in 100 ul SDS-tricine sample loading buffer without DTT. 40 ul sample was loaded onto 16% tricine gel and run at 100 mV for 4 hrs. The gel was destained with colloid blue kit (Pierce) and the 12.8 kDa was excised.

Purification of the 3272 Dalton Biomarker: 1 ml of the flow-through from the anion exchange fractionation was loaded onto 125 ul (250 ul of 50% slurry) of IMAC cellulose (Biosepra) coupled with copper sulfate and incubated at 4° C. for 1 hr. The beads were then washed with a stepwise increasing gradient of imidazole (250 ul each of 20 mM, 50 mM, 100 mM 150 mM and 200 mM Imidazole in 100 mM NaPO$_4$, pH7 with 500 mM NaCl). 200 ul of the fractions containing the biomarker (50-150 mM imidazole) were loaded onto a C18 column (ANSYS technologies, Metachem polaris C18-A5U) and washed with 0.1% TFA for 5 minutes at 1 ml/min followed by a ten minute gradient from 0% ACN to 9% ACN with 0.1% TFA at 1 ml/min. The column was then eluted with a linear gradient from 9% ACN with 0.1% TFA to 45% ACN with 0.1% TFA in 30 minutes at 1 ml/min. The fractions were collected in 1 ml aliquots and the marker eluted in fraction 38 (at which the ACN concentration is 34.2%).

Example 4

Identification of Biomarkers

The purified proteins were digested with trypsin, and the tryptic fragments analyzed on the ProteinChip reader. Each spectrum was an average of at least 250 laser shots and externally calibrated against a mixture of known peptides or internally calibrated using tryptic autolysis and matrix peaks. Peak masses were submitted to the ProFound search peptide mapping site (available online). Protein sequences were retrieved using the NCBI database. Confirmation of these database matches was performed using a PE Sciex QStar (Concord, Canada) equipped with a ProteinChip array interface (Ciphergen). For MS/MS experiments, spectra were acquired on a Sciex QStar (Concord, Ontario, Canada) tandem quadrupole-time of flight mass spectrometer equipped with a Ciphergen PCI 1000 ProteinChip® Array interface. Ions were created using a pulsed nitrogen laser (Laser Science VSL 337 NDS, Franklin, Mass., USA) operated at 30 pulses per second delivering an average pulse fluence of 130 µJ/mm$^2$. Nitrogen gas, at 10 mtorr of pressure, was used for collisional cooling of formed ions as well as for all low energy collision-induced dissociation (CID) experiments. Applied collision energy generally followed the rule of 50 eV/kDa. For MS and MS/MS modes, the system was externally calibrated using a mixture of known peptides. Protein identification was carried out using the UCSF ProteinProspector MS-Tag program (available online; see Clauser K. R. et al. (1999) Anal.l Chem. 71:2871). Database searches with MS-Tag was performed using the following values: *Homo sapiens*, trypsin digest (two missed cleavage allowed), cysteines modified by carbamidomethylation, parent and fragment ion mass tolerance 50 ppm, and NCBI or Swiss-Prot databases.

Confirmation of these identities was performed by EIA or using a ProteinChip array based immunoassay.

Although these proteins have been characterized generally as acute phase reactants, it should be noted that in preliminary studies using immunoassays, the level of apolipoprotein A1 had not been found altered in breast or colon cancer patients and the level of pre-albumin had also not been altered in breast or prostate cancer patients.

Transthyretin is a negative acute phase protein and its levels have been previously reported to be decreased in epithelial ovarian cancer. (Mahlck C G, et al., *Gynecol Obstet Invest*, 1994; 37:135-40). Transthyretin is the major carrier for serum thyroxine and triiodothyronine, and facilitates the transport of retinol via its interaction with retinol binding protein. Transgenic mice lacking transthyretin expression have dramatically lower levels of retinol and retinol binding protein, and (van Bennekum A M, et al., *J Biol Chem* 2001; 276:1107-13) decreased levels of retinol binding protein as well as cellular retinol binding protein have been shown to be associated with an increased rate of malignant tranformation of ovarian epithelium. (van Bennekum A M, et al., *J Biol Chem* 2001; 276:1107-13; Roberts D, et al., *DNA Cell Biol* 2002; 21:11-9). In addition, levels of cellular retinal binding proteins have been reported to be changed in ovarian cancer by oligonucleotide array analysis. (Giordano T J, et al., *Am J Pathol* 2001; 159:1231-8).

The carboxyl portion of IAIH4, from which the m/z 3272 biomarker is derived, has been shown to be a substrate for plasma kallikrein. (Pu X P, et al., *Biochim Biophys Acta* 1994; 1208:338-43; Nishimura H, et al., *FEBS Lett* 1995; 357:207-11). The kallikrein proteases consist of plasma kallikrein and tissue kallikreins, which have overlapping substrate specificity. (Diamandis E P, et al., *Clin Chem* 2002; 48:1198-205). The tissue kallikreins are products of a large multigene family that includes prostate specific antigen (PSA; hK3), a tumor marker for prostate cancer. Several tissue kallikreins have been found to be dys-regulated in ovarian cancer, including hK4, hK5, hK7, hK8, and hK9. (Yousef G M, et al., *Minerva Endocrinol* 2002; 27:157-66).

Transthyretin ΔN10 and IAIH4 fragment are truncation products of mature proteins. These markers may be the product of cleavage by one or more proteases, including plasma kallikrein, tissue kallikreins, matrix metalloproteases, or prostatin, a trypsin-like serine protease that was recently reported to be increased in cases of ovarian cancer. (Mok S C, et al., *J Natl Cancer Inst* 2001; 93:1458-64). The proteases that generate these markers can also be used as markers that can be combined with Markers 1-4 to confer even higher sensitivity and specificity to a predictive model.

Example 5

Discriminatory Power of Individual Biomarkers

Within the discovery set, the difference in expression levels of the three biomarkers between the early stage ovarian cancer patients and the healthy controls were statistically significant (P<0.000001 for markers at m/z 12828 and 28043, P<0.003 for the marker at m/z 3272, P<0.04 for the marker at m/z 3031, and P<0.005 for the marker at m/z 2884) (Table 1).

TABLE 1

Characteristics of Study Samples and Distributions of Age, CA125, and the Three Identified Biomarkers.

| Groups | Number & origin* of samples | | | | | Age** | | CA125 (U/mL) | P | m/z 12828 |
|---|---|---|---|---|---|---|---|---|---|---|
| | A | B | C | D | Total | <50 yr | ≥50 yr | | | |
| Biomarker Discovery Set | | | | | | | | | | |
| Healthy Control | 30 | 49 | | | 79 | 62 | 16 | 13.0 ± 10.2, 10.2 | | 0.40 ± 0.09, 0.42 |
| Epithelial Ovarian Cancer | 20 | 37 | | | 57 | 24 | 33 | 104.1 ± 145.4, 49.7 | <0.000001 | 0.27 ± 0.09, 0.28 |
| Stages I/II Invasive Cancer | 20 | 22 | | | 42 | 17 | 25 | 98.2 ± 143.7, 47.4 | 0.000001 | 0.27 ± 0.10, 0.28 |
| Stage IIIA Invasive Cancer | | 2 | | | 2 | 1 | 1 | 118.9 ± 115.5, 118.9 | n.c.# | 0.24 ± 0.04, 0.24 |
| Stages I/II Borderline Tumor | | 13 | | | 13 | 6 | 7 | 120.8 ± 162.9, 82.6 | <0.000001 | 0.25 ± 0.08, 0.26 |
| Independent Validation Set | | | | | | | | | | |
| Healthy Control | | | | 63 | 63 | 41 | 22 | 13.0 ± 12.2, 10.5 | | 0.39 ± 0.09, 0.38 |
| All Epithelial Ovarian Cancer | | | 138 | | 138 | 35 | 103 | 330.7 ± 337.2, 195.1 | <0.000001 | 0.20 ± 0.09, 0.20 |
| Stages I/II Invasive Cancer | | | 23 | | 23 | 9 | 14 | 180.5 ± 224.7, 74.5 | <0.000001 | 0.22 ± 0.09, 0.21 |
| Stages III/IV Invasive Cancer | | | 86 | | 86 | 17 | 69 | 433.2 ± 357.3, 347.4 | <0.000001 | 0.20 ± 0.08, 0.19 |
| Recurrent | | | 14 | | 14 | 5 | 9 | 208.2 ± 249.1, 95.4 | <0.000001 | 0.20 ± 0.10, 0.20 |
| Stages I/II Borderline Tumor | | | 12 | | 12 | 3 | 9 | 88.3 ± 152.9, 12.2 | 0.000173 | 0.22 ± 0.11, 0.23 |
| Stages III/IV Borderline Tumor | | | 3 | | 3 | 1 | 2 | 84.2 ± 124.2, 18.7 | 0.000009 | 0.19 ± 0.04, 0.21 |
| Benign Pelvic Masses | 50 | 90 | 26 | | 166 | 73 | 91 | 36.1 ± 54.5, 15.7 | <0.000001† | 0.30 ± 0.12, 0.31 |
| Age Groups - All Healthy Controls | | | | | | | | | | |
| Age <50 yr | 25 | 37 | 41 | | 103 | 103 | | 14.0 ± 12.0, 11.0 | 0.087 | 0.41 ± 0.08, 0.42 |
| Age ≥50 yr | 5 | 11 | 22 | | 38 | | 38 | 10.4 ± 7.7, 9.5 | | 0.37 ± 0.08, 0.36 |
| Age Groups - All Stages I/II Invasive Epithelial Ovarian Cancers | | | | | | | | | | |
| Age <50 yr | 10 | 7 | 9 | | 26 | 26 | | 101.9 ± 164.7, 43.8 | 0.356 | 0.27 ± 0.11, 0.27 |
| Age ≥50 yr | 10 | 15 | 14 | | 39 | | 39 | 144.3 ± 188.7, 71.5 | | 0.24 ± 0.09, 0.24 |

| Groups | P | m/z 28043 | P | m/z 3272 | P |
|---|---|---|---|---|---|
| Biomarker Discovery Set | | | | | |
| Healthy Control | | 0.58 ± 0.25, 0.52 | | 0.57 ± 1.06, 0.32 | |
| Epithelial Ovarian Cancer | <0.000001 | 0.36 ± 0.26, 0.29 | 0.000002 | 2.70 ± 2.61, 1.76 | <0.000001 |
| Stages I/II Invasive Cancer | <0.000001 | 0.34 ± 0.27, 0.26 | 0.000004 | 2.11 ± 2.01, 1.54 | <0.000001 |
| Stage IIIA Invasive Cancer | n.c.# | 0.29 ± 0.16, 0.29 | n.c.# | 5.78 ± 7.87, 5.78 | n.c.# |
| Stages I/II Borderline Tumor | <0.000001 | 0.42 ± 0.22, 0.31 | 0.047136 | 4.11 ± 2.82, 3.95 | <0.000001 |
| Independent Validation Set | | | | | |
| Healthy Control | | 0.80 ± 0.41, 0.74 | | 0.64 ± 0.81, 0.28 | |
| All Epithelial Ovarian Cancer | <0.000001 | 0.42 ± 0.30, 0.32 | <0.000001 | 0.98 ± 1.30, 0.41 | 0.059178 |
| Stages I/II Invasive Cancer | <0.000001 | 0.42 ± 0.26, 0.32 | <0.000001 | 1.10 ± 1.59, 0.37 | 0.079999 |
| Stages III/IV Invasive Cancer | <0.000001 | 0.39 ± 0.26, 0.31 | <0.000001 | 0.76 ± 0.99, 0.37 | 0.418525 |
| Recurrent | <0.000001 | 0.43 ± 0.29, 0.36 | 0.002050 | 1.52 ± 1.71, 0.74 | 0.004875 |
| Stages I/II Borderline Tumor | <0.000001 | 0.66 ± 0.50, 0.37 | 0.319724 | 1.72 ± 1.84, 0.91 | 0.001435 |
| Stages III/IV Borderline Tumor | 0.000155 | 0.55 ± 0.24, 0.63 | 0.298460 | 0.64 ± 0.42, 0.60 | 0.994928 |
| Benign Pelvic Masses | <0.000001† | 0.50 ± 0.29, 0.47 | 0.020663† | 2.94 ± 2.68, 2.16 | n.c.‡ |
| Age Groups - All Healthy Controls | | | | | |
| Age <50 yr | 0.013 | 0.68 ± 0.34, 0.59 | 0.853 | 0.52 ± 0.64, 0.32 | 0.101 |
| Age ≥50 yr | | 0.67 ± 0.36, 0.60 | | 0.82 ± 1.50, 0.29 | |

TABLE 1-continued

Characteristics of Study Samples and Distributions of Age, CA125, and the Three Identified Biomarkers.

| | Age Groups - All Stages I/II Invasive Epithelial Ovarian Cancers | | | | | |
|---|---|---|---|---|---|---|
| Age <50 yr | | 0.390 | 0.41 ± 0.31, 0.37 | 0.284 | 1.27 ± 1.66, 0.33 | 0.100 |
| Age ≥50 yr | | | 0.34 ± 0.24, 0.28 | | 2.08 ± 2.04, 1.52 | |

*Origin of samples: (A) Groningen University Hospital, Groningen, the Netherlands, (B) Duke University Medical Center, Durham, NC, (C) Royal Hospital for Women, Sydney, Australia, and (D) MD Anderson Cancer Center, Houston, TX.
**Age: Three samples with missing age data, 1 healthy control in the Biomarker Discovery Set and 2 patients with benign pelvic masses in the Independent Validation Set.
§P-values estimated between patients with ovarian cancer and healthy controls or between two age groups unless specified otherwise.
P-value not computed due to small sample size.
†P-values estimated from two-group T-test between patients with benign pelvic mass and patients with epithelial ovarian cancer in the independent validation set.
‡P-value not computed since the mean peak intensity of m/z 3272 was higher among patients with benign pelvic mass than that in patients with epithelial ovarian cancer in the independent validation set.

FIG. 2 (panels A-D) compares the discriminatory power of the three individual biomarkers with that of CA125 using Receiver operating characteristic (ROC) curve analysis on data from patients with early stage ovarian cancer and healthy controls. For panels A-D, 1: CA125, 2: m/z 12.8 kD, 3: m/z 28 kD, 4: m/z 3272D. CA125 and m/z 12828 performed comparably on both the discovery and independent validation sets, while the other two markers had a lower Area-Under-Curve (AUC) than CA125 in one or both data sets. However, the estimated correlations among the three biomarkers and CA125 were low (data not shown), indicating the possibility that they were complementary to each other and a multivariate approach might outperform the single assay of CA125.

Because 27% of the samples in the healthy controls were from women age 50 or older compared to 61% of those in the early stage ovarian cancer group (P<0.000001), we were concerned that these markers might reflect age-related changes. However, the identified biomarkers were either not significantly different between the age groups or were different at a level comparable to that of CA125 (Table 1). Previous population-based studies have shown that levels of apolipoprotein A1 actually slightly increase with age. (Jungner I, et al., *Clin Chem* 1998; 44:1641-9; Bachorik P S, et al., *Clin Chem* 1997; 43:2364-78).

Example 6

Multivariate Predictive Models

Two multivariate predictive models were constructed using nonlinear UMSA classifiers. The first used only the three biomarkers as its input and the second used the three biomarkers along with the CA125 level. Panels E-H in FIG. 2 compare the overall diagnostic performance of the two models with that of CA125 using ROC analysis. For panels E-H, ○: CA125, □: multivariate model using the three biomarkers, Δ: multivariate model using the three biomarkers and CA125. In the training data, the cutoff value of 0.5 approximately maximized the sum of sensitivity and specificity. Using this cutoff, the models were applied to the test data and the independent validation data (Table 2). For discrimination between healthy controls and stages I/II invasive ovarian cancer in the independent validation set, the multivariate model using the three biomarkers and CA125, at a sensitivity of 82.6% (95% CI 61.2-95.1%), had a specificity of 93.7% (84.5-98.2%). In comparison, CA125 at the cutoff of 11 U/mL had the same sensitivity (82.6%), yet its specificity was only 52.4% (39.4-65.1%). Table 2 also includes the results on patients with benign conditions, late stage invasive cancer, or borderline tumors in the independent validation set.

TABLE 2

Distributions of the Two Multivariate Predictive Models and Comparison of Diagnostic Performance.

| | | CA125 at 35 U/mL | Model with 3 markers§ | |
|---|---|---|---|---|
| Data Sets | N | % correct (95% CI)‡ | mean ± SD, median | % correct (95% CI)‡ |
| Training Set (Part of Biomarker Discovery Set) | | | | |
| Healthy Control | 33 | 97.0% (84.2-99.9) | 0.46 ± 0.04, 0.44 | 87.9% (71.8-96.6) |
| Epithelial Ovarian Cancer | 28 | 67.9% (47.7-84.1) | 0.58 ± 0.06, 0.60 | 89.3% (71.8-97.7) |
| Stages I/II Invasive Cancer | 22 | 63.6% (40.7-82.8) | 0.58 ± 0.06, 0.60 | 86.4% (65.1-97.1) |
| Stage IIIA Invasive Cancer | 1 | n.c.# | 0.60 ± 0.00, 0.60 | n.c.# |
| Stages I/II Borderline Tumor | 5 | 80.0% (28.4-99.5) | 0.58 ± 0.04, 0.57 | 100% (47.8-100.0) |
| Test Set (Part of Biomarker Discovery Set) | | | | |
| Healthy Control | 46 | 97.8% (88.5-99.9) | 0.46 ± 0.04, 0.44 | 91.3% (79.2-97.6) |
| Epithelial Ovarian Cancer | 29 | 65.5% (45.7-82.1) | 0.57 ± 0.07, 0.60 | 82.8% (64.2-94.2) |
| Stages I/II Invasive Cancer | 20 | 70.0% (45.7-88.1) | 0.56 ± 0.07, 0.59 | 75.0% (50.9-91.3) |
| Stage IIIA Invasive Cancer | 1 | n.c.# | 0.61 ± 0.00, 0.61 | n.c.# |
| Stages I/II Borderline Tumor | 8 | 50.0% (15.7-84.3) | 0.58 ± 0.05, 0.58 | 100.0% (63.1-100.0) |
| Independent Validation Set | | | | |
| Healthy Control | 63 | 96.8% (89.0-99.6) | 0.46 ± 0.03, 0.44 | 87.3% (76.5-94.4) |
| All Epithelial Ovarian Cancer | 138 | 76.8% (68.9-83.6) | 0.59 ± 0.07, 0.62 | 83.3% (76.1-89.1) |
| Stages I/II Invasive Cancer | 23 | 65.2% (42.7-83.6) | 0.58 ± 0.07, 0.62 | 87.0% (66.4-97.2) |
| Stages III/IV Invasive Cancer | 86 | 87.2% (78.3-93.4) | 0.60 ± 0.07, 0.62 | 87.2% (78.3-93.4) |
| Recurrent | 14 | 78.6% (49.2-95.3) | 0.58 ± 0.08, 0.61 | 71.4% (41.9-91.6) |
| Stages I/II Borderline Tumor | 12 | 33.3% (9.9-65.1) | 0.58 ± 0.07, 0.60 | 75.0% (42.8-94.5) |

TABLE 2-continued

Distributions of the Two Multivariate Predictive Models and Comparison of Diagnostic Performance.

| | | | | |
|---|---|---|---|---|
| Stages III/IV Borderline Tumor | 3 | 33.3% (0.8-90.6) | 0.52 ± 0.10, 0.47 | 33.3% (0.8-90.6) |
| Benign Pelvic Masses | 166 | 75.9% (68.7-82.2) | 0.54 ± 0.07, 0.53† | 28.9% (22.2-36.5) |

| | Model with 3 markers + CA125§ | | CA125 at 11 U/mL* |
|---|---|---|---|
| Data Sets | mean ± SD, median | % correct (95% CI)‡ | % correct (95% CI)‡ |

Training Set (Part of Biomarker Discovery Set)

| | | | |
|---|---|---|---|
| Healthy Control | 0.21 ± 0.15, 0.14 | 97.0% (84.2-99.9) | 51.5% (33.5-69.2) |
| Epithelial Ovarian Cancer | 0.85 ± 0.12, 0.89 | 100.0% (87.7-100.0) | 89.3% (71.8-97.7) |
| Stages I/II Invasive Cancer | 0.84 ± 0.12, 0.87 | 100.0% (84.6-100.0) | 86.4% (65.1-97.1) |
| Stage IIIA Invasive Cancer | 0.84 ± 0.00, 0.84 | n.c.# | n.c.# |
| Stages I/II Borderline Tumor | 0.93 ± 0.05, 0.93 | 100% (47.8-100.0) | 100% (47.8-100.0) |

Test Set (Part of Biomarker Discovery Set)

| | | | |
|---|---|---|---|
| Healthy Control | 0.19 ± 0.11, 0.16 | 97.8% (88.5-99.9) | 52.2% (37.0-66.9) |
| Epithelial Ovarian Cancer | 0.79 ± 0.27, 0.91 | 86.2% (68.3-96.1) | 100.0% (88.1-100.0) |
| Stages I/II Invasive Cancer | 0.74 ± 0.31, 0.89 | 80.0% (56.3-94.3) | 100.0% (83.2-100.0) |
| Stage IIIA Invasive Cancer | 0.97 ± 0.00, 0.97 | n.c.# | n.c.# |
| Stages I/II Borderline Tumor | 0.87 ± 0.13, 0.91 | 100.0% (63.1-100.0) | 100.0% (63.1-100.0) |

Independent Validation Set

| | | | |
|---|---|---|---|
| Healthy Control | 0.26 ± 0.15, 0.23 | 93.7% (84.5-98.2) | 52.4% (39.4-65.1) |
| All Epithelial Ovarian Cancer | 0.81 ± 0.27, 0.98 | 81.9% (74.4-78.9) | 88.4% (81.9-93.2) |
| Stages I/II Invasive Cancer | 0.73 ± 0.28, 0.81 | 82.6% (61.2-95.1) | 82.6% (61.2-95.1) |
| Stages III/IV Invasive Cancer | 0.88 ± 0.23, 0.99 | 87.2% (78.3-93.4) | 94.2% (87.0-98.1) |
| Recurrent | 0.81 ± 0.25, 0.91 | 85.7% (57.2-98.2) | 92.9% (66.1-99.8) |
| Stages I/II Borderline Tumor | 0.62 ± 0.31, 0.63 | 50.0% (21.1-78.9) | 58.3% (27.7-84.8) |
| Stages III/IV Borderline Tumor | 0.43 ± 0.48, 0.17* | 33.3% (0.8-90.6) | 66.7% (9.4-99.2) |
| Benign Pelvic Masses | 0.62 ± 0.27, 0.66† | 33.1% (26.0-40.9) | 31.9% (24.9-39.6) |

§P-values estimated between patients with ovarian cancer and healthy controls were calculated to be <0.000001 for all comparisons in both models, except for the comparison between stages III/IV borderline tumor compared with healthy controls for which the p values were .316324 and .085588 for the model with three markers and for the model with three markers plus CA125, respectively.
Not computed due to small sample size.
†P-values estimated from two-group T-test between patients with benign pelvic mass and patients with epithelial ovarian cancer in the independent validation set, was calculated to be .011870 for the model with three markers and to be <0.000001 for the model with three markers and CA125.
‡Specificity for healthy controls and patients with benign pelvic mass, and sensitivity for patients with ovarian cancer.
*CA125 cutoff at 11 U/ml selected to match the sensitivity (82.6%) in the independent validation set of the model with three markers plus CA125 for patients with stages I/II invasive ovarian cancer.

FIG. 3 plots the distribution patterns of CA125, the three biomarkers, and the output of the two models over samples in all diagnostic groups. The y-axes is relative intensity in linear scale for all three biomarkers, serum levels in log scale for CA125, and continuous value between 0 (lowest risk of cancer) and 1 (highest risk of cancer) for the two models. Sample groups included: A) healthy controls, B) benign, C) stages I/II invasive cancer, D) stage III/IV invasive cancer, E) recurrent, F) stages I/II borderline tumor. Two IIIc invasive cases in the biomarker discovery set and three stages III/IV borderline tumors in the independent validation set were not plotted.

It should be noted that with the exception of m/z 3272, the other two biomarkers as well as the two predictive models were moderately capable of detecting stages I/II invasive cancer from benign cases (P=0.004 and 0.001 for m/z 12828 and 28043, respectively, and P=0.003 and 0.0001 for models without CA125 and with CA125, respectively).

Example 7

Independent Validation Using Immunoassays

The 142 archived specimens were analyzed for apolipoprotein A1 using a turbidimetric immunoassay performed in a microtiter plate format (Wako Chemical USA), and for transthyretin ΔN10 using a particle enhanced turbidimetric immunoassay performed on the Dimension RxL Instrument (Dade-Behring) (Table 3).

TABLE 3

Distributions of serum levels of CA125, apolipoprotein A1, and transthyretin among 142 archived samples for independent validation using immunoassays.

| | | Age (yrs) | CA125 (U/mL) | | | | Apolipoprotein A1 (mg/dL) | | | | Pre-albumin (mg/dL) | | | |
|---|---|---|---|---|---|---|---|---|---|---|---|---|---|---|
| Diagnostic Group | N | (mean ± SD) | Mean | SD | Median | P | Mean | SD | Median | P | Mean | SD | Median | P |
| Healthy Women | 41 | 33 ± 10 | 17.9 | 23.0 | 10.2 | | 152.8 | 28.1 | 154.3 | | 26.7 | 5.8 | 25.1 | |
| Stages IIIC/IV Ovarian Cancer | 41 | 59 ± 11 | 2387.9 | 4723.3 | 426.6 | 0.001895 | 121.5 | 41.9 | 123.9 | 0.000151 | 19.8 | 7.1 | 18.7 | 0.000006 |
| Breast Cancer | 20 | 53 ± 14 | 13.4 | 13.0 | 7.9 | 0.416705 | 154.4 | 31.8 | 145.9 | 0.844163 | 26.8 | 4.8 | 26.4 | 0.928519 |
| Colon Cancer | 20 | 70 ± 15 | 17.0 | 14.2 | 10.9 | 0.867806 | 144.2 | 39.7 | 149.5 | 0.330148 | 22.4 | 5.1 | 22.8 | 0.006889 |
| Prostate Cancer | 20 | 57 ± 7 | 13.1 | 21.2 | 7.6 | 0.430720 | 138.2 | 21.2 | 136.1 | 0.043676 | 27.8 | 7.8 | 29.8 | 0.546918 |

The serum levels of CA125 were up-regulated, while levels of apolipoprotein A1 and transthyretin ΔN10 were down-regulated among the 41 patients with late stage ovarian cancer compared to the 41 healthy controls (P=0.001895, 0.000151, and 0.000006, respectively). The mean serum apolipoprotein A1 level among the healthy controls was not significantly different from that of patients with breast or colorectal cancer (P=0.844163, 0.330148, respectively) and only marginally different from that of patients with prostate cancer (P=0.043676). The mean serum transthyretin level was down-regulated among patients with colorectal cancer (P=0.006889) albeit to a lesser degree than that in patients with ovarian cancer. There were no significant differences in mean serum transthyretin ΔN10 levels between the healthy controls and patients with breast or prostate cancer (P=0.928519, 0.546918, respectively).

Example 8

Classification Algorithm

Figure 4:
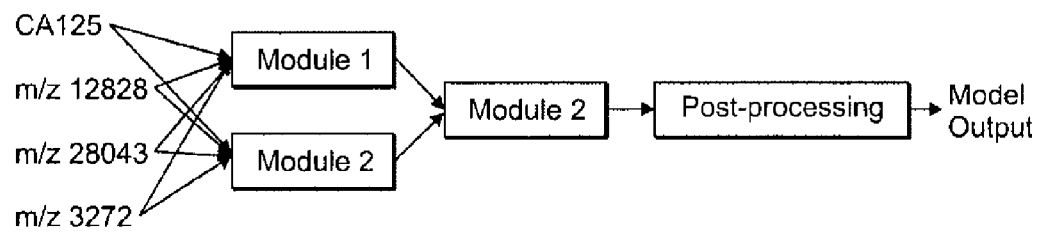
FIG. 4 shows a diagram of the classification algorithm used to characterize the biomarkers.

Referring to the classification algorithm depicted diagrammatically in FIG. 4, Modules 1-3 were trained with the UMSA learning algorithm. The final classifier module, however, has the same mathematical form as a regular support vector machine classifier.

UMSA Classifier Module 1:
  CA125 nm=log(CA125+0.01)
  m/z12.9 Knm=(m/z12828−61.103)/239.031
  m/z28 Knm=(m/z28043−61.3043)/238.9799
  m/z3272 nm=log(m/z3272+0.01)
  Log( ): natural logarithm
  Kernel function: polynomial $<X(:,i),X(:,j)>^{3.0}$
Support Vectors and Coefficients

| CA125 nm | m/z12.9K nm | m/z28K nm | m/z3272 nm | y | alpha |
|---|---|---|---|---|---|
| 2.83966 | −0.25465 | −0.25597 | −1.34323 | 1 | 0.00409 |
| 3.05918 | −0.25416 | −0.25435 | −1.68740 | −1 | 0.03389 |
| 2.39880 | −0.25428 | −0.25529 | 0.42657 | 1 | 0.05926 |
| 3.61658 | −0.25450 | −0.25578 | −1.51413 | 1 | 0.22118 |
| 3.23120 | −0.25417 | −0.25493 | −1.20065 | −1 | 0.29988 |

UMSA Classifier Module 2:
  CA125 nm=log(CA125+0.01)
  m/z12.9 Knm=(m/z12828−0.345)/0.1114
  m/z28 Knm=(m/z28043−0.4834)/0.2792
  m/z3272 nm=log(m/z3272+0.01)
  Log( ): natural logarithm
  Kernel function: $\exp(-|x(:,i)-X(j)|^2/(2*(1.0)^2))$
Support Vectors and Coefficients:

normalized marker values

| CA125 nm | m/z12.9 nm | m/z28 nm | m/z3272 nm | y | alpha |
|---|---|---|---|---|---|
| 2.3618 | 0.1795 | −0.3990 | 0.8717 | 1 | 0.0151 |
| 2.5734 | 0.4758 | 1.2307 | −1.0328 | −1 | 0.0582 |
| 1.6114 | −1.1939 | 0.1311 | −1.3318 | −1 | 0.2112 |
| 2.1175 | 0.1975 | −0.6103 | −1.2588 | −1 | 0.2705 |
| 3.5178 | −0.6014 | −1.3195 | 1.4120 | 1 | 0.2797 |
| 3.8525 | −1.2926 | −0.9327 | −0.2890 | 1 | 0.3556 |
| 2.9658 | −0.6014 | 0.2958 | 1.7483 | 1 | 0.3573 |
| 2.0028 | −0.1167 | 1.4885 | −1.7603 | −1 | 0.4172 |
| 4.1061 | −0.4668 | 1.0766 | 1.1743 | 1 | 0.4281 |
| 4.1776 | −1.1400 | −0.6927 | 1.3463 | 1 | 0.4927 | normalized marker values

| CA125 nm | m/z12.9 nm | m/z28 nm | m/z3272 nm | y | alpha |
|---|---|---|---|---|---|
| 1.5497 | 0.3142 | 1.6390 | −0.6714 | −1 | 0.6698 |
| 1.4839 | −0.8707 | −0.1519 | −0.9113 | −1 | 0.6860 |
| 3.9062 | 0.0987 | 1.9542 | 1.8925 | 1 | 0.7588 |
| 2.3988 | −0.1975 | −0.6748 | 0.4266 | 1 | 1.1697 |
| 3.6166 | −0.6732 | −1.0974 | −1.5141 | 1 | 1.8394 |
| 3.2312 | 0.0269 | −0.3703 | −1.2006 | −1 | 1.8394 |

UMSA Classifier Module 3:
  Kernel function: polynomial $<X(:,i),X(:,j)>^{2.0}$
  X1=exp(module 1 output)/(1+exp(module 1 output))
  X2=module 2 output
Support Vectors and Coefficients:

| X1 | X2 | y | alpha |
|---|---|---|---|
| 0.72862 | 0.41333 | 1 | 0.830900 |
| 0.99835 | 0.25941 | 1 | 1.641283 |
| 0.39802 | 0.57799 | 1 | 1.839397 |
| 0.96185 | 0.23167 | 1 | 1.839397 |
| 0.58865 | 0.18582 | −1 | 1.839397 |
| 0.96194 | 0.21066 | 1 | 1.839397 |
| 0.55377 | 0.10709 | −1 | 1.839397 |
| 0.78444 | 0.05422 | −1 | 1.839397 |
| 0.95604 | −0.01117 | −1 | 1.839397 |
| 0.48706 | 0.28531 | −1 | 2.343210 |

Post-Processing:

$$Y = \begin{cases} \text{Module 3 output}, & \text{if } (CA125 <= 75); \\ \text{Module 3 output} + \log((CA125 + 0.0001)/75)*8/\log(10/3)), & \text{else.} \end{cases}$$

Model output = $\exp(Y/2)/(1+\exp(Y/2))$

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

Example 9

Validation of Markers for Early Stage Ovarian Cancer and Association with Treatment Patients: The study involved 25 women with benign ovarian disease, 53 women with early stage (I, IIa) ovarian cancer, 116 women with late stage ovarian cancer, and 73 healthy controls obtained from two hospitals in Groningen and Leuven. The histologic subtype of the samples were as follows: 95 serous, 29 mucinous, 16 endometrioid, 11 clear cell, 17 adenocarcinoma, and 1 mixed Mullerian. No patients with borderline tumors were included. The average age of women with early stage cancer was 51.8 yrs, late stage cancer was 58.8, benign disease was 47, and healthy controls was 58.

Chromatographic ProteinChip® assay: 5 µL serum was denatured using 7.5 µL 9 M urea/2% CHAPS/50 mM TrisHCl Denatured serum was diluted in biochip binding buffer (50 mM sodium phosphate, 250 mM NaCl, pH 6.0 for IMAC30 arrays or 100 mM sodium phosphate buffer, pH 7.0 for Q10 arrays). Diluted serum was incubated on IMAC30 or Q10 ProteinChip Arrays for two hours. Arrays were washed with binding buffer and then water, and then briefly allowed to air dry. Sinapinic acid was added and the arrays read in a Series 4000 ProteinChip Reader.

Data analysis: Mass spectra were externally calibrated for mass, internally normalized for intensity using total ion current, and baseline subtracted. Peaks were manually selected and the intensity recorded. Data were analyzed using t-tests and support vector machine.

Figure 9:
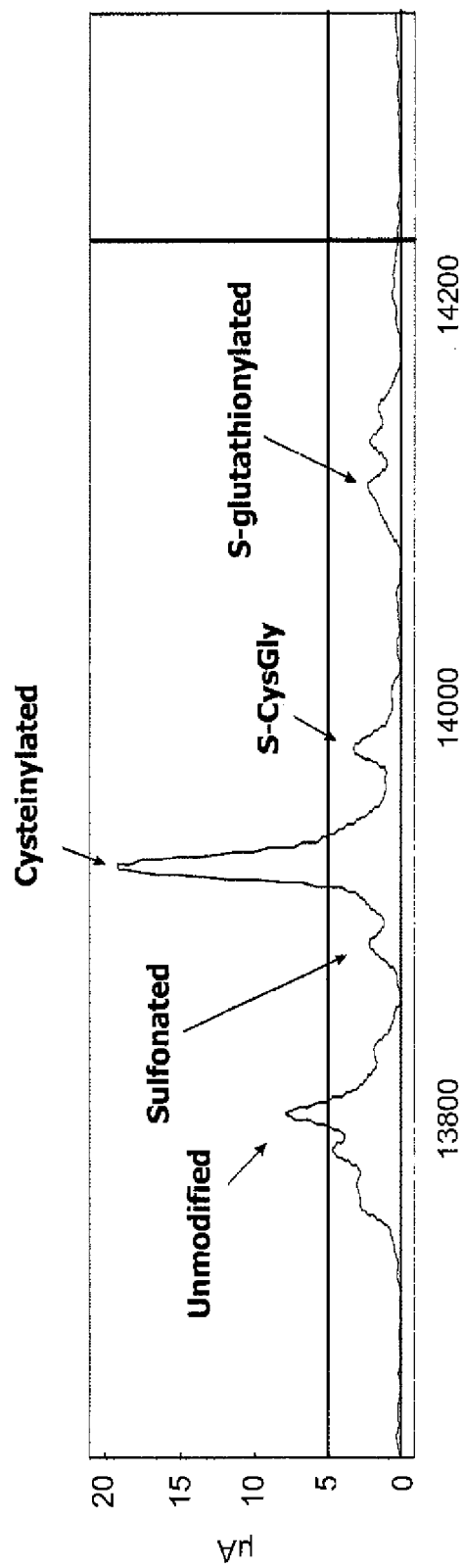
FIG. 9 depicts representative a spectrum of the transthyretin assay on the Q10 ProteinChip Array. Note that five forms of transthyretin can be resolved: unmodified, sulfonated, cys-teinylated, cys-gly, and glutathionylated. In addition, a truncated form of transthyretin (ΔN10) can also be detected; it is present at much lower concentrations (~2%) of the cysteinylated form.

FIG. 9 depicts representative a spectrum of the transthyretin assay on the Q10 ProteinChip Array. Note that five forms of transthyretin can be resolved: unmodified, sulfonated, cysteinylated, cys-gly, and glutathionylated. In addition, a truncated form of transthyretin (ΔN10) can also be detected; it is present at much lower concentrations (~2%) of the cysteinylated form.

Figure 10:
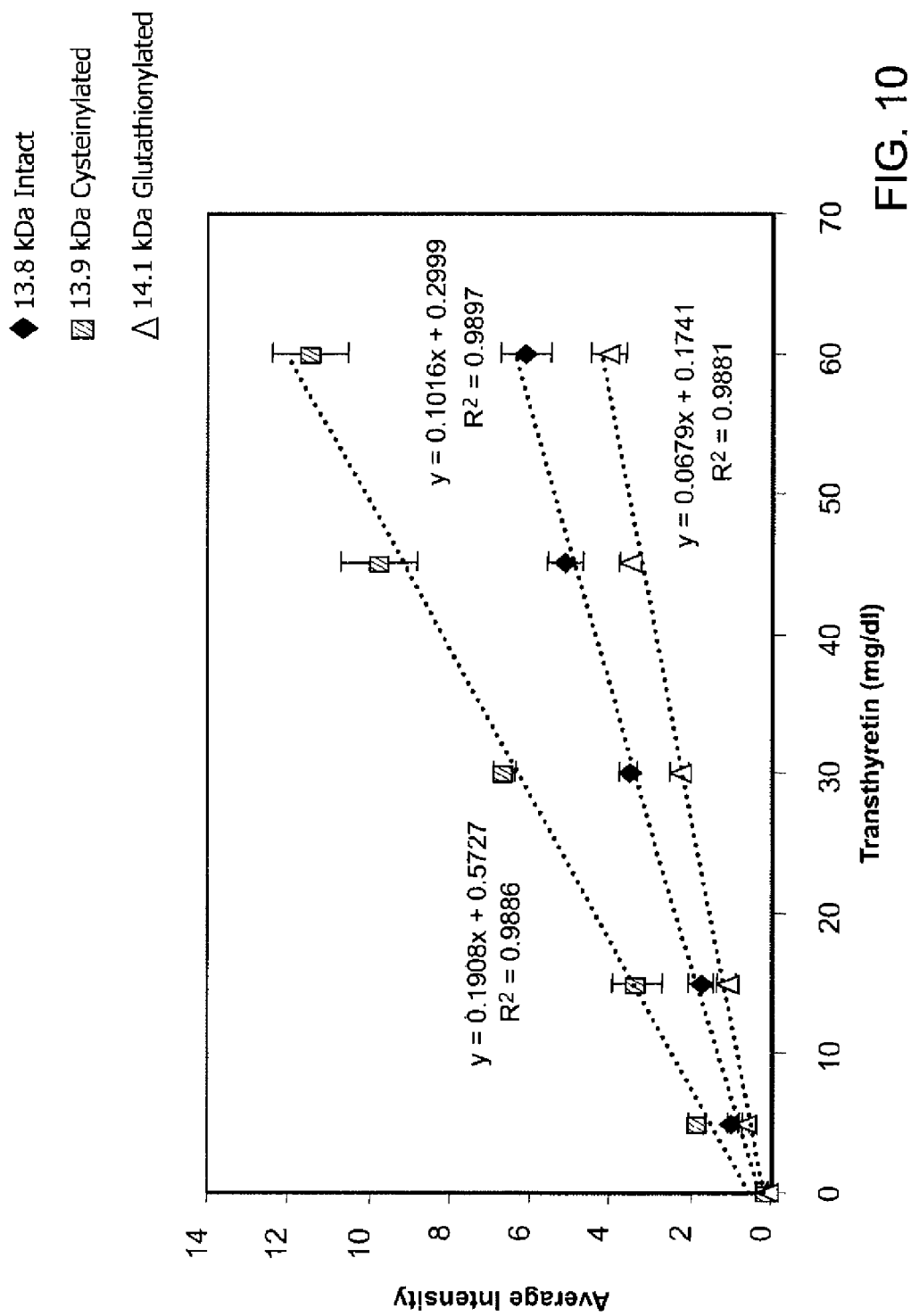
FIG. 10 shows the linear response peak intensity to the concentration of the various forms of transthyretin.

The assay can be absolutely quantitative by using protein standards for calibration. FIG. 10 shows the linear response peak intensity to the concentration of the various forms of transthyretin.

Table 4 shows that transthyretin and apolipoprotein A1 are down-regulated in ovarian cancer. Two-group t-tests demonstrate that five forms of transthyretin and apolipoprotein A1 are down-regulated in patients with either early stage or late stage ovarian cancer. Note that the down-regulation of the transthyretin forms is more pronounced in late stage patients.

Figure 11B:
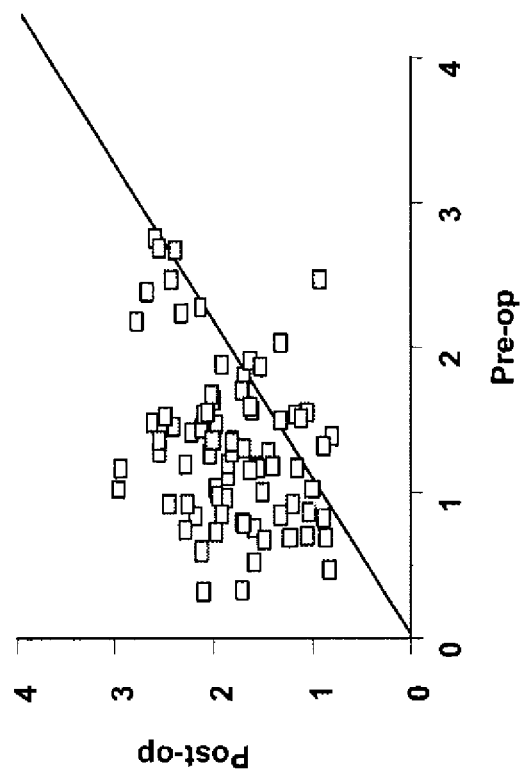
FIG. 11 shows that the combination of transthyretin forms and apolipoprotein A1 changes in response to surgery. A support vector machine algorithm based on the five forms of transthyretin and apolipoprotein A1 was used to create an index score for each patient prior to and after surgery. Pairwise plot of the index score comparing pre-operative levels versus post-operative levels reveal that for most patients, the score increased post-operatively. A. The score increased in 31/42 (73.8%) early stage ovarian cancer patients. B. The score increased in 62/79 (78.5%) of late stage ovarian cancer patients.
Figure 11A:
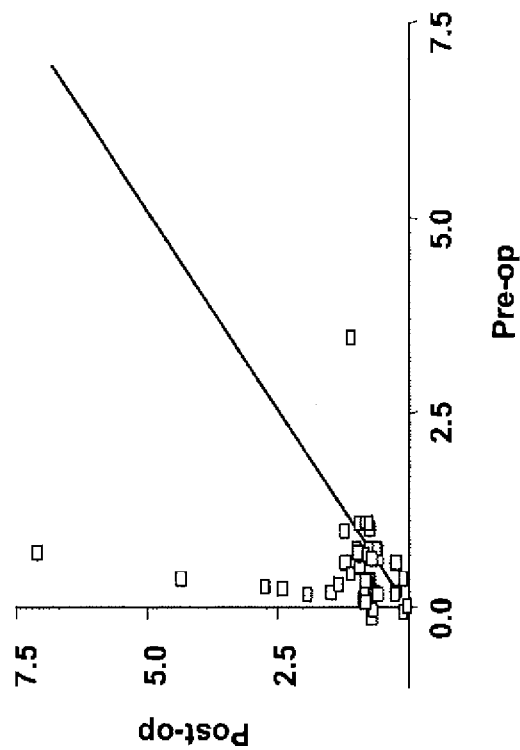
Figure 12:
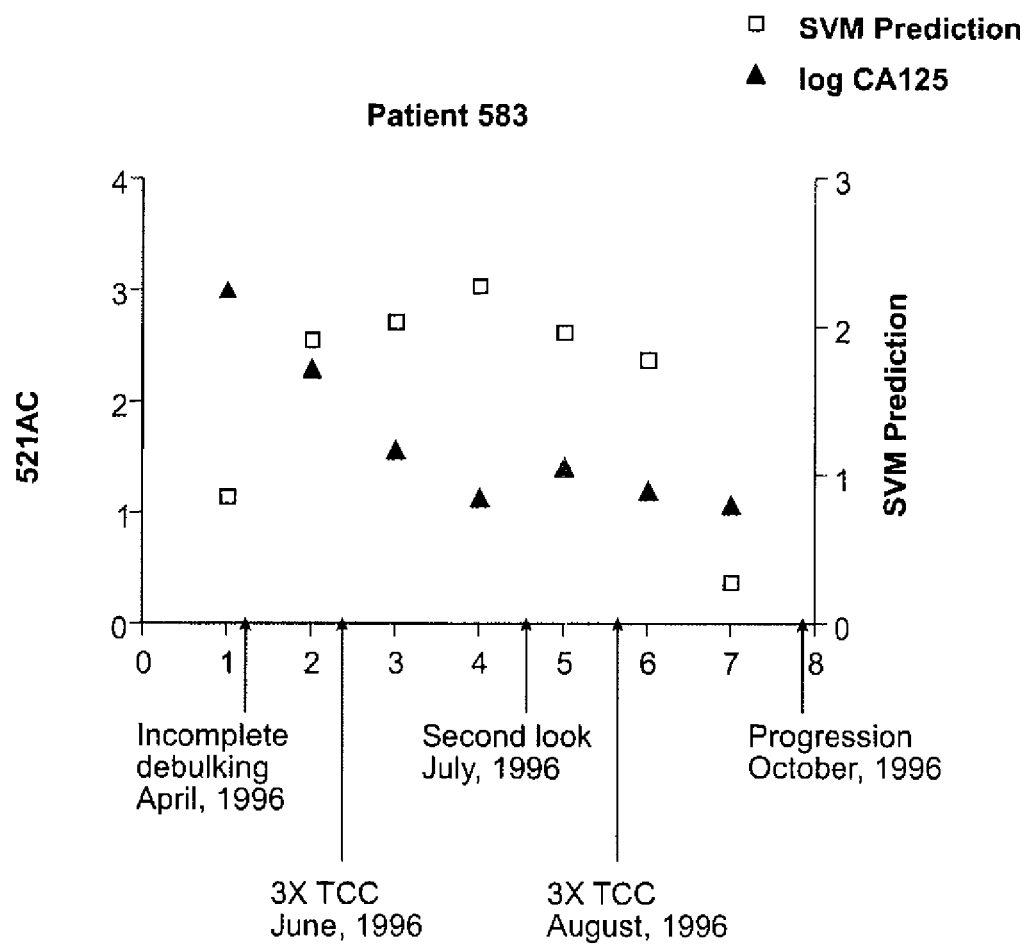
FIG. 12 shows that the index score can be used to monitor patients. An example of how the index score changes during therapy. For this patient, the index score was low pre-operatively, and rose post-operatively. The levels remained high until October, 1996. The patient was demonstrated to have progression of her disease at this time.

As shown in FIG. 11, the combination of transthyretin forms and apolipoprotein A1 changes in response to surgery. A support vector machine algorithm based on the five forms of transthyretin and apolipoprotein A1 was used to create an index score for each patient prior to and after surgery. Pairwise plot of the index score comparing pre-operative levels versus post-operative levels reveal that for most patients, the score increased post-operatively. A. The score increased in 31/42 (73.8%) early stage ovarian cancer patients. B. The score increased in 62/79 (78.5%) of late stage ovarian cancer patients. As shown in FIG. 12, The index score can be used to monitor patients. An example of how the index score changes during therapy. For this patient, the index score was low pre-operatively, and rose post-operatively. The levels remained high until October, 1996. The patient was demonstrated to have progression of her disease at this time.

Example 10

Validation of Markers in a Case-Control Study

Patients: The study involved 45 women with epithelial ovarian cancer, 71 with benign ovarian disease, 122 women with digestive diseases. We excluded one pediatric benign lesion and samples that were thawed and refrozen more than once. The samples for controls were stored longer than the cases and benign disease samples (mean storage time 21 for controls versus 17, years for cases and benign). To minimize bias in detection of peaks associated with storage time we limited the main analysis of the marker data to samples collected from 1983-1989. The data presented here are thus based on 42 ovarian cancer cases, 65 women with benign disease, and 76 controls.

TABLE 4

| Peak | Benign (25) | Control (73) | Early pre (53) | P value | Late pre (116) | P value |
|---|---|---|---|---|---|---|
| CA125 | 13 | 7 | 44 | <.0001 | 886 | <.0001 |
| Unmodified | 3.895 | 5.269 | 3.739 | <.0001 | 2.924 | <.0001 |
| Sulfonated | 3.533 | 5.13 | 3.411 | <.0001 | 3.213 | <.0001 |
| Cysteinylated | 11.74 | 16.51 | 10.67 | <.0001 | 9.456 | <.0001 |
| CysGly | 5.017 | 6.131 | 4.863 | <.0001 | 3.672 | <.0001 |
| Gluathionylated | 3.451 | 4.221 | 3.214 | <.0001 | 2.659 | <.0001 |
| Q10 ApoA1 | 0.3156 | 0.4687 | 0.3203 | <.0001 | 0.3519 | <.0001 |

Table 5 shows that transthyretin and apolipoprotein A1 increase post-operatively. Box-and-whisker plots demonstrate that both transthyretin and apolipoprotein A1 revert to control levels, post-operatively. Paired t-test demonstrates that this effect is statistically significant. Some forms of transthyretin show a greater response than others.

Chromatographic ProteinChip® assay: 5 µL serum was denatured using 7.5 µL 9 M urea/2% CHAPS/50 mM TrisHCl. Denatured serum was diluted in array binding buffer (50 mM sodium phosphate, 250 mM NaCl, pH 6.0 for IMAC30 arrays or 100 mM sodium phosphate buffer, pH 7.0 for Q10 arrays). Diluted serum was incubated on IMAC30 or

TABLE 5

| Peak | Early pre (53) | Early post (53) | P value | Late pre (116) | Late post (116) | P value |
|---|---|---|---|---|---|---|
| CA125 | 44 | 8 | <.0001 | 886 | 121 | <.0001 |
| Unmodified | 3.739 | 5.006 | .004 | 2.924 | 4.028 | <.0001 |
| Sulfonated | 3.411 | 4.629 | .002 | 3.213 | 4.006 | .002 |
| Cysteinylated | 10.67 | 15.61 | .007 | 9.456 | 13.82 | <.0001 |
| CysGly | 4.863 | 6.096 | .006 | 3.672 | 5.004 | <.0001 |
| Gluathionylated | 3.214 | 4.303 | .01 | 2.659 | 3.507 | <.0001 |
| Q10 ApoA1 | 0.3203 | 0.3714 | .002 | 0.3519 | 0.436 | <.0001 |

Q10 ProteinChip Arrays for two hours. Arrays were washed with binding buffer and then water, and then briefly allowed to air dry. Sinapinic acid was added and the arrays read in a Series 4000 ProteinChip Reader.

Data analysis: Mass spectra were externally calibrated for mass, internally normalized for intensity using total ion current, and baseline subtracted. Peaks were manually selected and the intensity recorded. Demographic characteristics were compared using Fisher exact tests. T-tests were used to assess differences in peak height between groups. Linear and quadratic discriminant analysis and nearest neighbor methods were used to build classifiers. Error rates in the classifications were assessed using cross validation.

TABLE 6

Demographic and clinical characteristics of the samples included in this study

| Characteristics | Controls (N = 76) | Benign Disease (N = 65) | Cases (N = 42) |
|---|---|---|---|
| Age in years-mean (range) | 59 (19-88) | 41 (15-74) | 61 (21-78) |
| Smoking Status N (%) | | | |
| Never | 48 (63%) | 37 (57%) | 29 (69%) |
| Past | 13 (17%) | 11 (17%) | 11 (26%) |
| Current | 10 (13%) | 17 (26%) | 2 (5%) |

TABLE 6-continued

Demographic and clinical characteristics of the samples included in this study

| Characteristics | Controls (N = 76) | Benign Disease (N = 65) | Cases (N = 42) |
|---|---|---|---|
| Packs/day mean ± SD | 1.3 ± 2.9 | 1.0 ± 2.1 | 0.7 ± 2.1 |
| CA125-U/mL mean ± SD | 20.5 ± 19.3 | 29.9 ± 32.7 | 1563.9 ± 3385.9 |

Figure 13:
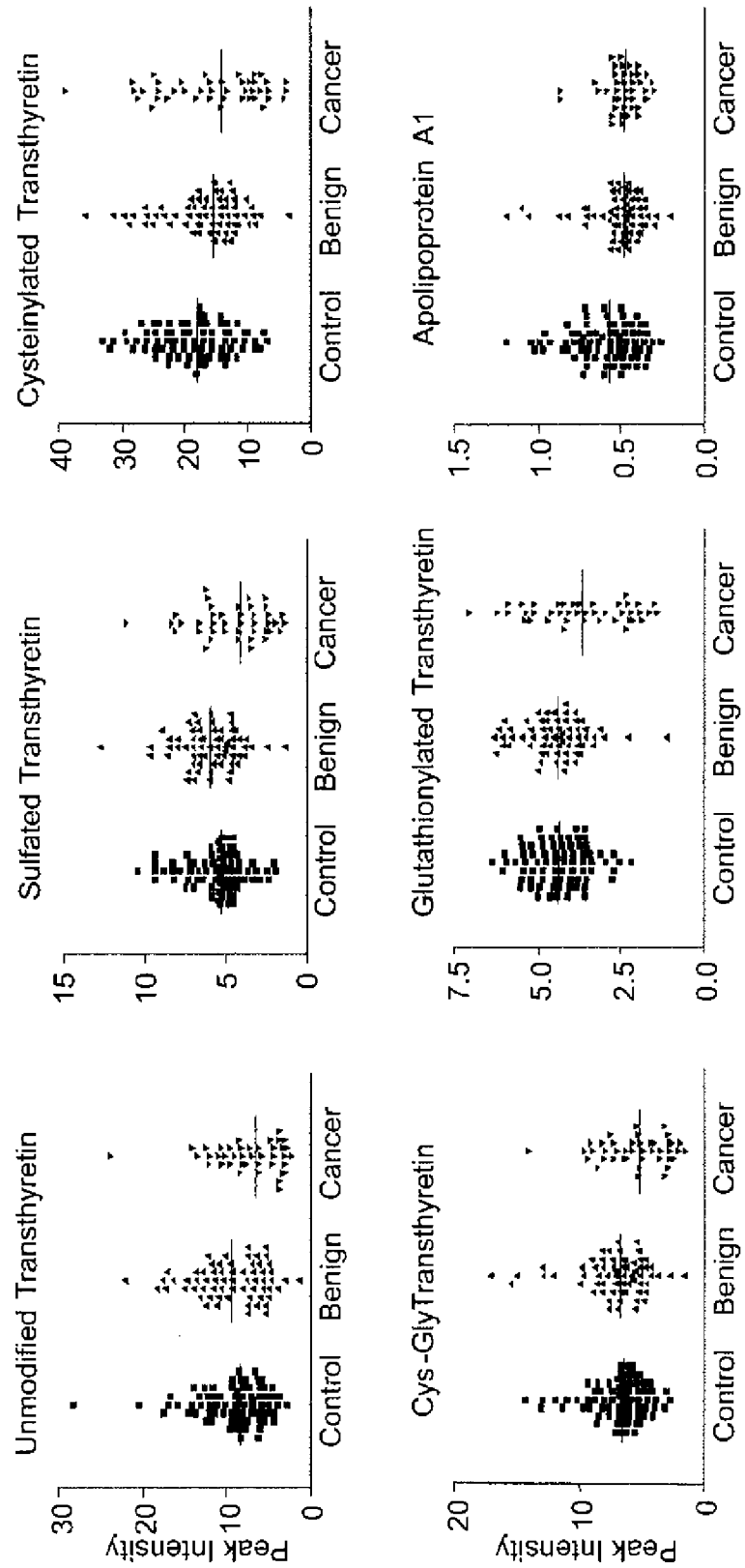
FIG. 13 shows scatter plots of peak intensity for transthyretin forms and apolipoprotein A1 on Q10 ProteinChip array. The two-group t-test for the forms of transthyretin are as follows: unmodified, 0.0076; sulfonated, 0.0052; cysteinylated, 0.0104; cys-gly, 0.0026; and glutathionylated, 0.0047. The two group t-test for apolipoprotein A1 is 0.0009.

FIG. 13 shows scatter plots of peak intensity for transthyretin forms and apolipoprotein A1 on Q10 ProteinChip array. The two-group t-test for the forms of transthyretin are as follows: unmodified, 0.0076; sulfonated, 0.0052; cysteinylated, 0.0104; cys-gly, 0.0026; and glutathionylated, 0047. The two group t-test for apolipoprotein A1 is 0.0009.

Figure 14:
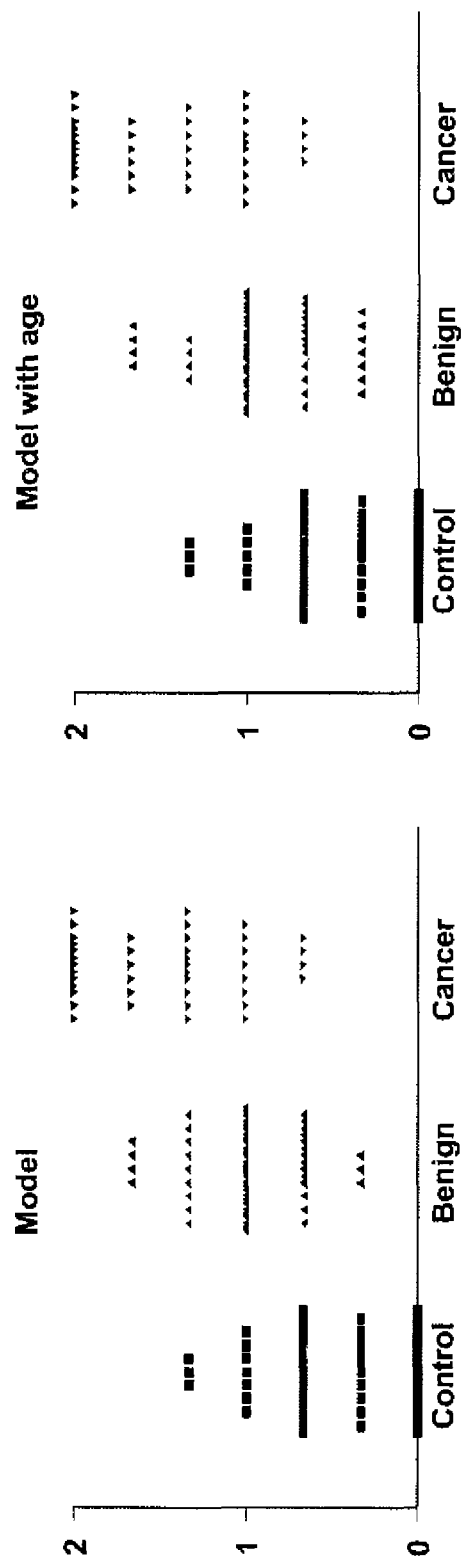
FIG. 14 shows the index score for nearest neighbor analysis. The peak intensities of the six transthyretin forms and apolipoprotein A1, excluding age or including age, were input into the model. Nearest neighbor analysis using was performed to calculate the posterior probabilities of being a control, benign, or cancer case for each sample. The posterior expectation of class membership was computed as p(benign|markers)+2*p(cancer|markers). as p(benign|markers)+2*p(cancer|markers). A score of 0 indicates that the sample was classified clearly as a control, while a score of 2 indicates that the sample was classified clearly as cancer. Intermediate scores reflect increasing probability of cancer being present, as the score approaches 2.

FIG. 14 shows index score for nearest neighbor analysis. The peak intensities of the six transthyretin forms and apolipoprotein A1, excluding age or including age, were input into the model. Nearest neighbor analysis using was performed to calculate the posterior probabilities of being a control, benign, or cancer case for each sample. The posterior expectation of class membership was computed as p(benign|markers)+2*p(cancer|markers). as p(benign|markers)+2*p(cancer|markers). A score of 0 indicates that the sample was classified clearly as a control, while a score of 2 indicates that the sample was classified clearly as cancer.

What is claimed is:

1. A method of qualifying ovarian cancer status in a subject comprising:
    (a) measuring using mass spectrometry or an immunoassay, biomarkers comprising modified ApoA1, and one or more modified transthyretin selected from the group consisting of cysteinylated transthyretin, sulfonated transthyretin, CysGly modified transthyretin, glutathionylated transthyretin, and combinations thereof, and
    (b) comparing the level of one or more of modified ApoA1 and modified transthyretin in said sample to a control level, wherein a decrease in said level of modified ApoA1 and modified transthyretin is indicative of ovarian cancer.

2. The method of claim 1 further comprising:
    (c) managing subject treatment based on the status.

3. The method of claim 2, wherein managing subject treatment is selected from ordering more tests, performing surgery, and taking no further action.

4. The method of claim 2 further comprising:
    (d) measuring the at least one biomarker after subject management.

5. The method of claim 1 wherein the ovarian cancer status is selected from the group consisting of the subject's risk of cancer, the presence or absence of disease, the stage of disease and the effectiveness of treatment of disease.

6. The method of claim 5 further comprising measuring at least one known biomarker in a sample from the subject and correlating measurement of the known biomarker with ovarian cancer status.

7. The method of claim 6, wherein the known biomarker is selected from CA125, CAI25 II, CA15-3, CA19-9, CA72-4, CA 195, tumor associated trypsin inhibitor (TATI), CEA, placental alkaline phosphatase (PLAP), Sialyl TN, galactosyltransferase, macrophage colony stimulating factor (M-CSF, CSF-1), lysophosphatidic acid (LPA), 110 kD component of the extracellular domain of the epidermal growth factor receptor (p110EGFR), tissue kallikreins, e.g., kallikrein 6 and kallikrein 10 (IMES-1), prostasin, HE4, creatine kinase B (CKB), LASA, HER-2/neu, urinary gonadotropin peptide, Dianon NB 70/K, Tissue peptide antigen (TPA), osteopontin and haptoglobin, and protein variants, cleavage forms, and isoforms of the markers.

8. The method of claim 1, wherein the modified transthyretin is cysteinylated transthyretin.

9. The method of claim 1 comprising measuring modified ApoA1, cysteinylated transthyretin, sulfonated transthyretin, CysGly modified transthyretin, and glutathionylated transthyretin.

10. The method of claim 1 wherein the correlating is performed by a software classification algorithm.

11. The method of claim 1 wherein the sample is selected from blood, serum and plasma.

* * * * *

SEQUENCE LISTING

```
<160> NUMBER OF SEQ ID NOS: 9

<210> SEQ ID NO 1
<211> LENGTH: 30
<212> TYPE: PRT
<213> ORGANISM: Homo sapiens

<400> SEQUENCE: 1

Met Asn Phe Arg Pro Gly Val Leu Ser Ser Arg Gln Leu Gly Leu Pro
 1               5                  10                  15

Gly Pro Pro Asp Val Pro Asp His Ala Ala Tyr His Pro Phe
            20                  25                  30

<210> SEQ ID NO 2
<211> LENGTH: 28
<212> TYPE: PRT
<213> ORGANISM: Homo sapiens

<400> SEQUENCE: 2

Phe Arg Pro Gly Val Leu Ser Ser Arg Gln Leu Gly Leu Pro Gly Pro
 1               5                  10                  15

Pro Asp Val Pro Asp His Ala Ala Tyr His Pro Phe
            20                  25

<210> SEQ ID NO 3
<211> LENGTH: 27
<212> TYPE: PRT
<213> ORGANISM: Homo sapiens

<400> SEQUENCE: 3

Arg Pro Gly Val Leu Ser Ser Arg Gln Leu Gly Leu Pro Gly Pro Pro
 1               5                  10                  15
```

Asp Val Pro Asp His Ala Ala Tyr His Pro Phe
            20                  25

<210> SEQ ID NO 4
<211> LENGTH: 29
<212> TYPE: PRT
<213> ORGANISM: Homo sapiens

<400> SEQUENCE: 4

Asn Phe Arg Pro Gly Val Leu Ser Ser Arg Gln Leu Gly Leu Pro Gly
1               5                   10                  15

Pro Pro Asp Val Pro Asp His Ala Ala Tyr His Pro Phe
            20                  25

<210> SEQ ID NO 5
<211> LENGTH: 26
<212> TYPE: PRT
<213> ORGANISM: Homo sapiens

<400> SEQUENCE: 5

Pro Gly Val Leu Ser Ser Arg Gln Leu Gly Leu Pro Gly Pro Pro Asp
1               5                   10                  15

Val Pro Asp His Ala Ala Tyr His Pro Phe
            20                  25

<210> SEQ ID NO 6
<211> LENGTH: 25
<212> TYPE: PRT
<213> ORGANISM: Homo sapiens

<400> SEQUENCE: 6

Gly Val Leu Ser Ser Arg Gln Leu Gly Leu Pro Gly Pro Pro Asp Val
1               5                   10                  15

Pro Asp His Ala Ala Tyr His Pro Phe
            20                  25

<210> SEQ ID NO 7
<211> LENGTH: 24
<212> TYPE: PRT
<213> ORGANISM: Homo sapiens

<400> SEQUENCE: 7

Val Leu Ser Ser Arg Gln Leu Gly Leu Pro Gly Pro Pro Asp Val Pro
1               5                   10                  15

Asp His Ala Ala Tyr His Pro Phe
            20

<210> SEQ ID NO 8
<211> LENGTH: 23
<212> TYPE: PRT
<213> ORGANISM: Homo sapiens

<400> SEQUENCE: 8

Leu Ser Ser Arg Gln Leu Gly Leu Pro Gly Pro Pro Asp Val Pro Asp
1               5                   10                  15

His Ala Ala Tyr His Pro Phe
            20

<210> SEQ ID NO 9
<211> LENGTH: 22
<212> TYPE: PRT
<213> ORGANISM: Homo sapiens

<400> SEQUENCE: 9

```
Ser Ser Arg Gln Leu Gly Leu Pro Gly Pro Pro Asp Val Pro Asp His
1               5                   10                  15

Ala Ala Tyr His Pro Phe
            20
```